(12) United States Patent
Kamal et al.

(10) Patent No.: US 10,392,385 B2
(45) Date of Patent: Aug. 27, 2019

(54) N-((1-PHENYL-9H-PYRIDO[3,4-B]INDOL-3-YL)METHYL)CINNAMAMIDES AS POTENTIAL ANTICANCER AGENTS AND PREPARATION THEREOF

(71) Applicant: Council of Scientific & Industrial Research, New Delhi (IN)

(72) Inventors: Ahmed Kamal, Hyderabad (IN);
Sathish Manda, Hyderabad (IN);
Nagesh Narayana, Hyderabad (IN);
Shankaraiah Nagula, Hyderabad (IN);
Chetan Dushantrao Sabanis, Hyderabad (IN); Hari Krishna Namballa, Hyderabad (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 16/071,687

(22) PCT Filed: Jan. 20, 2017

(86) PCT No.: PCT/IN2017/050031
§ 371 (c)(1),
(2) Date: Jul. 20, 2018

(87) PCT Pub. No.: WO2017/125952
PCT Pub. Date: Jul. 27, 2017

(65) Prior Publication Data
US 2019/0023703 A1    Jan. 24, 2019

(30) Foreign Application Priority Data

Jan. 22, 2016   (IN) .............................. 201611002389

(51) Int. Cl.
C07D 471/04    (2006.01)

(52) U.S. Cl.
CPC .................................. C07D 471/04 (2013.01)

(58) Field of Classification Search
CPC .................................................. C07D 471/04
USPC ......................................................... 546/87
See application file for complete search history.

(56) References Cited

FOREIGN PATENT DOCUMENTS

GB              975835 A       11/1964
WO         2011063223 A1        5/2011

OTHER PUBLICATIONS

Allen, et al., "The Simple B-Carboline Alkaloids", Phytochemistry, vol. 19, No. 8, Jan. 1980, pp. 1573-1582.
Daugan, et al., "The Discovery of Tadalafil: A Novel and Highly Selective PDE5 Inhibitor. 1: 5,6,11,11a-Tetrahydro-1H-imidazo[1',5':1,6]pyrido[3,4-b]indole-1,3(2H)-dione Analogues", Journal of Medicinal Chemistry, vol. 46, No. 21, Oct. 2003, pp. 4533-4542.
International Search Report and Written Opinion for PCT/IN2017/050031, dated Jun. 13, 2017.
Kamal, et al., "Design and Synthesis of Dithiocarbamate Linked B-carboline Derivatives: DNA Topoisomerase II Inhibition with DNA Binding and Apoptosis Inducing Ability", Bioorganic & Medicinal Chemistry, vol. 23, No. 17, Sep. 2015, pp. 5511-5526.
Leslie, et al., "Phenylcinnamides as Novel Antimitotic Agents", Journal of Medicinal Chemistry, vol. 53, No. 10, Apr. 2010, pp. 3964-3972.
Rook, et al., "Bivalent B-Carbolines as Potential Multitarget Anti-Alzheimer Agents", Journal of Medicinal Chemistry, vol. 53, No. 9, Apr. 2010, pp. 3611-3617.
Turski, et al., "Anticonvulsant Action of the B-Carboline Abecarnil: Studies in Rodents and Baboon, Papio Papio", Journal of Pharmacology and Experimental Therapeutics, vol. 253, No. 1, Apr. 1990, pp. 344-352.

*Primary Examiner* — Rita J Desai
(74) *Attorney, Agent, or Firm* — Lerner, David, Littenberg, Krumholz & Mentlik, LLP

(57) ABSTRACT

A compound of general formula A, useful as potential anticancer agents against human cancer cell lines and process for the preparation thereof. General formula A $R_1$=3-F, 3,4,5-OMe, 4-OMe, H, 4-$CF_3$, 4-Cl, 4-OH-3-OMe, 3,4-$CH_2$—O—$CH_2$, 3,5-F, 4-OH, 1-napthyl, 9-phenanthryl, 4-Me. $R_2$=3,4,5-OMe, 3,4-Cl, 4-F, 3,5-F, 2,5-OMe, 4-Cl, 4-OH-3-OMe, 3-OH, 3,4,5-OH, 4-$CF_3$, 4-OMe, 4-$NH_2$.

General formula A

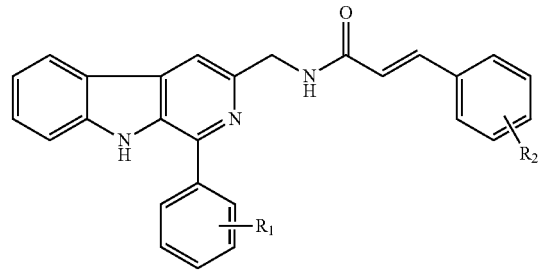

10 Claims, No Drawings

N-((1-PHENYL-9H-PYRIDO[3,4-B]INDOL-3-YL)METHYL)CINNAMAMIDES AS POTENTIAL ANTICANCER AGENTS AND PREPARATION THEREOF

CROSS-REFERENCE TO RELATED APPLICATIONS

The present application is a national phase entry under 35 U.S.C. § 371 of International Application No. PCT/IN2017/050031 filed Jan. 20, 2017, published in English, which claims priority from Indian Patent Application No. 201611002389 filed Jan. 22, 2016, all of which are incorporated herein by reference.

FIELD OF THE INVENTION

The present invention relates to N-((1-phenyl-9H-pyrido[3,4-b]indol-3-yl)methyl)cinnamamides as cytotoxic agents. Particularly, the present invention relates to a process for the preparation thereof. More, particularly, present invention relates to N-((1-phenyl-9H-pyrido[3,4-b]indol-3-yl)methyl) cinnamamides of general formula A.

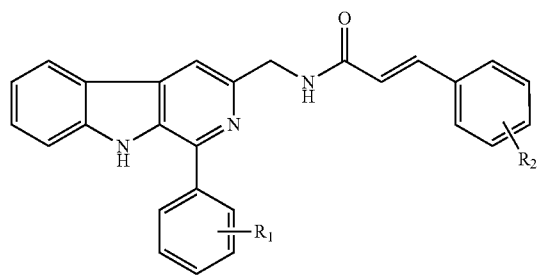

A $R_1$=3-F, 3,4,5-OMe, 4-OMe, H, 4-$CF_3$, 4-Cl, 4-OH-3-OMe, 3,4-$CH_2$—O—$CH_2$, 3,5-F, 4-OH, 1-napthyl, 9-phenanthryl, 4-Me, $R_2$=3,4,5-OMe, 3,4-Cl, 4-F, 3,5-F, 2,5-OMe, 4-Cl, 4-OH-3-OMe, 3-OH, 3,4,5-OH, 4-$CF_3$, 4-OMe, 4-$NH_2$.

BACKGROUND OF THE INVENTION

β-Carbolines are of great interest due to their broad spectrum of biochemical effects and pharmaceutical functions (Allen, J. R.; Holmstedt, B. R. *Phytochemistry* 1979, 19, 1573). In particular, there have been intense research efforts in recent years in the design and development of β-carbolines as a new class of antitumor agents. β-Carbolines are initially discovered to exert their antitumor effects by intercalating into DNA. Subsequent investigations suggested that this class of compounds might exert their antitumor effects through multiple mechanisms of action, such as inhibiting topoisomerase I and II (Topo-I and II), cyclin-dependent kinase (CDK), mitogen activated protein kinase-activated protein kinase 2 (MK-2), kinesin-like protein Eg5 and I-Kappa-B kinase (IKK) (Rook, Y.; Schmidtke, K.; Gaube, F.; Schepmann, D.; Weunsch, B.; Heilmann, J.; Lehmann, J.; Winckler, T. *J. Med. Chem.* 2010, 53, 3611). Further, the importance of β-carboline-based compounds is underscored by the fact that two of these, Tadalafil (Daugan, A.; Grondin, P.; Ruault, C.; de Gouville, A. C. L. M.; Coste, H.; Kirilovsky, J.; Hyafil, F.; Labaudiniere, R. *J. Med. Chem.* 2003, 46, 4525) and Abecarnil (Turski, L.; Stephens, D. N.; Jensen, L. H.; Peterson, E. N.; Meldrum, B. S.; Patel, S.; Hansen, J. B.; Loscher, W.; Schneider, H. H.; Schmiechen, R. *J. Pharmacol. Exp. Ther.* 1990, 253, 344) are clinically used for erectile dysfunction and CNS disorders, respectively.

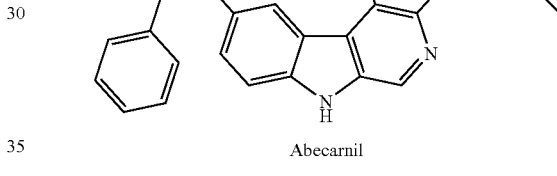

Tadalafil

Abecarnil

During the last decade, natural products bearing the cinnamoyl moiety have attracted much attention due to their broad spectrum of biological activities and low toxicity. Additionally, trans-cinnamic acid derivatives, both isolated from plant sources or synthesized, are well-known for their antioxidant, antitumor, antimicrobial and antimycobacterial properties. Cinnamic acid derivatives, especially those combining the cinnamoyl moiety with hydroxyl groups' exluitrat free radical scavenging properties. Acids, esters, amides, hydrazides and related derivatives of cinnamic acid with such activities are reported in the literature for their health benefits (Leslie, B. J.; Holaday, C. R.; Nguyen, T.; Hergenrother, P. J. *J. Med. Chem.* 2010, 53, 3964).

OBJECTIVES OF THE INVENTION

The main object of the present invention is to provide novel N-((1-phenyl-9H-pyrido[3,4-b]indol-3-yl)methyl)cinnamamides 1a-l to 13a-l as useful cytotoxic agents.

Yet another object of this invention is to provide a process for the preparation of novel N-((1-phenyl-9H-pyrido[3,4-b]indol-3-yl)methyl)cinnamamides.

SUMMARY OF THE INVENTION

Accordingly, present invention provides to N-((1-phenyl-9H-pyrido[3,4-b]indol-3-yl)methyl) cinnamamides general formula A.

A

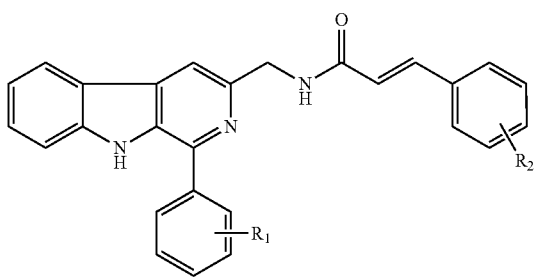

R$_1$=3-F, 3,4,5-OMe, 4-OMe, H, 4-CF$_3$, 4-Cl, 4-OH-3-OMe, 3,4-CH$_2$—O—CH$_2$, 3,5-F, 4-OH, 1-napthyl, 9-phenanthryl, 4-Me R$_2$=3,4,5-OMe, 3,4-Cl, 4-F, 3,5-F, 2,5-OMe, 4-Cl, 4-OH-3-OMe, H, 3,4,5-OH, 4-CF$_3$, 4-OMe, 4-NH$_2$ In an embodiment of the present invention, chemical formulas of the representative compounds of formula 1a-l to 13a-l are (E)-N-((1-(3-fluorophenyl)-9H-pyrido[3,4-b]indol-3-yl)methyl)-3-(3,4,5-trimethoxyphenyl)acrylamide (1a)

(E)-3-(3,4-dichlorophenyl)-N-((1-(3-fluorophenyl)-9H-pyrido[3,4-b]indol-3-yl)methyl)acrylamide (1b)

(E)-3-(4-fluorophenyl)-N-((1-(3-fluorophenyl)-9H-pyrido[3,4-b]indol-3-yl)methyl)acrylamide (1c)

(E)-3-(3,5-difluorophenyl)-N-((1-(3-fluorophenyl)-9H-pyrido[3,4-b]indol-3-yl)methyl)acrylamide (1d)

(E)-3-(2,5-dimethoxyphenyl)-N-((1-(3-fluorophenyl)-9H-pyrido[3,4-b]indol-3-yl)methyl)acrylamide (1e)

(E)-3-(4-chlorophenyl)-N-((1-(3-fluorophenyl)-9H-pyrido[3,4-b]indol-3-yl)methyl)acrylamide (1f)

(E)-N-((1-(3-fluorophenyl)-9H-pyrido[3,4-b]indol-3-yl)methyl)-3-(4-hydroxy-3-methoxyphenyl)acrylamide (1g)

(E)-N-((1-(3-fluorophenyl)-9H-pyrido[3,4-b]indol-3-yl)methyl)-3-(3-hydroxyphenyl)acrylamide (1h)

(E)-N-((1-(3-fluorophenyl)-9H-pyrido[3,4-b]indol-3-yl)methyl)-3-(3,4,5-trihydroxyphenyl)acrylamide (1i)

(E)-N-((1-(3-fluorophenyl)-9H-pyrido[3,4-b]indol-3-yl)methyl)-3-(4-(trifluoromethyl)phenyl)acrylamide (1j)

(E)-N-((1-(3-fluorophenyl)-9H-pyrido[3,4-b]indol-3-yl)methyl)-3-(4-methoxyphenyl)acrylamide (1k)

(E)-3-(4-aminophenyl)-N-((1-(3-fluorophenyl)-9H-pyrido[3,4-b]indol-3-yl)methyl)acrylamide (1l)

(E)-3-(3,4,5-trimethoxyphenyl)-N-((1-(3,4,5-trimethoxyphenyl)-9H-pyrido[3,4-b]indol-3-yl)methyl)acrylamide (2a)

(E)-3-(3,4-dichlorophenyl)-N-((1-(3,4,5-trimethoxyphenyl)-9H-pyrido[3,4-b]indol-3-yl)methyl)acrylamide (2b)

(E)-3-(4-fluorophenyl)-N-((1-(3,4,5-trimethoxyphenyl)-9H-pyrido[3,4-b]indol-3-yl)methyl)acrylamide (2c)

(E)-3-(3,5-difluorophenyl)-N-((1-(3,4,5-trimethoxyphenyl)-9H-pyrido[3,4-b]indol-3-yl)methyl)acrylamide (2d)

(E)-3-(2,5-dimethoxyphenyl)-N-((1-(3,4,5-trimethoxyphenyl)-9H-pyrido[3,4-b]indol-3-yl)methyl)acrylamide (2e)

(E)-3-(4-chlorophenyl)-N-((1-(3,4,5-trimethoxyphenyl)-9H-pyrido[3,4-b]indol-3-yl)methyl)acrylamide (2f)

(E)-3-(4-hydroxy-3-methoxyphenyl)-N-((1-(3,4,5-trimethoxyphenyl)-9H-pyrido[3,4-b]indol-3-yl)methyl)acrylamide (2g)

(E)-3-(3-hydroxyphenyl)-N-((1-(3,4,5-trimethoxyphenyl)-9H-pyrido[3,4-b]indol-3-yl)methyl)acrylamide (2h)

(E)-3-(3,4,5-trihydroxyphenyl)-N-((1-(3,4,5-trimethoxyphenyl)-9H-pyrido[3,4-b]indol-3-yl)methyl)acrylamide (2i)

(E)-3-(4-(trifluoromethyl)phenyl)-N-((1-(3,4,5-trimethoxyphenyl)-9H-pyrido[3,4-b]indol-3-yl)methyl)acrylamide (2j)

(E)-3-(4-methoxyphenyl)-N-((1-(3,4,5-trimethoxyphenyl)-9H-pyrido[3,4-b]indol-3-yl)methyl)acrylamide (2k)

(E)-3-(4-aminophenyl)-N-((1-(3,4,5-trimethoxyphenyl)-9H-pyrido[3,4-b]indol-3-yl)methyl)acrylamide (2l)

(E)-N-((1-(4-methoxyphenyl)-9H-pyrido[3,4-b]indol-3-yl)methyl)-3-(3,4,5-trimethoxyphenyl)acrylamide (3a)

(E)-3-(3,4-dichlorophenyl)-N-((1-(4-methoxyphenyl)-9H-pyrido[3,4-b]indol-3-yl)methyl)acrylamide (3b)

(E)-3-(4-fluorophenyl)-N-((1-(4-methoxyphenyl)-9H-pyrido[3,4-b]indol-3-yl)methyl)acrylamide (3c)

(E)-3-(3,5-difluorophenyl)-N-((1-(4-methoxyphenyl)-9H-pyrido[3,4-b]indol-3-yl)methyl)acrylamide (3d)

(E)-3-(2,5-dimethoxyphenyl)-N-((1-(4-methoxyphenyl)-9H-pyrido[3,4-b]indol-3-yl)methyl)acrylamide (3e)

(E)-3-(4-chlorophenyl)-N-((1-(4-methoxyphenyl)-9H-pyrido[3,4-b]indol-3-yl)methyl)acrylamide (3f)

(E)-3-(4-hydroxy-3-methoxyphenyl)-N-((1-(4-methoxyphenyl)-9H-pyrido[3,4-b]indol-3-yl)methyl)acrylamide (3g)

(E)-3-(3-hydroxyphenyl)-N-((1-(4-methoxyphenyl)-9H-pyrido[3,4-b]indol-3-yl)methyl)acrylamide (3h)

(E)-N-((1-(4-methoxyphenyl)-9H-pyrido[3,4-b]indol-3-yl)methyl)-3-(3,4,5-trihydroxyphenyl)acrylamide (3i)

(E)-N-((1-(4-methoxyphenyl)-9H-pyrido[3,4-b]indol-3-yl)methyl)-3-(4-(trifluoromethyl)phenyl)acrylamide (3j)

(E)-3-(4-methoxyphenyl)-N-((1-(4-methoxyphenyl)-9H-pyrido[3,4-b]indol-3-yl)methyl)acrylamide (3k)

(E)-3-(4-aminophenyl)-N-((1-(4-methoxyphenyl)-9H-pyrido[3,4-b]indol-3-yl)methyl)acrylamide (3l)

(E)-N-((1-phenyl-9H-pyrido[3,4-b]indol-3-yl)methyl)-3-(3,4,5-trimethoxyphenyl)acrylamide (4a)

(E)-3-(3,4-dichlorophenyl)-N-((1-phenyl-9H-pyrido[3,4-b]indol-3-yl)methyl)acrylamide (4b)

(E)-3-(4-fluorophenyl)-N-((1-phenyl-9H-pyrido[3,4-b]indol-3-yl)methyl)acrylamide (4c)

(E)-3-(3,5-difluorophenyl)-N-((1-phenyl-9H-pyrido[3,4-b]indol-3-yl)methyl)acrylamide (4d)

(E)-3-(2,5-dimethoxyphenyl)-N-((1-phenyl-9H-pyrido[3,4-b]indol-3-yl)methyl)acrylamide (4e)

(E)-3-(4-chlorophenyl)-N-((1-phenyl-9H-pyrido[3,4-b]indol-3-yl)methyl)acrylamide (4f)

(E)-3-(4-hydroxy-3-methoxyphenyl)-N-((1-phenyl-9H-pyrido[3,4-b]indol-3-yl)methyl)acrylamide (4g)

(E)-3-(3-hydroxyphenyl)-N-((1-phenyl-9H-pyrido[3,4-b]indol-3-yl)methyl)acrylamide (4h)

(E)-N-((1-phenyl-9H-pyrido[3,4-b]indol-3-yl)methyl)-3-(3,4,5-trihydroxyphenyl)acrylamide (4i);

(E)-N-((1-phenyl-9H-pyrido[3,4-b]indol-3-yl)methyl)-3-(4-(trifluoromethyl)phenyl)acrylamide (4j)

(E)-3-(4-methoxyphenyl)-N-((1-phenyl-9H-pyrido[3,4-b]indol-3-yl)methyl)acrylamide (4k)

(E)-3-(4-aminophenyl)-N-((1-phenyl-9H-pyrido[3,4-b]indol-3-yl)methyl)acrylamide (4l)

(E)-N-((1-(4-(trifluoromethyl)phenyl)-9H-pyrido[3,4-b]indol-3-yl)methyl)-3-(3,4,5-trimethoxyphenyl)acrylamide (5a)

(E)-3-(3,4-dichlorophenyl)-N-((1-(4-(trifluoromethyl)phenyl)-9H-pyrido[3,4-b]indol-3-yl)methyl)acrylamide (5b)

(E)-3-(4-fluorophenyl)-N-((1-(4-(trifluoromethyl)phenyl)-9H-pyrido[3,4-b]indol-3-yl)methyl)acrylamide (5c)

(E)-3-(3,5-difluorophenyl)-N-((1-(4-(trifluoromethyl)phenyl)-9H-pyrido[3,4-b]indol-3-yl)methyl)acrylamide (5d)

(E)-3-(2,5-dimethoxyphenyl)-N-((1-(4-(trifluoromethyl)phenyl)-9H-pyrido[3,4-b]indol-3-yl)methyl)acrylamide (5e)

(E)-3-(4-chlorophenyl)-N-((1-(4-(trifluoromethyl)phenyl)-9H-pyrido[3,4-b]indol-3-yl)methyl)acrylamide (5f)
(E)-3-(4-hydroxy-3-methoxyphenyl)-N-((1-(4-(trifluoromethyl)phenyl)-9H-pyrido[3,4-b]indol-3-yl)methyl)acrylamide (5g)
(E)-3-(3-hydroxyphenyl)-N-((1-(4-(trifluoromethyl)phenyl)-9H-pyrido[3,4-b]indol-3-yl)methyl)acrylamide (5h)
(E)-N-((1-(4-(trifluoromethyl)phenyl)-9H-pyrido[3,4-b]indol-3-yl)methyl)-3-(3,4,5-trihydroxyphenyl)acrylamide (5i)
(E)-3-(4-(trifluoromethyl)phenyl)-N-((1-(4-(trifluoromethyl)phenyl)-9H-pyrido[3,4-b]indol-3-yl)methyl)acrylamide (5j)
(E)-3-(4-methoxyphenyl)-N-((1-(4-(trifluoromethyl)phenyl)-9H-pyrido[3,4-b]indol-3-yl)methyl)acrylamide (5k)
(E)-3-(4-aminophenyl)-N-((1-(4-(trifluoromethyl)phenyl)-9H-pyrido[3,4-b]indol-3-yl)methyl)acrylamide (5l)
(E)-N-((1-(4-chlorophenyl)-9H-pyrido[3,4-b]indol-3-yl)methyl)-3-(3,4,5-trimethoxyphenyl)acrylamide (6a)
(E)-N-((1-(4-chlorophenyl)-9H-pyrido[3,4-b]indol-3-yl)methyl)-3-(3,4-dichlorophenyl)acrylamide (6b)
(E)-N-((1-(4-chlorophenyl)-9H-pyrido[3,4-b]indol-3-yl)methyl)-3-(4-fluorophenyl)acrylamide (6c)
(E)-N-((1-(4-chlorophenyl)-9H-pyrido[3,4-b]indol-3-yl)methyl)-3-(3,5-difluorophenyl)acrylamide (6d)
(E)-N-((1-(4-chlorophenyl)-9H-pyrido[3,4-b]indol-3-yl)methyl)-3-(2,5-dimethoxyphenyl)acrylamide (6e)
(E)-3-(4-chlorophenyl)-N-((1-(4-chlorophenyl)-9H-pyrido[3,4-b]indol-3-yl)methyl)acrylamide (6f)
(E)-N-((1-(4-chlorophenyl)-9H-pyrido[3,4-b]indol-3-yl)methyl)-3-(4-hydroxy-3-methoxyphenyl)acrylamide (6g)
(E)-N-((1-(4-chlorophenyl)-9H-pyrido[3,4-b]indol-3-yl)methyl)-3-(3-hydroxyphenyl)acrylamide (6h)
(E)-N-((1-(4-chlorophenyl)-9H-pyrido[3,4-b]indol-3-yl)methyl)-3-(3,4,5-trihydroxyphenyl)acrylamide (6i)
(E)-N-((1-(4-chlorophenyl)-9H-pyrido[3,4-b]indol-3-yl)methyl)-3-(4-(trifluoromethyl)phenyl)acrylamide (6j)
(E)-N-((1-(4-chlorophenyl)-9H-pyrido[3,4-b]indol-3-yl)methyl)-3-(4-methoxyphenyl)acrylamide (6k)
(E)-3-(4-aminophenyl)-N-((1-(4-chlorophenyl)-9H-pyrido[3,4-b]indol-3-yl)methyl)acrylamide (6l)
(E)-N-((1-(4-hydroxy-3-methoxyphenyl)-9H-pyrido[3,4-b]indol-3-yl)methyl)-3-(3,4,5-trimethoxyphenyl)acrylamide (7a)
(E)-3-(3,4-dichlorophenyl)-N-((1-(4-hydroxy-3-methoxyphenyl)-9H-pyrido[3,4-b]indol-3-yl)methyl)acrylamide (7b)
(E)-3-(4-fluorophenyl)-N-((1-(4-hydroxy-3-methoxyphenyl)-9H-pyrido[3,4-b]indol-3-yl)methyl)acrylamide (7c)
(E)-3-(3,5-difluorophenyl)-N-((1-(4-hydroxy-3-methoxyphenyl)-9H-pyrido[3,4-b]indol-3-yl)methyl)acrylamide (7d)
(E)-3-(2,5-dimethoxyphenyl)-N-((1-(4-hydroxy-3-methoxyphenyl)-9H-pyrido[3,4-b]indol-3-yl)methyl)acrylamide (7e)
(E)-3-(4-chlorophenyl)-N-((1-(4-hydroxy-3-methoxyphenyl)-9H-pyrido[3,4-b]indol-3-yl)methyl)acrylamide (7f)
(E)-3-(4-hydroxy-3-methoxyphenyl)-N-((1-(4-hydroxy-3-methoxyphenyl)-9H-pyrido[3,4-b]indol-3-yl)methyl)acrylamide (7g)
(E)-N-((1-(4-hydroxy-3-methoxyphenyl)-9H-pyrido[3,4-b]indol-3-yl)methyl)-3-(3-hydroxyphenyl)acrylamide (7h)
(E)-N-((1-(4-hydroxy-3-methoxyphenyl)-9H-pyrido[3,4-b]indol-3-yl)methyl)-3-(3,4,5-trihydroxyphenyl)acrylamide (7i)
(E)-N-((1-(4-hydroxy-3-methoxyphenyl)-9H-pyrido[3,4-b]indol-3-yl)methyl)-3-(4-(trifluoromethyl)phenyl)acrylamide (7j)
(E)-N-((1-(4-hydroxy-3-methoxyphenyl)-9H-pyrido[3,4-b]indol-3-yl)methyl)-3-(4-methoxyphenyl)acrylamide (7k)
(E)-3-(4-aminophenyl)-N-((1-(4-hydroxy-3-methoxyphenyl)-9H-pyrido[3,4-b]indol-3-yl)methyl)acrylamide (7l)
(E)-N-((1-(benzo[d][1,3]dioxol-5-yl)-9H-pyrido[3,4-b]indol-3-yl)methyl)-3-(3,4,5-trimethoxyphenyl)acrylamide (8a)
(E)-N-((1-(benzo[d][1,3]dioxol-5-yl)-9H-pyrido[3,4-b]indol-3-yl)methyl)-3-(3,4-dichlorophenyl)acrylamide (8b)
(E)-N-((1-(benzo[d][1,3]dioxol-5-yl)-9H-pyrido[3,4-b]indol-3-yl)methyl)-3-(4-fluorophenyl)acrylamide (8c)
(E)-N-((1-(benzo[d][1,3]dioxol-5-yl)-9H-pyrido[3,4-b]indol-3-yl)methyl)-3-(3,5-difluorophenyl)acrylamide (8d)
(E)-N-((1-(benzo[d][1,3]dioxol-5-yl)-9H-pyrido[3,4-b]indol-3-yl)methyl)-3-(2,5-dimethoxyphenyl)acrylamide (8e)
(E)-N-((1-(benzo[d][1,3]dioxol-5-yl)-9H-pyrido[3,4-b]indol-3-yl)methyl)-3-(4-chlorophenyl)acrylamide (8f)
(E)-N-((1-(benzo[d][1,3]dioxol-5-yl)-9H-pyrido[3,4-b]indol-3-yl)methyl)-3-(4-hydroxy-3-methoxyphenyl)acrylamide (8g)
(E)-N-((1-(benzo[d][1,3]dioxol-5-yl)-9H-pyrido[3,4-b]indol-3-yl)methyl)-3-(3-hydroxyphenyl)acrylamide (8h)
(E)-N-((1-(benzo[d][1,3]dioxol-5-yl)-9H-pyrido[3,4-b]indol-3-yl)methyl)-3-(3,4,5-trihydroxyphenyl)acrylamide (8i)
(E)-N-((1-(benzo[d][1,3]dioxol-5-yl)-9H-pyrido[3,4-b]indol-3-yl)methyl)-3-(4-(trifluoromethyl)phenyl)acrylamide (8j)
(E)-N-((1-(benzo[d][1,3]dioxol-5-yl)-9H-pyrido[3,4-b]indol-3-yl)methyl)-3-(4-methoxyphenyl)acrylamide (8k)
(E)-3-(4-aminophenyl)-N-((1-(benzo[d][1,3]dioxol-5-yl)-9H-pyrido[3,4-b]indol-3-yl)methyl)acrylamide (8l)
(E)-N-((1-(3,5-difluorophenyl)-9H-pyrido[3,4-b]indol-3-yl)methyl)-3-(3,4,5-trimethoxyphenyl)acrylamide (9a)
(E)-3-(3,4-dichlorophenyl)-N-((1-(3,5-difluorophenyl)-9H-pyrido[3,4-b]indol-3-yl)methyl)acrylamide (9b)
(E)-N-((1-(3,5-difluorophenyl)-9H-pyrido[3,4-b]indol-3-yl)methyl)-3-(4-fluorophenyl)acrylamide (9c)
(E)-3-(3,5-difluorophenyl)-N-((1-(3,5-difluorophenyl)-9H-pyrido[3,4-b]indol-3-yl)methyl)acrylamide (9d)
(E)-N-((1-(3,5-difluorophenyl)-9H-pyrido[3,4-b]indol-3-yl)methyl)-3-(2,5-dimethoxyphenyl)acrylamide (9e)
(E)-3-(4-chlorophenyl)-N-((1-(3,5-difluorophenyl)-9H-pyrido[3,4-b]indol-3-yl)methyl)acrylamide (9f)
(E)-N-((1-(3,5-difluorophenyl)-9H-pyrido[3,4-b]indol-3-yl)methyl)-3-(4-hydroxy-3-methoxyphenyl)acrylamide (9g)
(E)-N-((1-(3,5-difluorophenyl)-9H-pyrido[3,4-b]indol-3-yl)methyl)-3-(3-hydroxyphenyl)acrylamide (9h)
(E)-N-((1-(3,5-difluorophenyl)-9H-pyrido[3,4-b]indol-3-yl)methyl)-3-(3,4,5-trihydroxyphenyl)acrylamide (9i)
(E)-N-((1-(3,5-difluorophenyl)-9H-pyrido[3,4-b]indol-3-yl)methyl)-3-(4-(trifluoromethyl)phenyl)acrylamide (9j)
(E)-N-((1-(3,5-difluorophenyl)-9H-pyrido[3,4-b]indol-3-yl)methyl)-3-(4-methoxyphenyl)acrylamide (9k)
(E)-3-(4-aminophenyl)-N-((1-(3,5-difluorophenyl)-9H-pyrido[3,4-b]indol-3-yl)methyl)acrylamide (9l)
(E)-N-((1-(4-hydroxyphenyl)-9H-pyrido[3,4-b]indol-3-yl)methyl)-3-(3,4,5-trimethoxyphenyl)acrylamide (10a)
(E)-3-(3,4-dichlorophenyl)-N-((1-(4-hydroxyphenyl)-9H-pyrido[3,4-b]indol-3-yl)methyl)acrylamide (10b)
(E)-3-(4-fluorophenyl)-N-((1-(4-hydroxyphenyl)-9H-pyrido[3,4-b]indol-3-yl)methyl)acrylamide (10c)

(E)-3-(3,5-difluorophenyl)-N-((1-(4-hydroxyphenyl)-9H-pyrido[3,4-b]indol-3-yl)methyl)acrylamide (10d)
(E)-3-(2,5-dimethoxyphenyl)-N-((1-(4-hydroxyphenyl)-9H-pyrido[3,4-b]indol-3-yl)methyl)acrylamide (10e)
(E)-3-(4-chlorophenyl)-N-((1-(4-hydroxyphenyl)-9H-pyrido[3,4-b]indol-3-yl)methyl)acrylamide (10f)
(E)-3-(4-hydroxy-3-methoxyphenyl)-N-((1-(4-hydroxyphenyl)-9H-pyrido[3,4-b]indol-3-yl)methyl)acrylamide (10g)
(E)-3-(3-hydroxyphenyl)-N-((1-(4-hydroxyphenyl)-9H-pyrido[3,4-b]indol-3-yl)methyl)acrylamide (10h)
(E)-N-((1-(4-hydroxyphenyl)-9H-pyrido[3,4-b]indol-3-yl)methyl)-3-(3,4,5-trihydroxyphenyl)acrylamide (10i)
(E)-N-((1-(4-hydroxyphenyl)-9H-pyrido[3,4-b]indol-3-yl)methyl)-3-(4-(trifluoromethyl)phenyl)acrylamide (10j)
(E)-N-((1-(4-hydroxyphenyl)-9H-pyrido[3,4-b]indol-3-yl)methyl)-3-(4-methoxyphenyl)acrylamide (10k)
(E)-3-(4-aminophenyl)-N-((1-(4-hydroxyphenyl)-9H-pyrido[3,4-b]indol-3-yl)methyl)acrylamide (10l)
(E)-N-((1-(naphthalen-1-yl)-9H-pyrido[3,4-b]indol-3-yl)methyl)-3-(3,4,5-trimethoxyphenyl)acrylamide (11a)
(E)-3-(3,4-dichlorophenyl)-N-((1-(naphthalen-1-yl)-9H-pyrido[3,4-b]indol-3-yl)methyl)acrylamide (11b)
(E)-3-(4-fluorophenyl)-N-((1-(naphthalen-1-yl)-9H-pyrido[3,4-b]indol-3-yl)methyl)acrylamide (11c)
(E)-3-(3,5-difluorophenyl)-N-((1-(naphthalen-1-yl)-9H-pyrido[3,4-b]indol-3-yl)methyl)acrylamide (11d)
(E)-3-(2,5-dimethoxyphenyl)-N-((1-(naphthalen-1-yl)-9H-pyrido[3,4-b]indol-3-yl)methyl)acrylamide (11e)
(E)-3-(4-chlorophenyl)-N-((1-(naphthalen-1-yl)-9H-pyrido[3,4-b]indol-3-yl)methyl)acrylamide (11f)
(E)-3-(4-hydroxy-3-methoxyphenyl)-N-((1-(naphthalen-1-yl)-9H-pyrido[3,4-b]indol-3-yl)methyl)acrylamide (11g)
(E)-3-(3-hydroxyphenyl)-N-((1-(naphthalen-1-yl)-9H-pyrido[3,4-b]indol-3-yl)methyl)acrylamide (11h)
(E)-N-((1-(naphthalen-1-yl)-9H-pyrido[3,4-b]indol-3-yl)methyl)-3-(3,4,5-trihydroxyphenyl)acrylamide (11i)
(E)-N-((1-(naphthalen-1-yl)-9H-pyrido[3,4-b]indol-3-yl)methyl)-3-(4-(trifluoromethyl)phenyl)acrylamide (11j)
(E)-3-(4-methoxyphenyl)-N-((1-(naphthalen-1-yl)-9H-pyrido[3,4-b]indol-3-yl)methyl)acrylamide (11k)
(E)-3-(4-aminophenyl)-N-((1-(naphthalen-1-yl)-9H-pyrido[3,4-b]indol-3-yl)methyl)acrylamide (11l)
(E)-N-((1-(phenanthren-9-yl)-9H-pyrido[3,4-b]indol-3-yl)methyl)-3-(3,4,5-trimethoxyphenyl)acrylamide (12a)
(E)-3-(3,4-dichlorophenyl)-N-((1-(phenanthren-9-yl)-9H-pyrido[3,4-b]indol-3-yl)methyl)acrylamide (12b)
(E)-3-(4-fluorophenyl)-N-((1-(phenanthren-9-yl)-9H-pyrido[3,4-b]indol-3-yl)methyl)acrylamide (12c)
(E)-3-(3,5-difluorophenyl)-N-((1-(phenanthren-9-yl)-9H-pyrido[3,4-b]indol-3-yl)methyl)acrylamide (12d)
(E)-3-(2,5-dimethoxyphenyl)-N-((1-(phenanthren-9-yl)-9H-pyrido[3,4-b]indol-3-yl)methyl)acrylamide (12e)
(E)-3-(4-chlorophenyl)-N-((1-(phenanthren-9-yl)-9H-pyrido[3,4-b]indol-3-yl)methyl)acrylamide (12f)
(E)-3-(4-hydroxy-3-methoxyphenyl)-N-((1-(phenanthren-9-yl)-9H-pyrido[3,4-b]indol-3-yl)methyl)acrylamide (12g)
(E)-3-(3-hydroxyphenyl)-N-((1-(phenanthren-9-yl)-9H-pyrido[3,4-b]indol-3-yl)methyl)acrylamide (12h)
(E)-N-((1-(phenanthren-9-yl)-9H-pyrido[3,4-b]indol-3-yl)methyl)-3-(3,4,5-trihydroxyphenyl)acrylamide (12i)
(E)-N-((1-(phenanthren-9-yl)-9H-pyrido[3,4-b]indol-3-yl)methyl)-3-(4-(trifluoromethyl)phenyl)acrylamide (12j)
(E)-3-(4-methoxyphenyl)-N-((1-(phenanthren-9-yl)-9H-pyrido[3,4-b]indol-3-yl)methyl)acrylamide (12k)
(E)-3-(4-aminophenyl)-N-((1-(phenanthren-9-yl)-9H-pyrido[3,4-b]indol-3-yl)methyl)acrylamide (12l)
(E)-N-((1-(p-tolyl)-9H-pyrido[3,4-b]indol-3-yl)methyl)-3-(3,4,5-trimethoxyphenyl)acrylamide (13a)
(E)-3-(3,4-dichlorophenyl)-N-((1-(p-tolyl)-9H-pyrido[3,4-b]indol-3-yl)methyl)acrylamide (13b)
(E)-3-(4-fluorophenyl)-N-((1-(p-tolyl)-9H-pyrido[3,4-b]indol-3-yl)methyl)acrylamide (13c)
(E)-3-(3,5-difluorophenyl)-N-((1-(p-tolyl)-9H-pyrido[3,4-b]indol-3-yl)methyl)acrylamide (13d)
(E)-3-(2,5-dimethoxyphenyl)-N-((1-(p-tolyl)-9H-pyrido[3,4-b]indol-3-yl)methyl)acrylamide (13e)
(E)-3-(4-chlorophenyl)-N-((1-(p-tolyl)-9H-pyrido[3,4-b]indol-3-yl)methyl) acrylamide (13f)
(E)-3-(4-hydroxy-3-methoxyphenyl)-N-((1-(p-tolyl)-9H-pyrido[3,4-b]indol-3-yl)methyl)acrylamide (13g)
(E)-3-(3-hydroxyphenyl)-N-((1-(p-tolyl)-9H-pyrido[3,4-b]indol-3-yl)methyl)acrylamide (13h)
(E)-N-((1-(p-tolyl)-9H-pyrido[3,4-b]indol-3-yl)methyl)-3-(3,4,5-trihydroxyphenyl)acrylamide (13i)
(E)-N-((1-(p-tolyl)-9H-pyrido[3,4-b]indol-3-yl)methyl)-3-(4-(trifluoromethyl)phenyl)acrylamide (13j)
(E)-3-(4-methoxyphenyl)-N-((1-(p-tolyl)-9H-pyrido[3,4-b]indol-3-yl)methyl)acrylamide (13k)
(E)-3-(4-aminophenyl)-N-((1-(p-tolyl)-9H-pyrido[3,4-b]indol-3-yl)methyl)acrylamide (13l)

DETAILED DESCRIPTION OF THE INVENTION

The invention will now be described in detail in connection with certain preferred and optional embodiments, so that various aspects thereof may be more fully understood and appreciated.

In the present invention it is proposed to incorporate 1-aryl-3-aminomethyl-β-carbolines with trans-cinnamic acids to provide N-((1-phenyl-9H-pyrido[3,4-b]indol-3-yl)methyl)cinnamamides. The molecules comprising of 1-aryl-3-aminomethyl-β-carboline and trans-cinnamic acid scaffolds within a single molecule could enhance the anticancer activity that might work through DNA intercalation.

The starting L-tryptophan (14), substituted benzaldehydes (16a-m) and substituted trans-cinnamic acids (22a-l) are commercially available and the N-((1-phenyl-9H-pyrido[3,4-b]indol-3-yl)methyl) cinnamamides 1a-l to 13a-l have been prepared as illustrated in the Scheme. 1.

i. the L-tryptophan methyl ester was prepared according to the following method. To the stirred solution of L-tryptophan (14, 0.1 mol) in methanol (50 ml), thionyl chloride (8.02 mL, 0.11 mol) was added drop-wise at 0° C. and continued stirring for 12 h at room temperature. The excess amount of solvent was removed under vacuum and dried well. Then, the resulting solid was dissolved in $CH_2Cl_2$, basified with saturated $NaHCO_3$ solution and extracted with excess amount of $CH_2Cl_2$. Then, the organic layer was dried over anhydrous sodium sulphate and concentrated under reduced pressure to obtain L-tryptophan methyl ester (15) as white solid.

ii. to the mixture of L-tryptophan ester (15, 0.023 mol) and appropriate benzaldeyde (16a-m, 0.023 mol) in ethanol (20 mL), catalytic amount of pTSA was added and the mixture was refluxed for 12 h. After completion of the reaction, ethanol was removed under vacuum and the obtained crude was dissolved in ethyl acetate (30 mL) and washed with saturated NaHCO₃ solution (20 mL) and water (20 mL) Then, the organic layer was dried over anhydrous sodium sulphate and concentrated under vacuum. Then, the resulting cyclic diastereomeric mixtures (17a-m) were used directly for next step without any further purification.

iii. the suspension of compounds 17a-m (0.025 mol) and sulphur (0.075 mol) in xylene (50 mL) was refluxed for 8.0 h. The reaction mixture was cooled to room temperature, diluted with n-hexane and stood at 4.0° C. for 3.0 h. The resulted precipitate was filtered, washed with hexane, dried and the obtained solid was re-crystallised by using ethyl acetate to afford products 18a-m.

iv. to a stirred suspension of compounds 18a-m (20 mmol) in dry THF (60 mL) was added LiBH₄ (22 mmol) at 0° C. and stirred for 4 h at room temperature. After completion of the reaction, quenched with saturated NH₄Cl solution (50 mL) and extracted with ethyl acetate (100 mL) and washed with water (50 mL). The organic layer was dried over anhydrous sodium sulphate, evaporated under reduced pressure and the crude products (19a-m) were used directly for the next step without any further purification.

v. to a stirred solution of 19a-m (10 mmol) in dry THF (50 ml) was added DBU (15 mmol) and DPPA (12 mmol) at 0° C. The reaction mixture was stirred for 16 h at rt and the reaction mixture was quenched with water, extracted with ethyl acetate and washed with water. The combined organic phases were dried over sodium sulphate, concentrated under reduced pressure and purified by column chromatography using silica gel to get pure compounds 20a-m.

vi. to a stirred solution of azide compounds 20a-m (1 mmol) in acetonitrile and water (1:1, 40 mL)) was added tripthenylphosphene (1.1 mmol) and stirred for 12 h at rt. The solvent was removed in vacuo, added 6N HCl solution and washed with ethyl acetate (2×20 mL) and the aqueous acidic medium and basified with 20% NaOH solution (up to pH=10), extracted with chloroform, washed with water, dried over sodium sulphate and concentrated under reduced pressure to get crude products which were triturated in 10% ethyl acetate/hexane, decanted and dried to get pure amine products (21a-m).

vii. to a stirred solution of required amines (21a-m, 1 mmol)) and appropriate cinnamic acids (22a-l, 1.1 mmol) in DCM (10 mL) was added HBTU (1.3 mmol), TEA (3 mmol) and stirred for 12 h. After completion of the reaction quenched with ice cold water (20 mL), extracted with DCM (2×20 mL), washed with water (20 mL), dried over sodium sulphate and concentrated in vacuo. The crude products were purified by column chromatography using ethyl acetate and n-hexane as eluting solvents to get pure products N-((1-phenyl-9H-pyrido[3,4-b]indol-3-yl)methyl)cinnamamides 1a-l to 13a-l.

All the new N-((1-phenyl-9H-pyrido[3,4-b]indol-3-yl)methyl)cinnamamides were synthesized and purified by column chromatography using different solvents like ethyl acetate and hexane.

i. These new N-((1-phenyl-9H-pyrido[3,4-b]indol-3-yl)methyl)cinnamamides have shown promising anticancer activity in various cancer cell lines.

Scheme 1. Synthesis of N-((1-phenyl-9H-pyrido[3,4-b]indol-3-yl)methyl)cinnamamides.

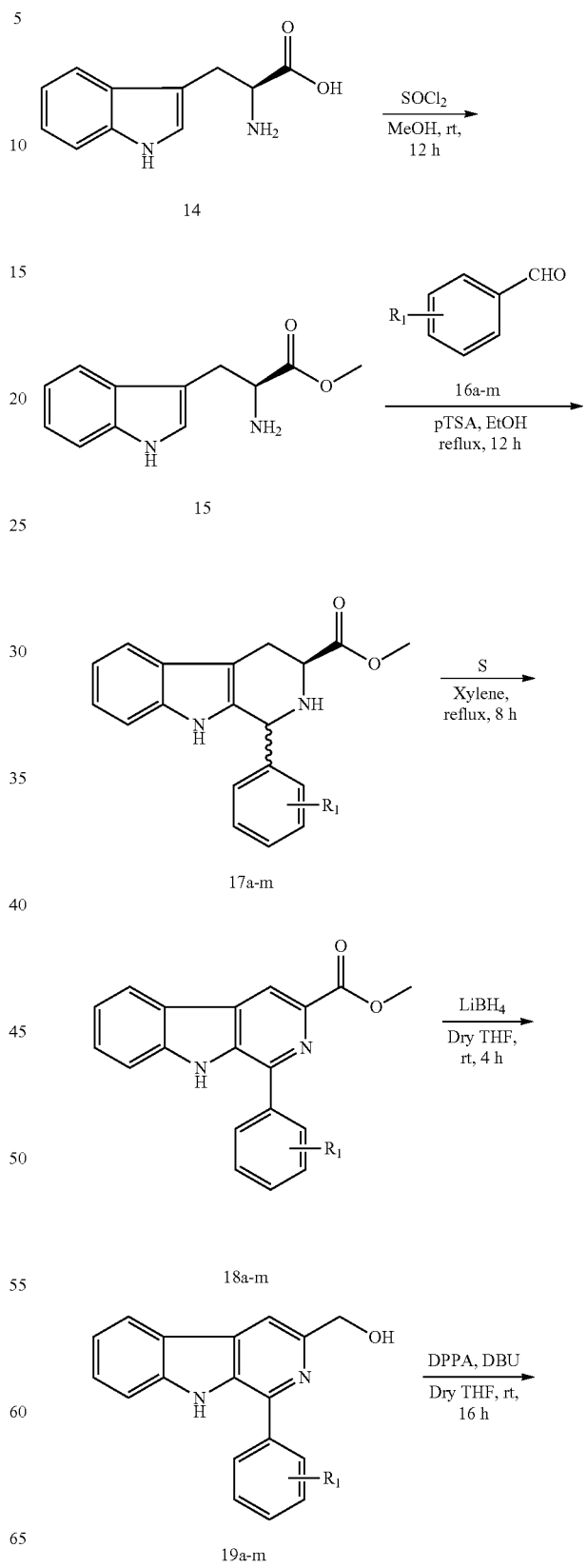

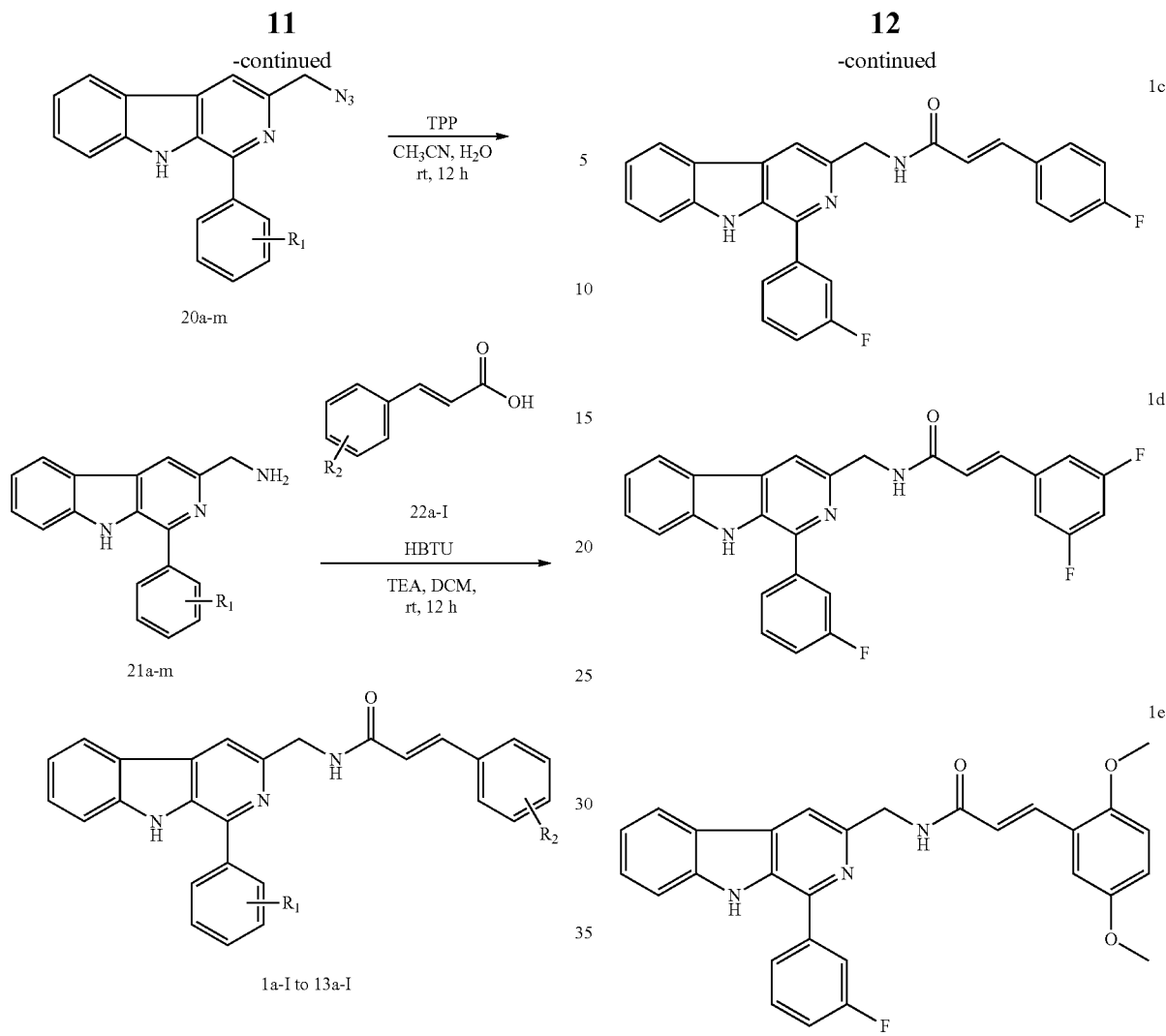
The structural formulae of the representative compounds are:
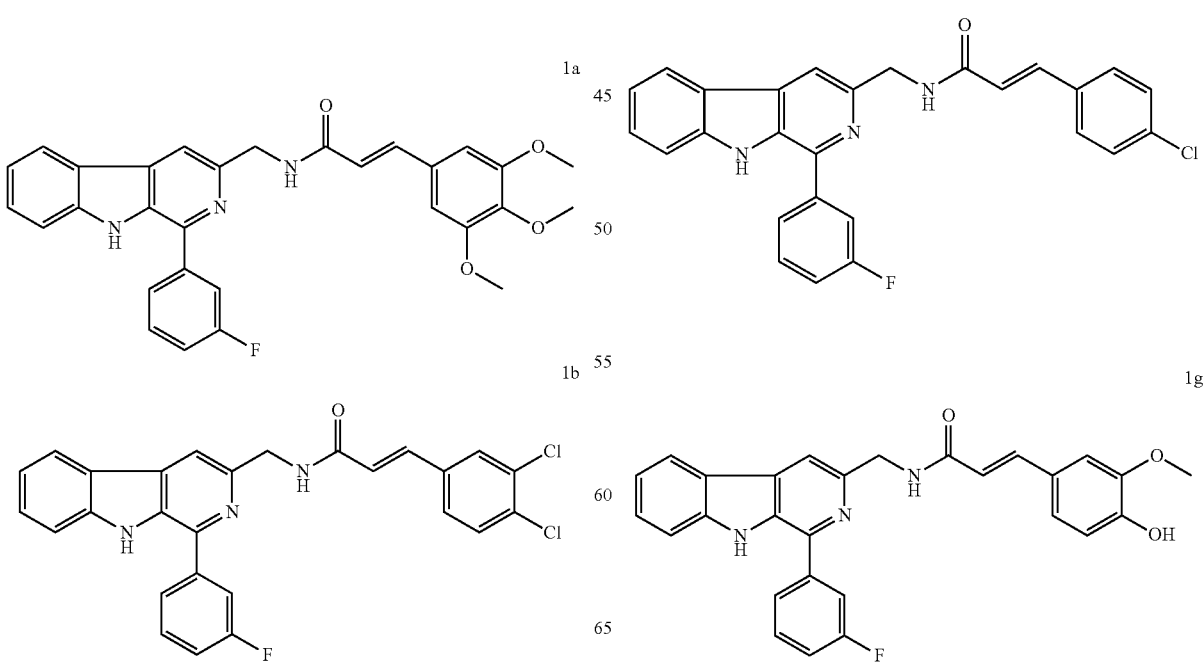

-continued
1h
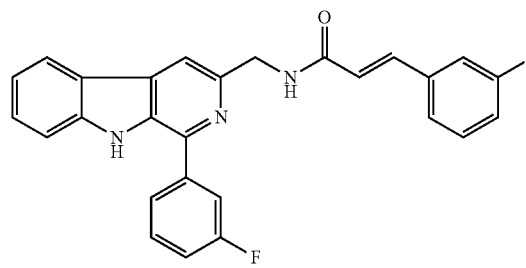
2a
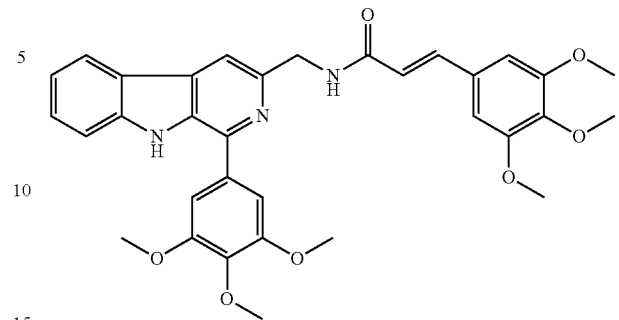
1i
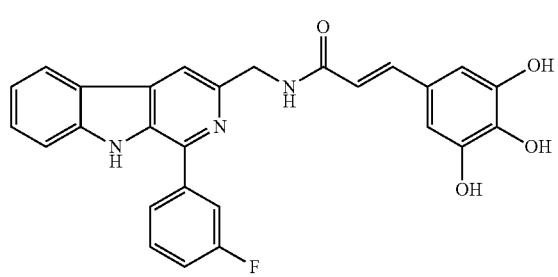
2b
1j
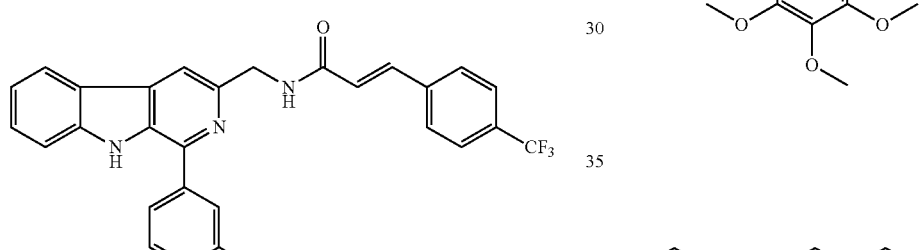
2c
1k
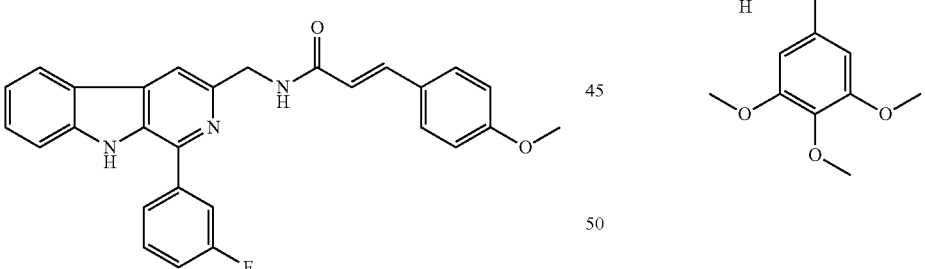
2d
1l
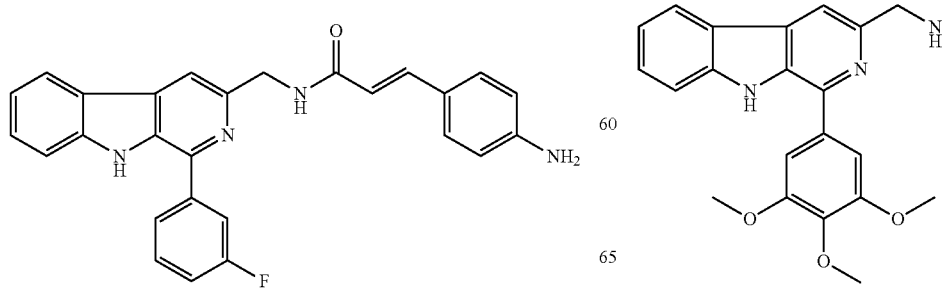

2e
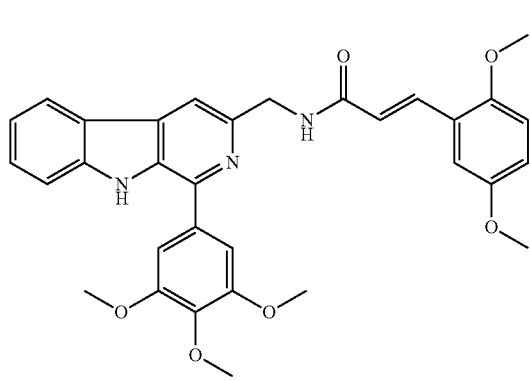
2i
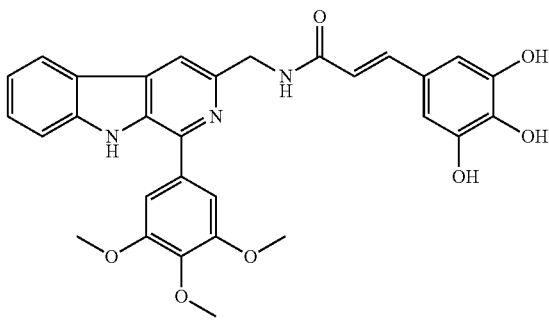
2f
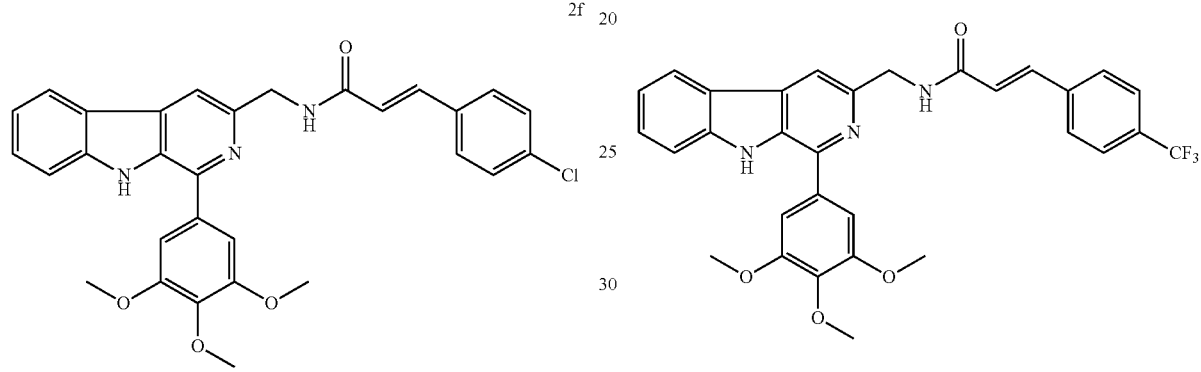
2j
2g
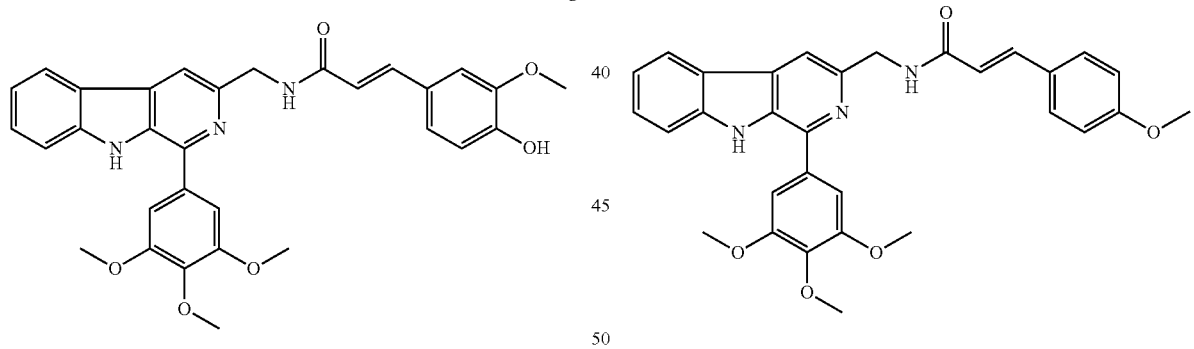
2k
2h
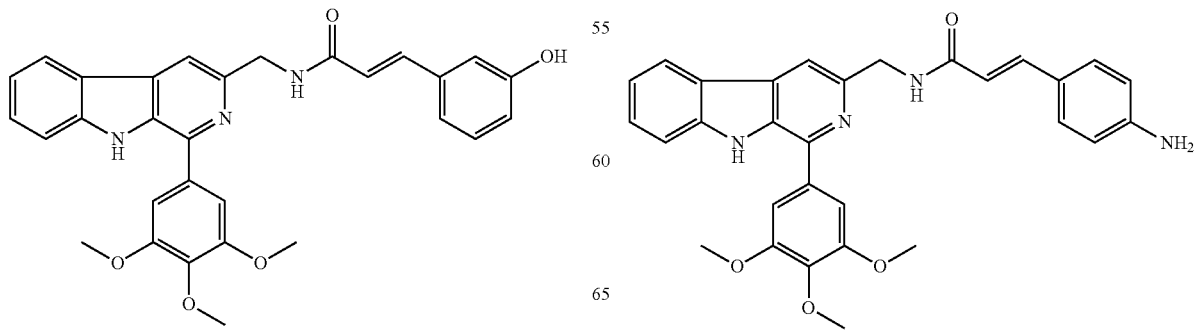
2l

3a 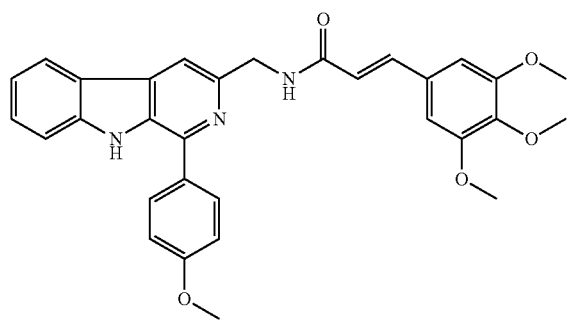
3b 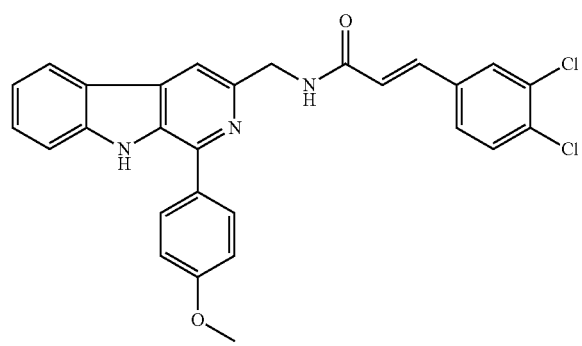
3c 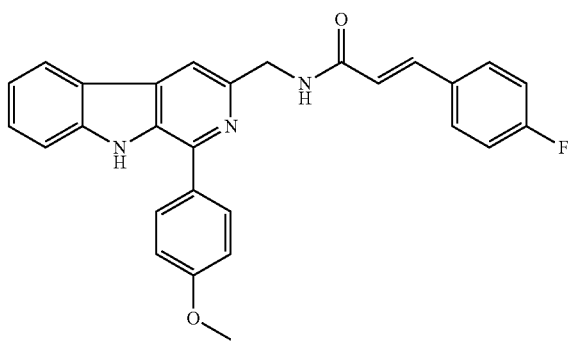
3d 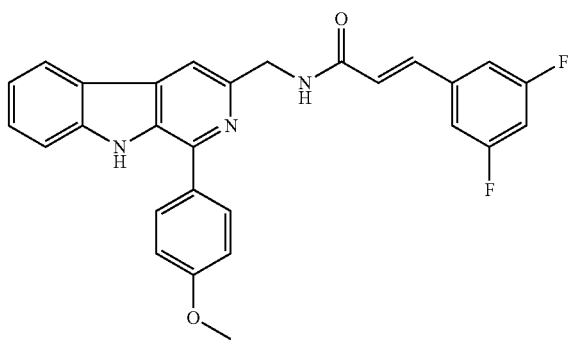
3e 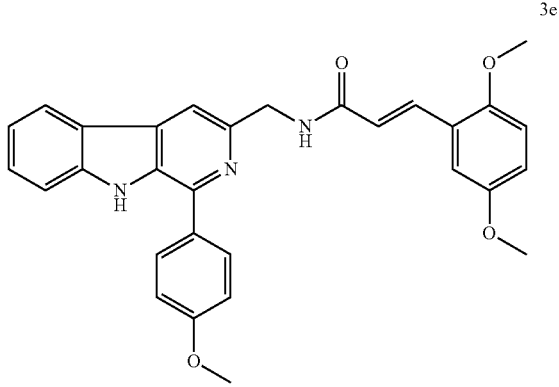
3f 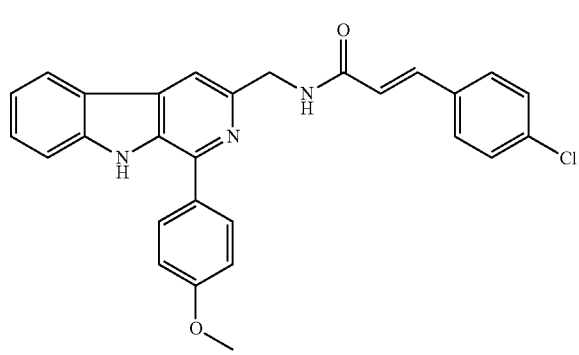
3g 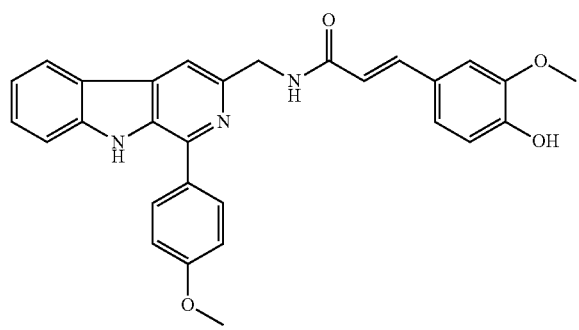
3h 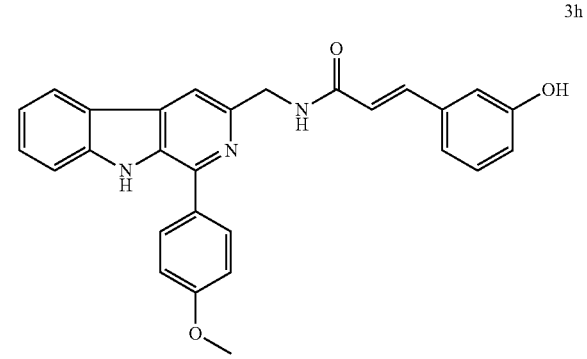

-continued
3i
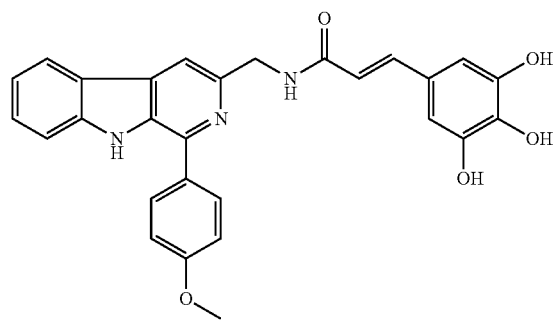
3j
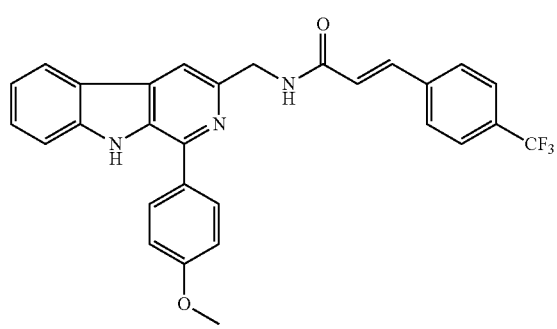
3k
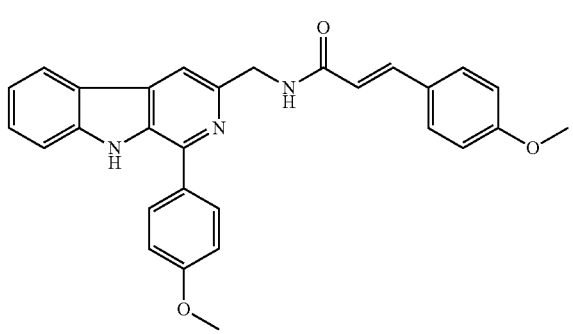
3l
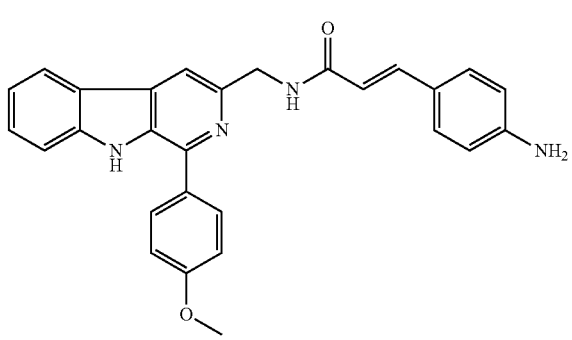
4a
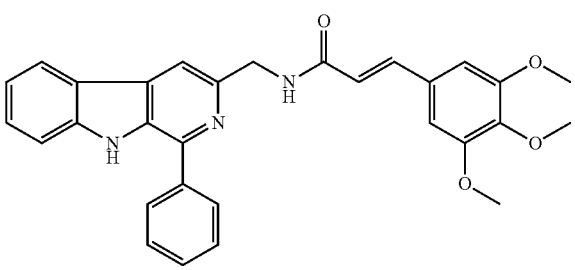
-continued
4b
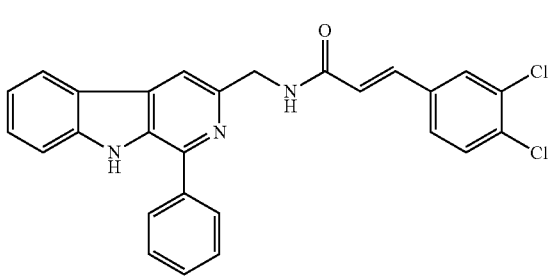
4c
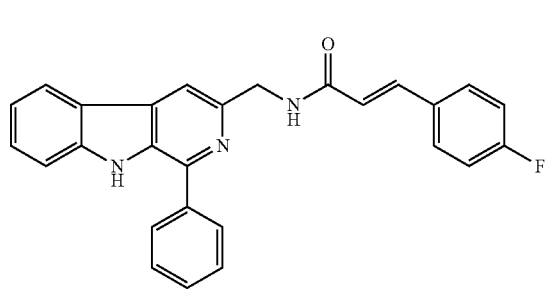
4d
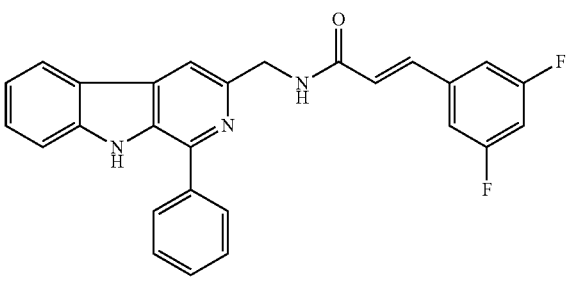
4e
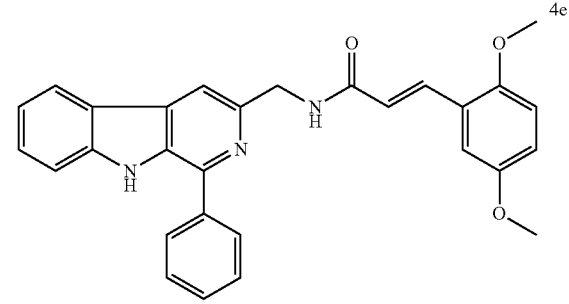
4f
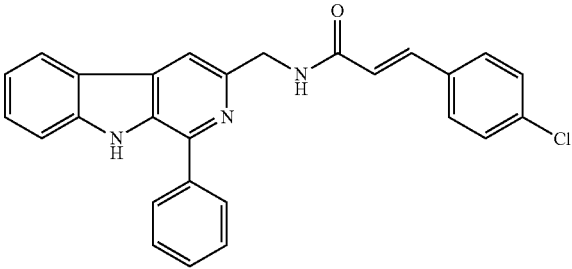

-continued
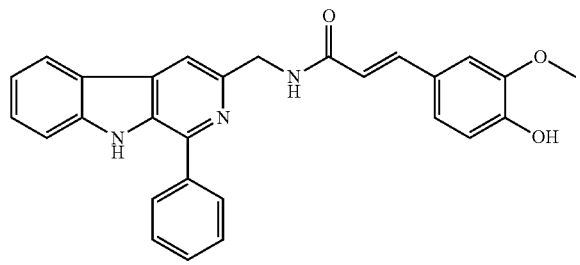
4g
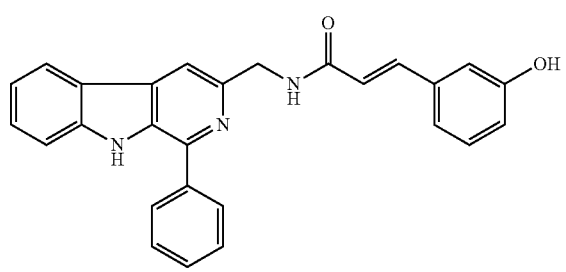
4h
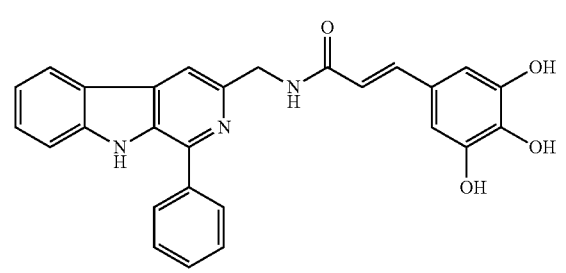
4i
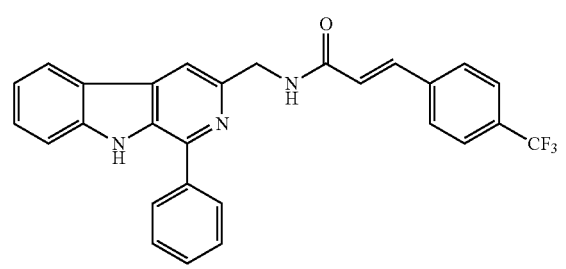
4j
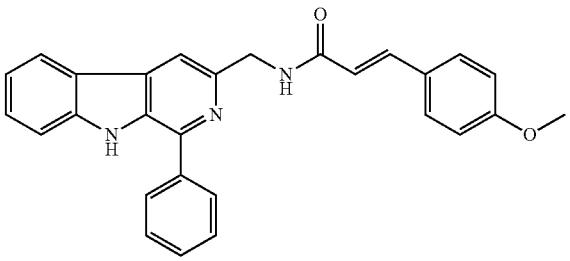
4k
-continued
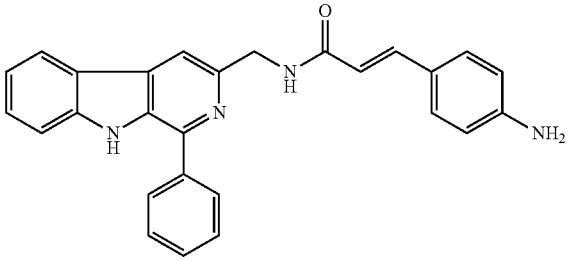
4l
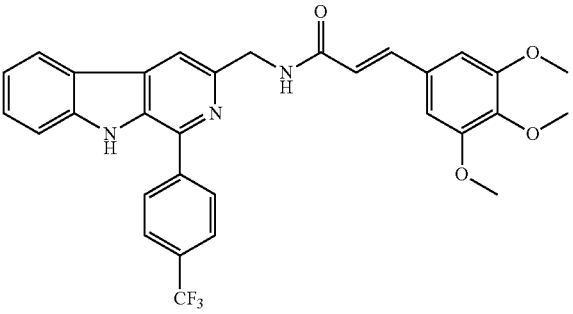
5a
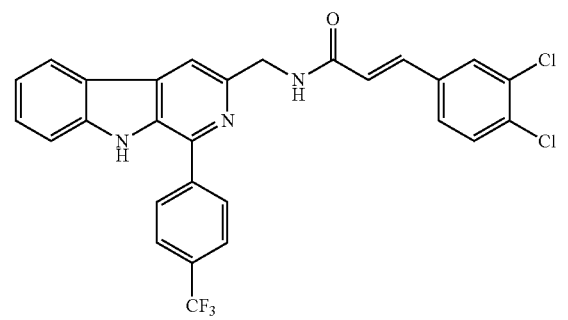
5b
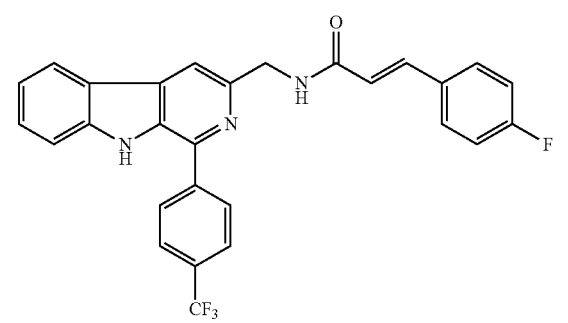
5c
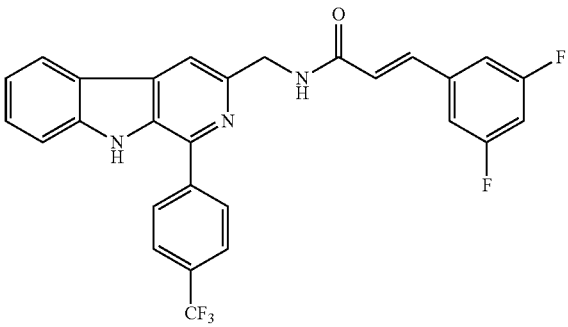
5d 5e
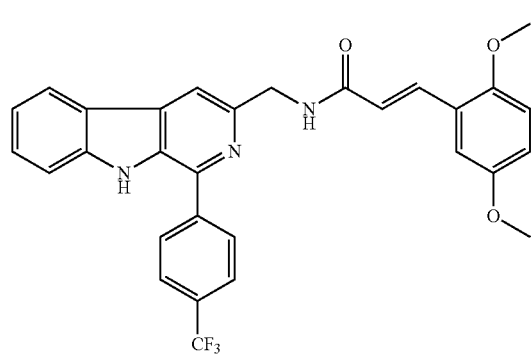
5k
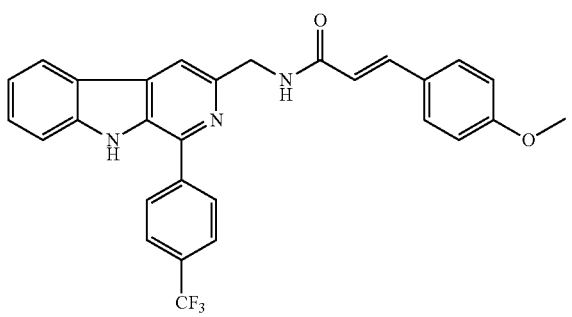
5f
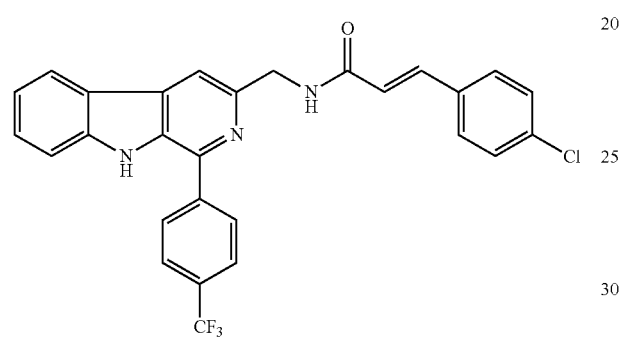
5l
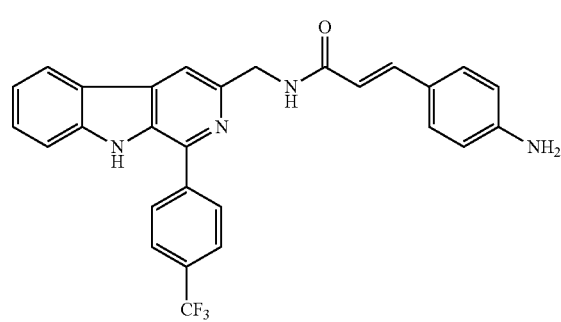
5g
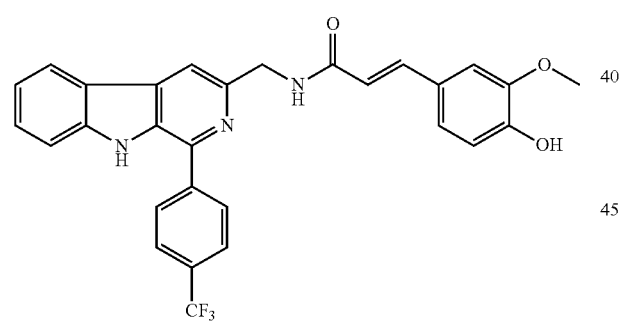
5i
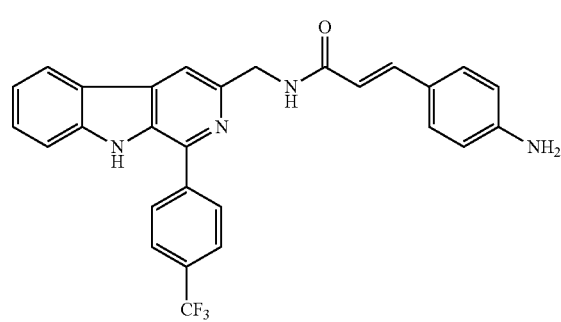
5h
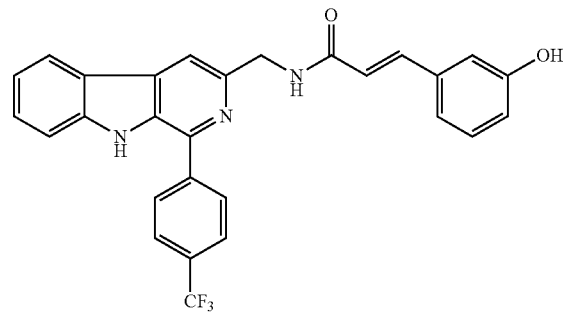
5j
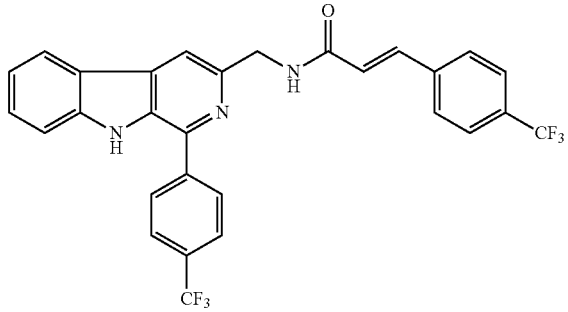

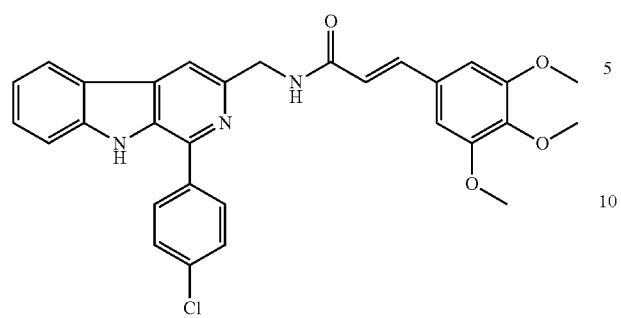
6a
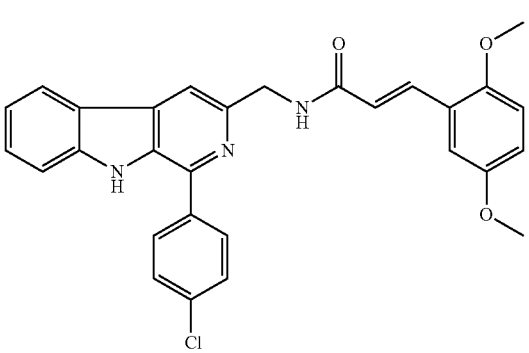
6e
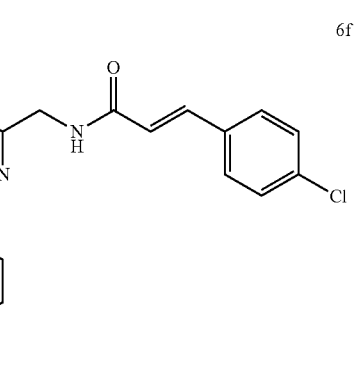
6b
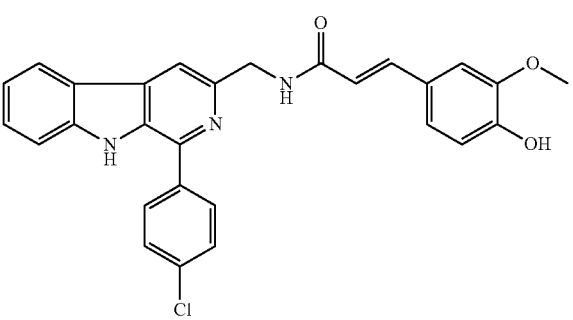
6f
6c
6g
6d
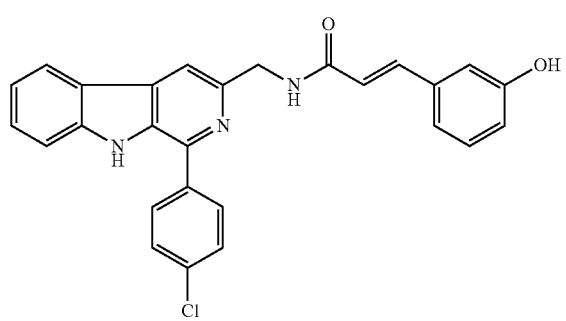
6h

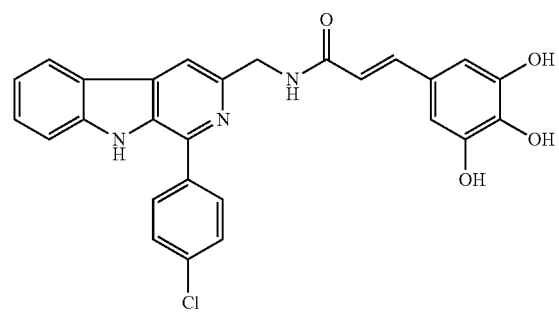
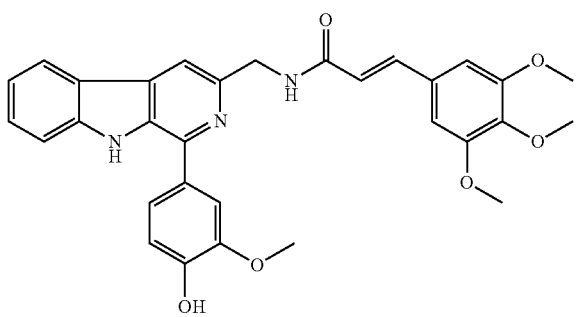
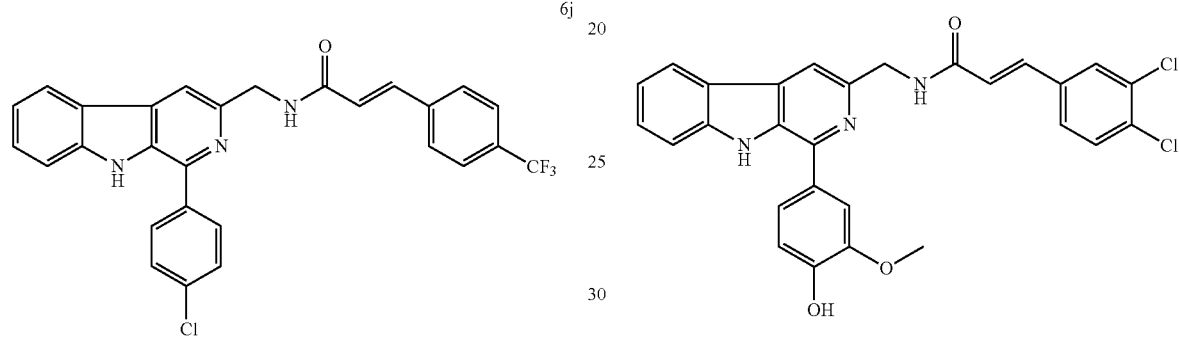
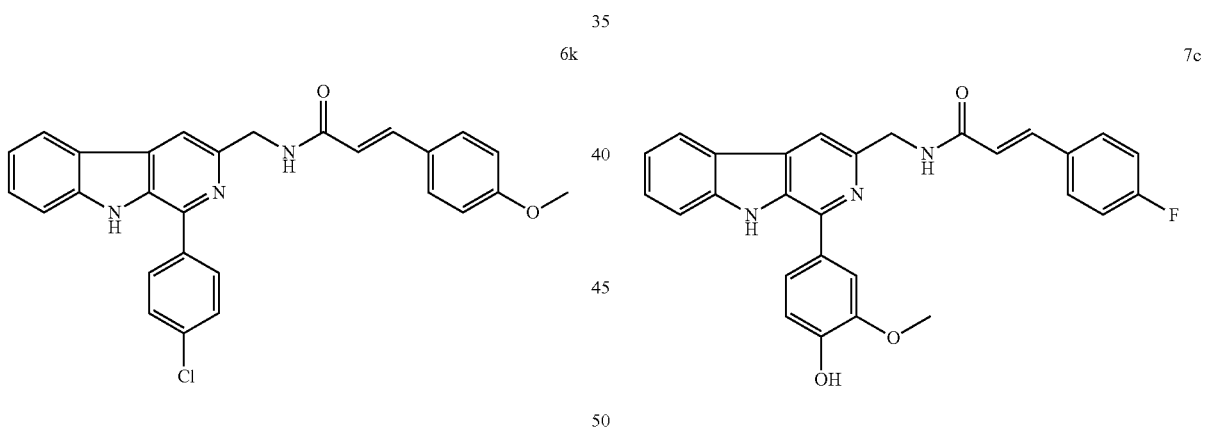
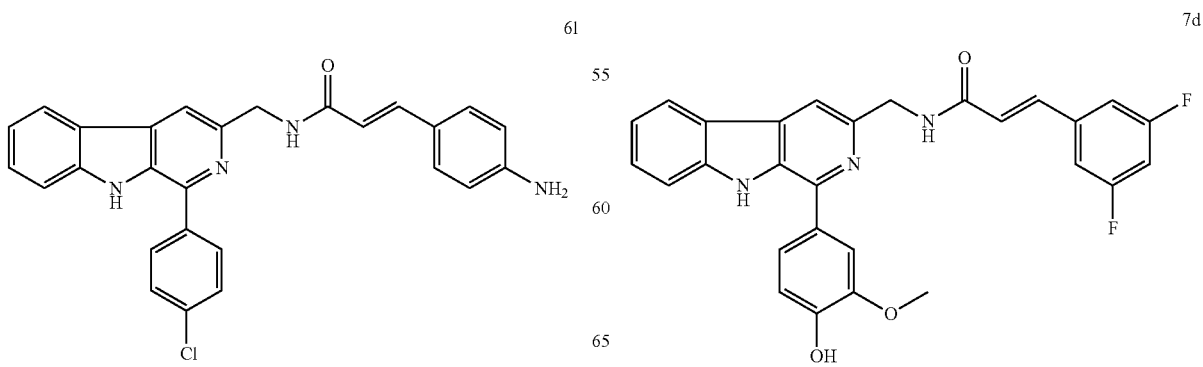

7e
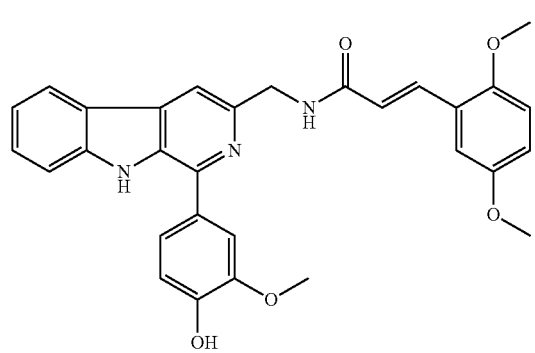
7i
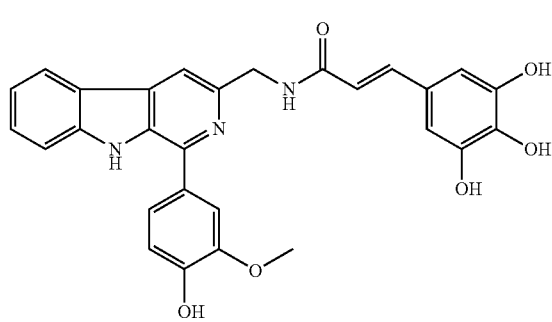
7f
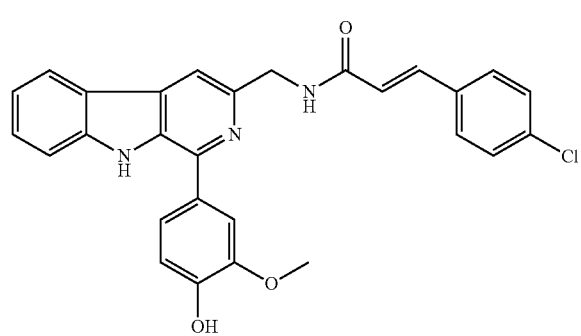
7j
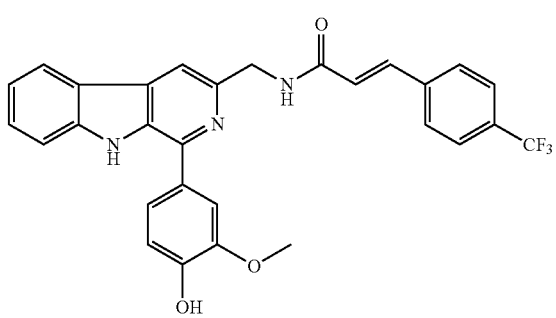
7g
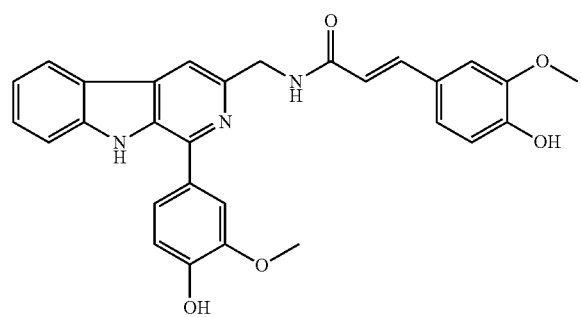
7k
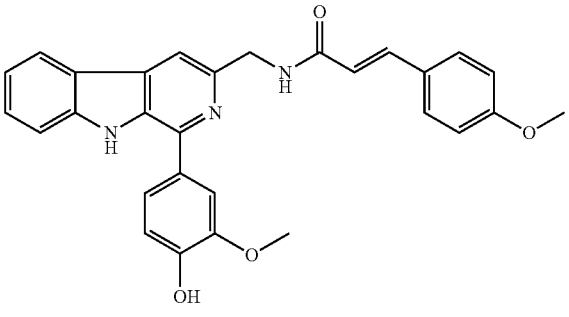
7h
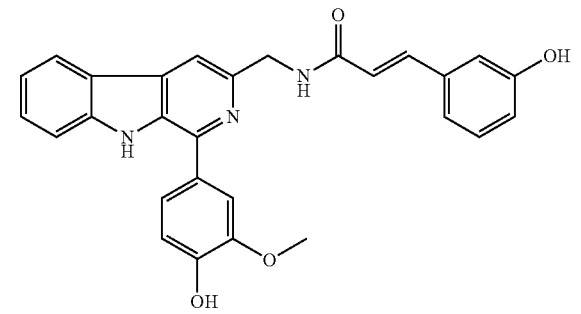
7l
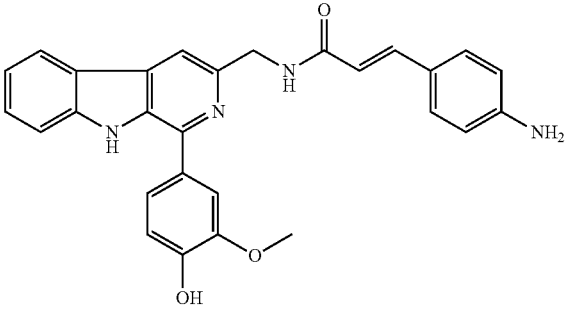

-continued
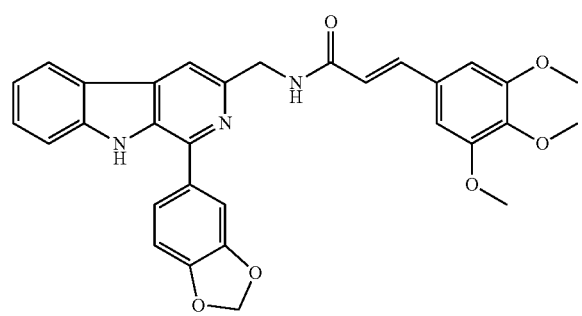
8a
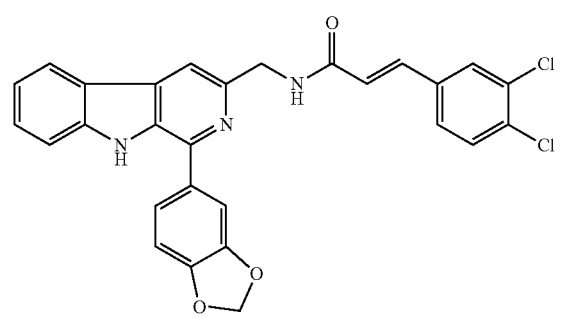
8b
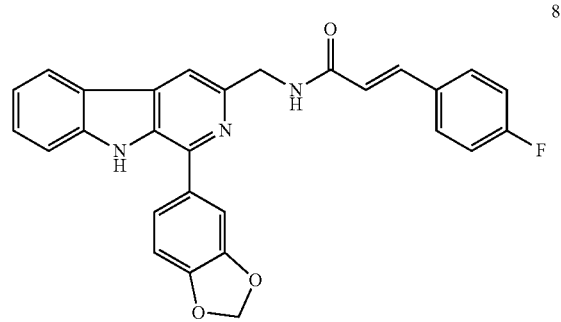
8c
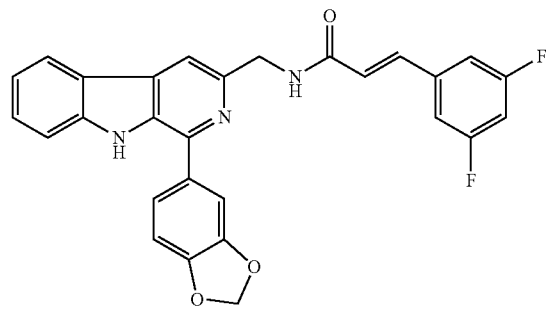
8d
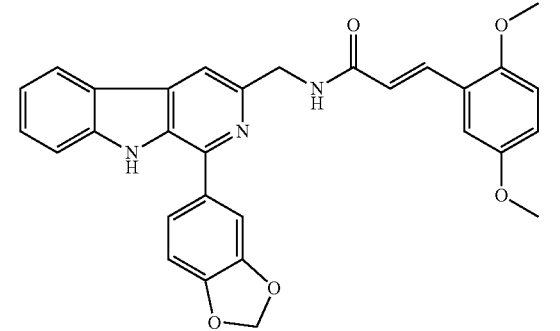
8e
-continued
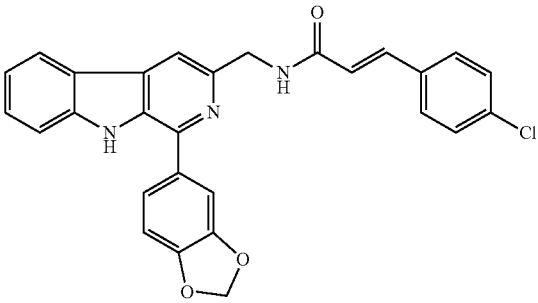
8f
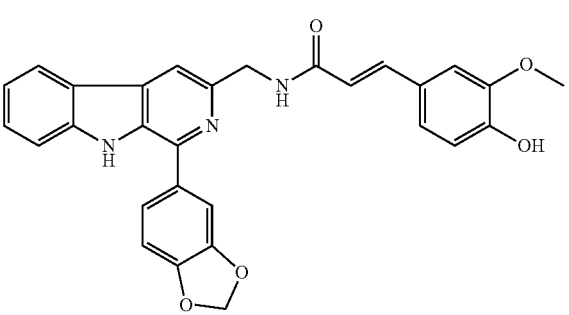
8g
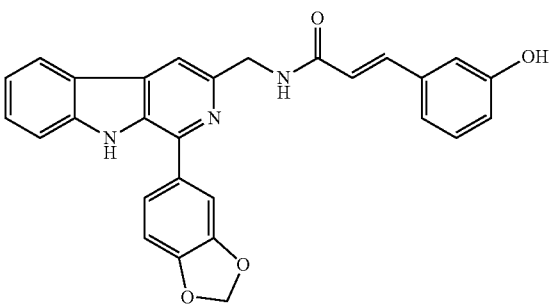
8h
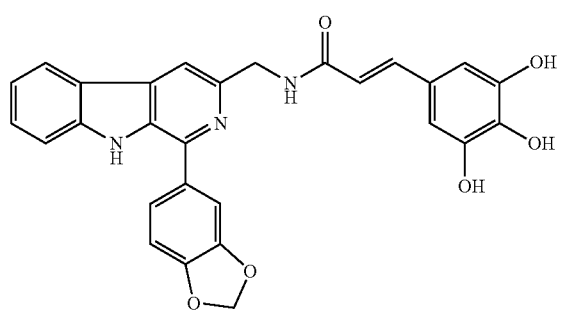
8i
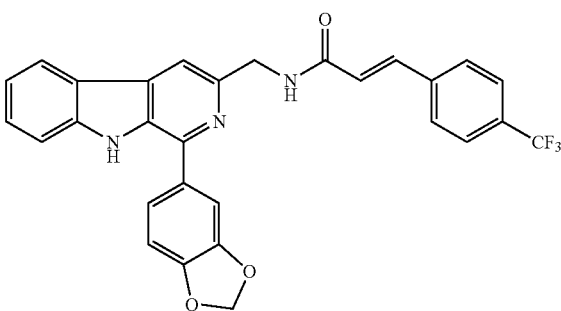
8j 8k
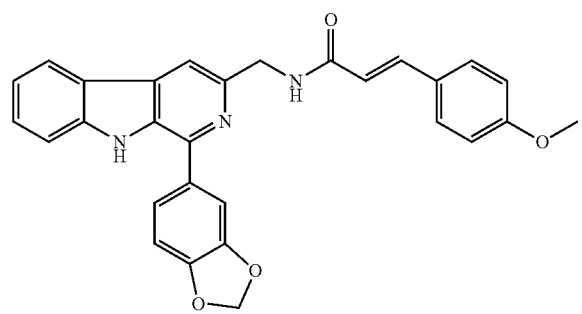
8l
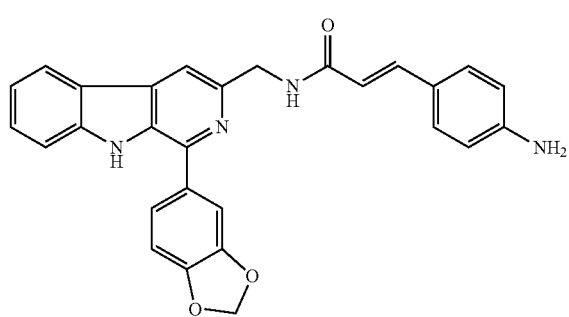
9a
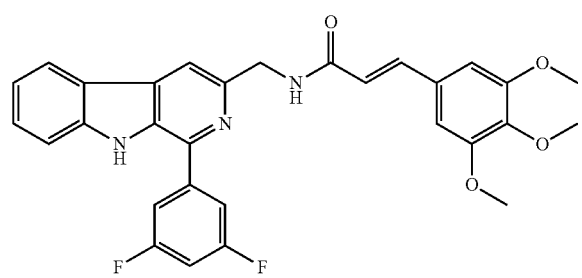
9b
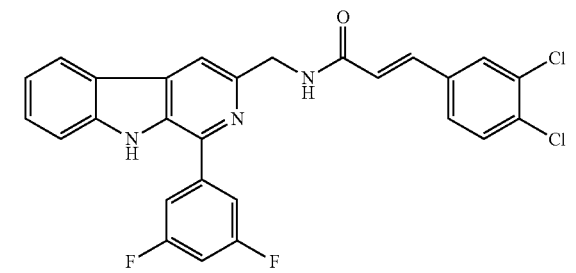
9c
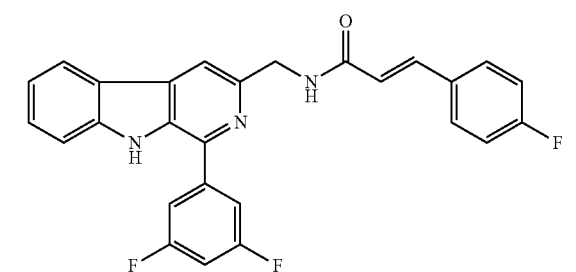
9d
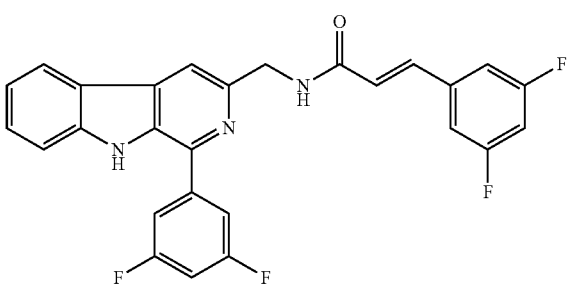
9e
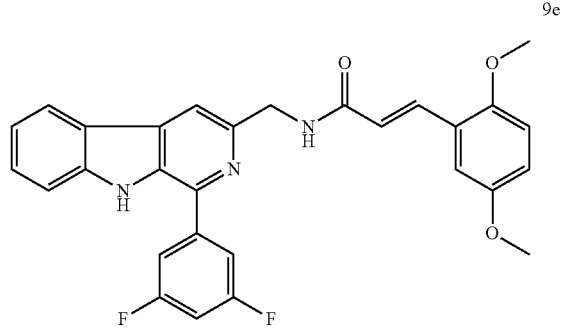
9f
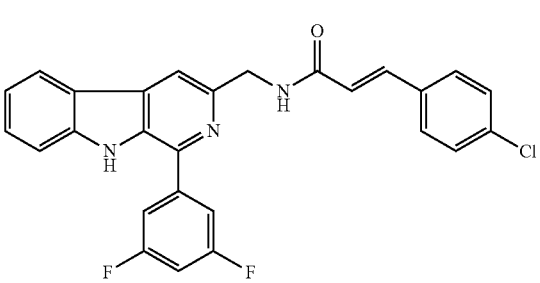
9g
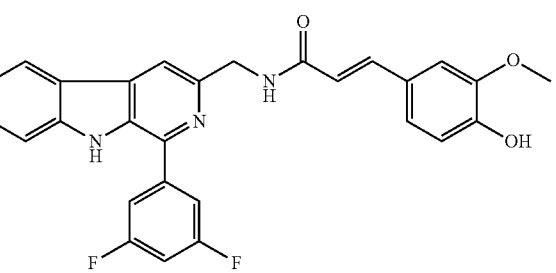
9h
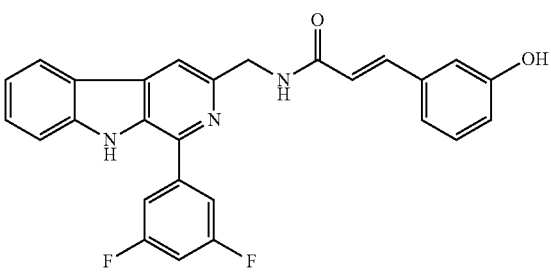

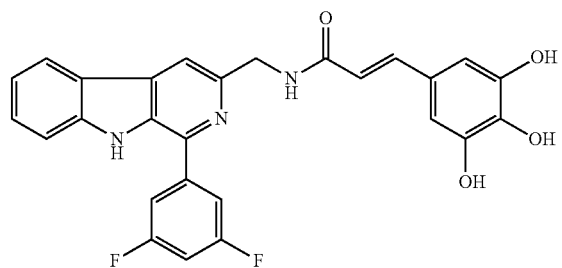
9i
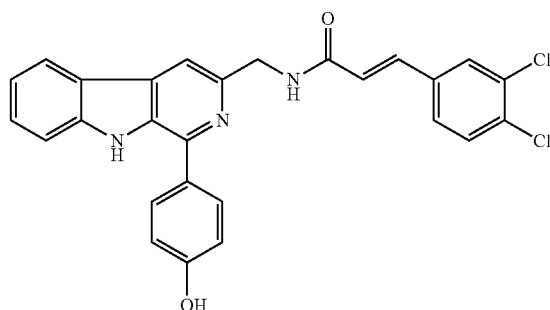
10b
9j
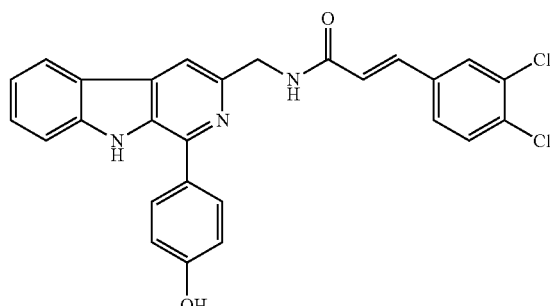
10c
9k
9l
10a
10d
10e

-continued
10f
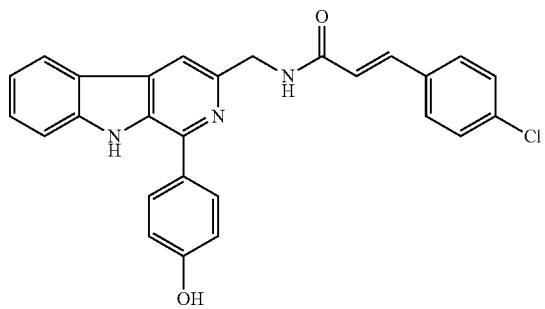
10g
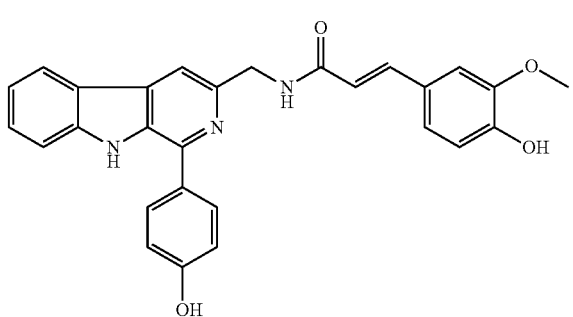
10h
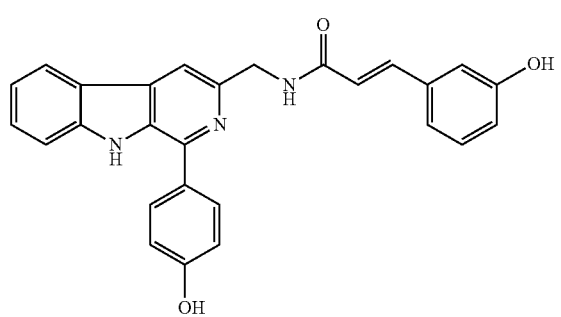
10i
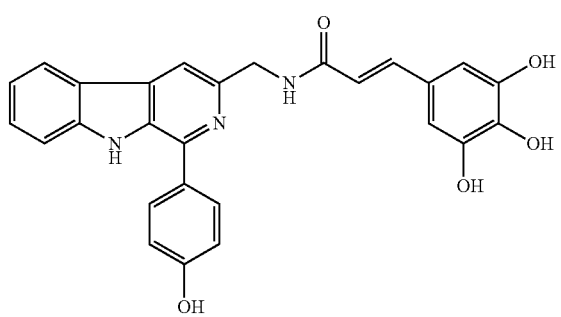
-continued
10j
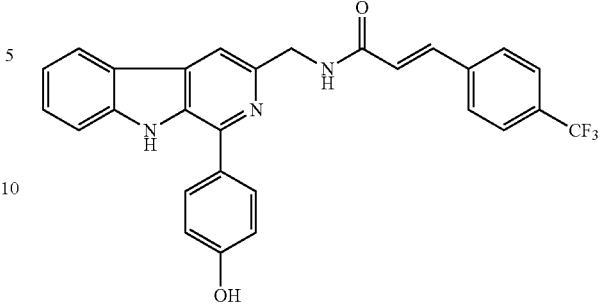
10k
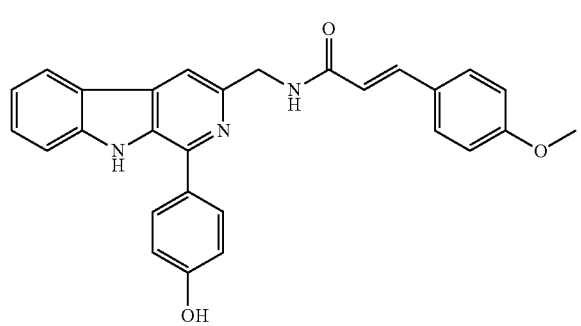
10l
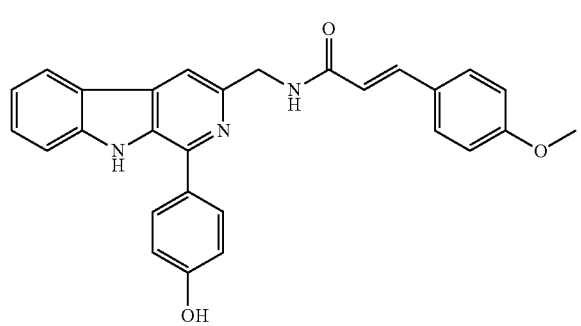
11a
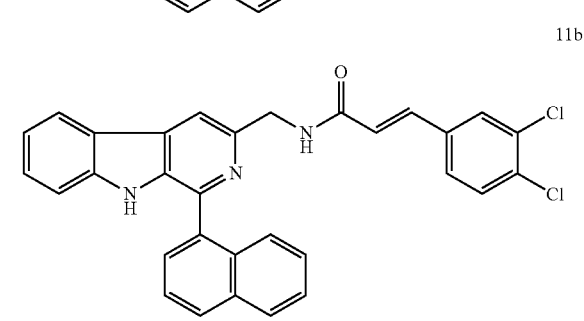
11b
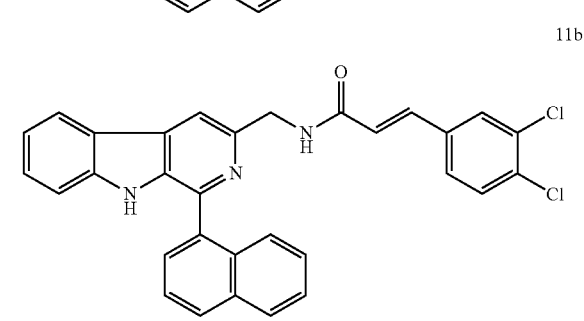

11c
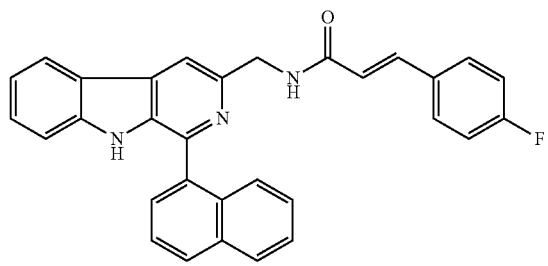
11d
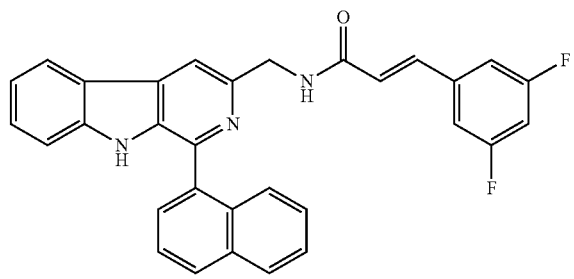
11e
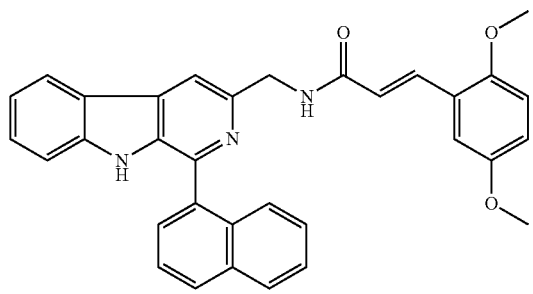
11f
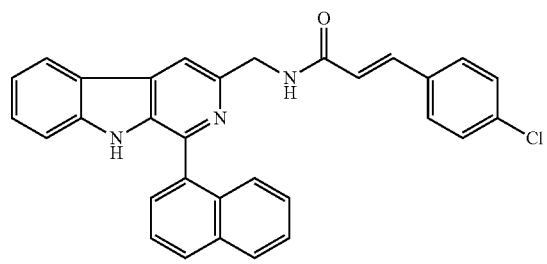
11g
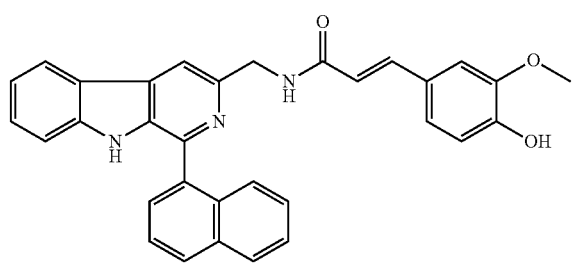
11h
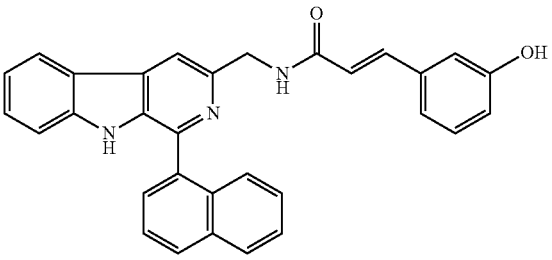
11i
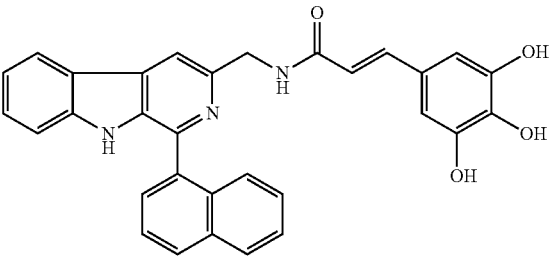
11j
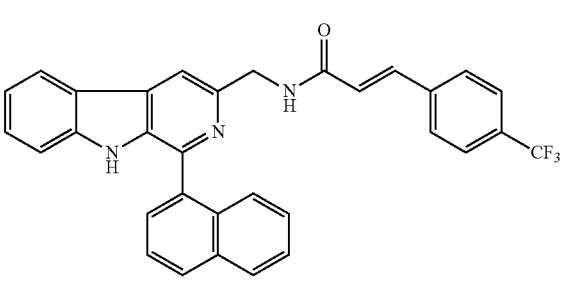
11k
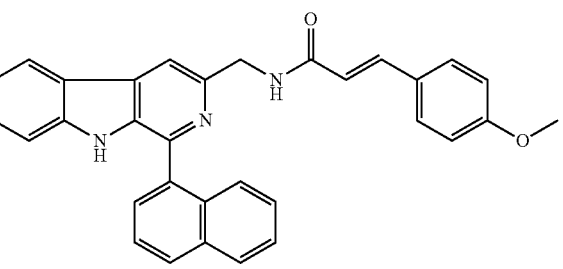
11l
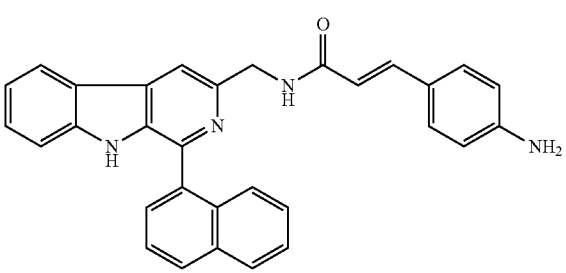

12a
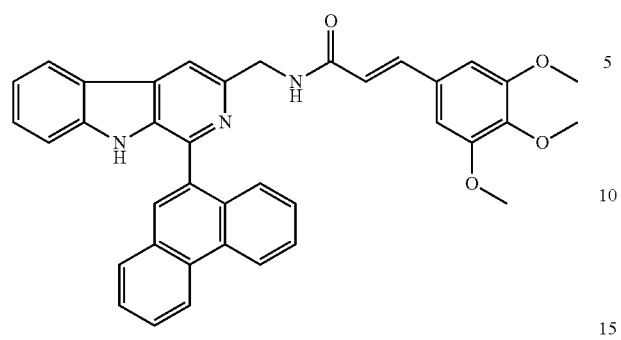
12b
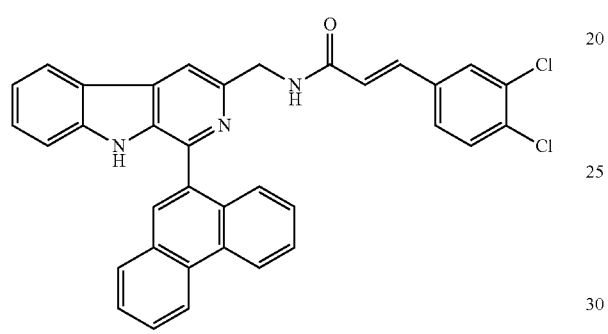
12c
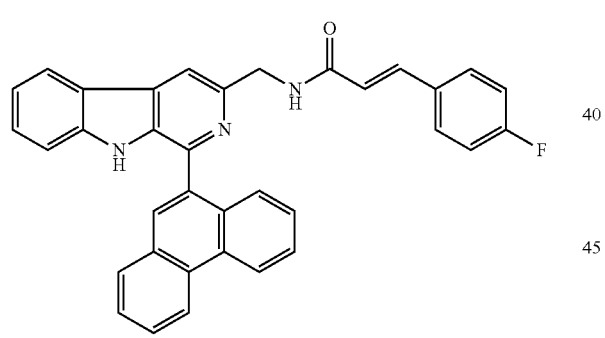
12d
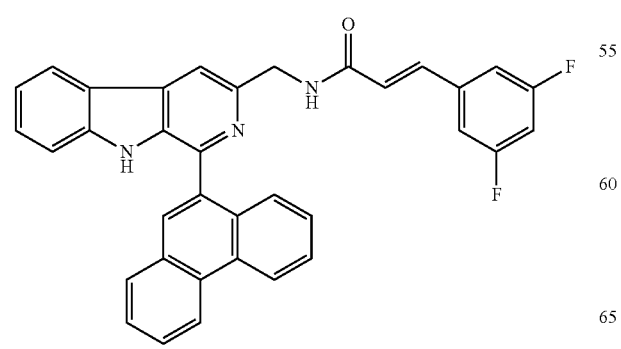
12e
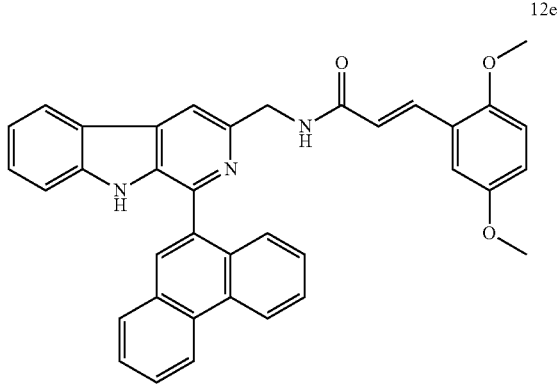
12f
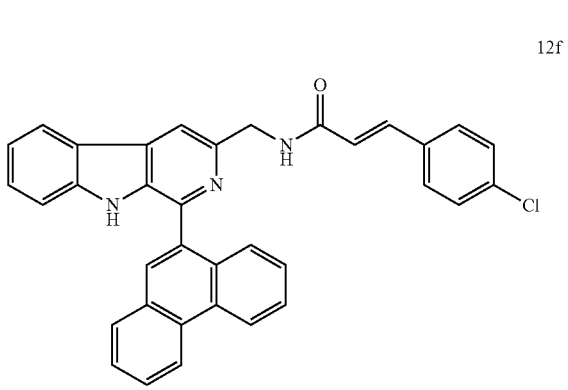
12g
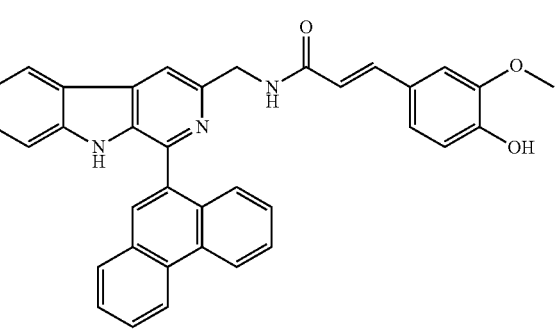
12h
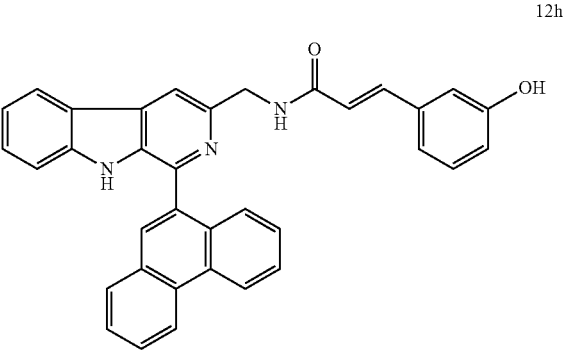

12i
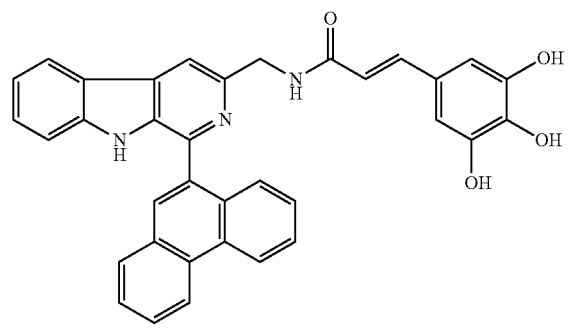
13a
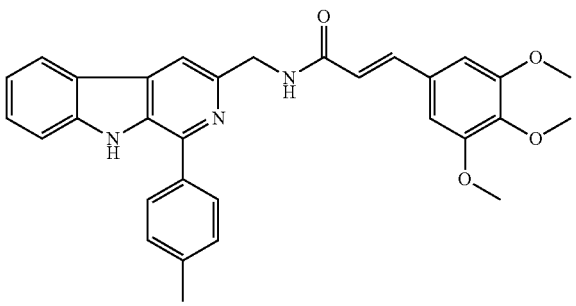
12j
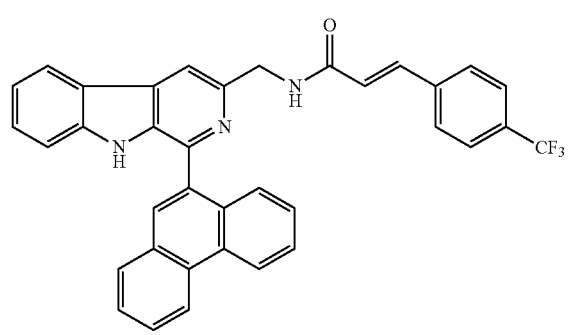
13b
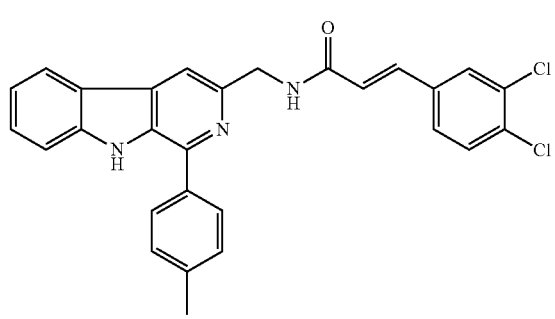
12k
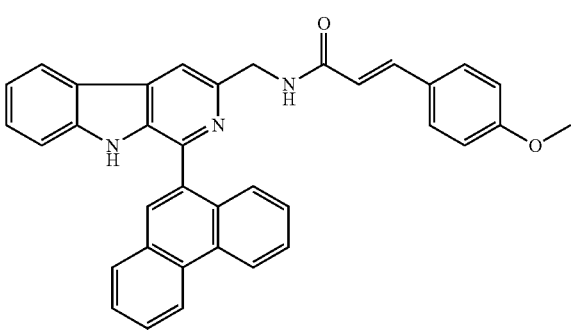
13c
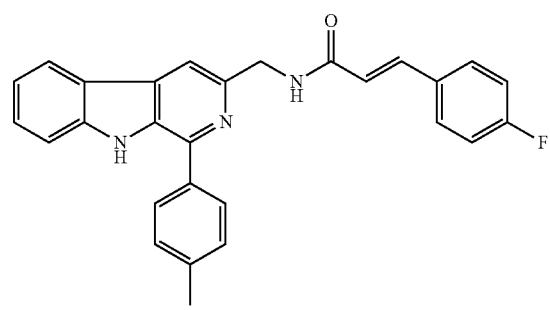
12l
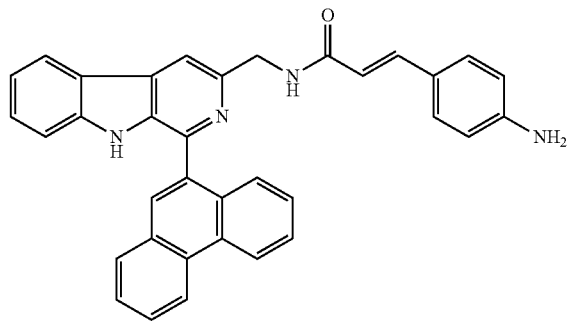
13d
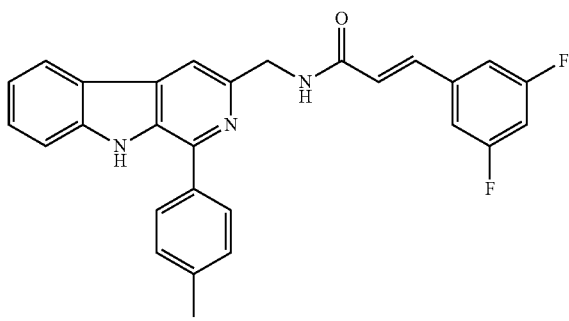

13e
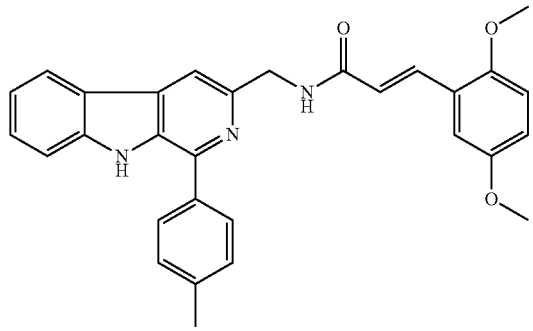

13j
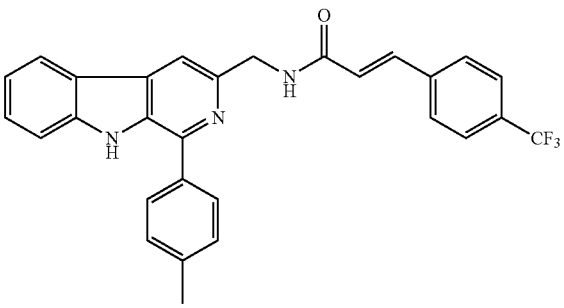

13f
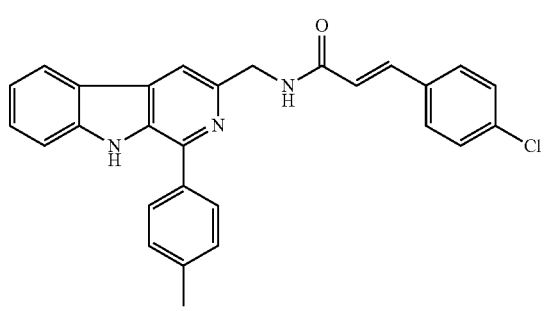

13k
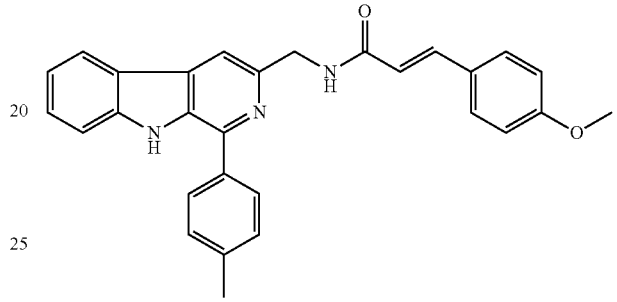

13g
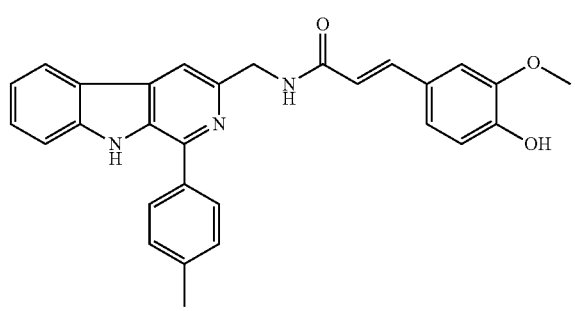

13l
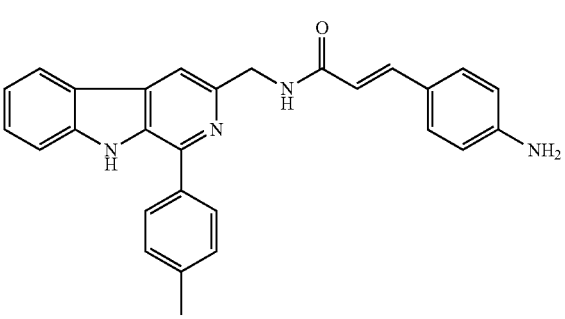

13h
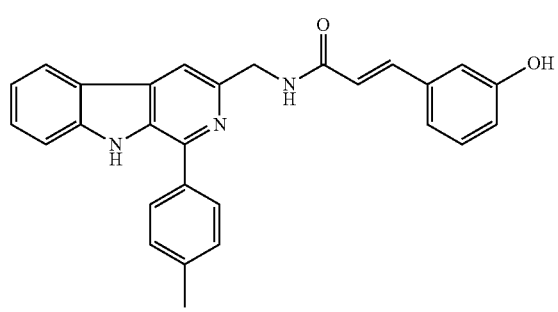

13i
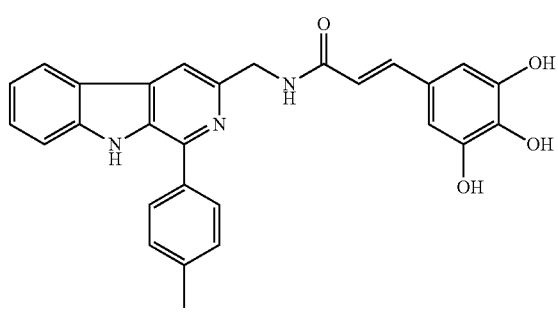

EXAMPLES

The following examples are given by way of illustration of the working of the invention in actual practice and therefore should not be construed to limit the scope of present invention.

Example 1

(E)-N-((1-(3-fluorophenyl)-9H-pyrido[3,4-b]indol-3-yl)methyl)-3-(3,4,5-trimethoxyphenyl)acrylamide
(1a)

To a solution of (1-(3-fluorophenyl)-9H-pyrido[3,4-b]indol-3-yl)methanamine (21a, 100 mg, 0.34 mmol) and (E)-3-(3,4,5-trimethoxyphenyl)acrylic acid (22a, 81 mg, 0.34 mmol) in dry DMF (10 mL) was added HBTU (156 mg, 0.41 mmol) and triethylamine (0.14 mL, 1.03 mmol) under nitrogen atmosphere and the reaction mixture was stirred at 35° C. for 12 h. After the complete consumption of starting materials (monitored by TLC), the contents of the reaction were cooled to room 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-25%), collected fractions and evaporated in vacuo to afford 1a as yellow solid 149 mg (85% yield); mp: 148-150° C.; $^1$H NMR (300 MHz, CDCl$_3$+DMSO-d$_6$): δ (ppm) 10.90 (s, 1H), 8.15-8.08 (m, 1H), 8.02-7.77 (m, 4H), 7.65-7.43 (m, 4H), 7.29-7.16 (m, 2H), 6.80 (s, 2H), 6.64 (d, J=15.6 Hz, 1H), 4.88 (d, J=5.4 Hz, 2H), 3.89 (s, 6H), 3.84 (s, 3H); $^{13}$C NMR (125 MHz, CDCl$_3$+DMSO-d$_6$): δ (ppm): 165.66, 163.84, 161.90, 153.49, 147.47, 142.07, 140.99, 140.00, 139.51, 139.11, 132.55, 131.09, 130.90, 128.71, 124.92, 122.06, 121.93, 121.15, 119.97, 115.79, 112.86, 112.23, 107.96, 105.37, 60.52, 56.29, 45.27; MS-ESI: m/z 512 [M+H]$^+$; HRMS (ESI): calcd for C$_{30}$H$_{27}$O$_4$N$_3$F m/z 512.19618 [M+H]$^+$; found 512.19801.

Example 2

(E)-3-(3,4-dichlorophenyl)-N-((1-(3-fluorophenyl)-9H-pyrido[3,4-b]indol-3-yl)methyl)acrylamide (1b)

To a solution of (1-(3-fluorophenyl)-9H-pyrido[3,4-b]indol-3-yl)methanamine (21a, 100 mg, 0.34 mmol) and (E)-3-(3,4-dichlorophenyl)acrylic acid (22b, 74 mg, 0.34 mmol) in dry DMF (10 mL) was added HBTU (156 mg, 0.41 mmol) and triethylamine (0.14 mL, 1.03 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-20%), collected fractions and evaporated in vacuo to afford 1b as yellow solid 118 mg (70% yield); mp: 255-258° C.; $^1$H NMR (500 MHz, DMSO-d$_6$) δ (ppm): 11.56 (s, 0.7H), 8.76 (s, 1H), 8.26 (d, J=7.6 Hz, 0.7H), 8.10 (s, 0.7H), 7.94-7.81 (m, 3H), 7.70-7.62 (m, 3H), 7.61-7.53 (m, 2H), 7.49 (d, J=15.8 Hz, 1H), 7.40-7.34 (m, 1H), 7.25 (t, J=7.0 Hz, 1H), 6.89 (d, J=15.7 Hz, 1H), 4.72 (s, 2H), peaks at 11.70, 8.43 and 8.17 are due to the 30% minor rotamer; $^{13}$C NMR (125 MHz, DMSO-d$_6$) δ (ppm): 141.0, 140.9, 136.7, 136.4, 133.0, 132.5, 131.1, 132.0, 131.5, 130.9, 129.9, 128.8, 127.7, 125.0, 124.9, 124.3, 122.4, 122.1, 121.7, 121.1, 120.0, 115.6, 115.4, 114.3, 112.9, 112.4, 45.2; MS-ESI: m/z 490 [M+H]$^+$; HRMS (ESI): calcd for C$_{27}$H$_{19}$FN$_3$O$_2$Cl$_2$ m/z 490.08687 [M+H]$^+$; found 490.08731.

Example 3

(E)-3-(4-fluorophenyl)-N-((1-(3-fluorophenyl)-9H-pyrido[3,4-b]indol-3-yl)methyl)acrylamide (1c)

To a solution of (1-(3-fluorophenyl)-9H-pyrido[3,4-b]indol-3-yl)methanamine (21a, 100 mg, 0.34 mmol) and (E)-3-(4-fluorophenyl)acrylic acid (22c, 57 mg, 0.34 mmol) in dry DMF (10 mL) was added HBTU (156 mg, 0.41 mmol) and triethylamine (0.14 mL, 1.03 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-30%), collected fractions and evaporated in vacuo to afford 1c as pale yellow solid 109 mg (73% yield); mp: 258-264° C. $^1$H NMR (500 MHz, DMSO-d$_6$) δ (ppm): 11.56 (s, 0.7H), 8.74 (s, 1H), 8.27 (d, J=7.7 Hz, 0.7H), 8.10 (s, 0.07H), 7.94-7.88 (m, 1H), 7.87-7.82 (m, 1H), 7.69-7.62 (m, 4H), 7.58-7.49 (m, 2H), 7.39-7.34 (m, 1H), 7.29-7.23 (m, 3H), 6.77 (d, J=15.7 Hz, 1H), 4.72 (d, J=4.8 Hz, 2H), peaks at 11.70, 8.44 and 8.16 are due to 30% minor rotamer; $^{13}$C NMR (125 MHz, DMSO-d$_6$) δ (ppm): 165.4, 164.1, 163.8, 162.1, 161.9, 147.4, 142.0, 140.0, 138.1, 131.1, 130.9, 130.1, 130.2, 128.8, 124.9, 122.6, 122.1, 121.8, 115.6, 114.4, 112.9, 112.7, 112.4, 45.2; MS-ESI: m/z 440 [M+H]$^+$; HRMS (ESI): calcd for C$_{27}$H$_{20}$ON$_3$F$_2$ m/z 440.15474 [M+H]$^+$; found 440.15690.

Example 4

(E)-3-(3,5-difluorophenyl)-N-((1-(3-fluorophenyl)-9H-pyrido[3,4-b]indol-3-yl)methyl)acrylamide (1d)

To a solution of (1-(3-fluorophenyl)-9H-pyrido[3,4-b]indol-3-yl)methanamine (21a, 100 mg, 0.34 mmol) and (E)-3-(3,5-difluorophenyl)acrylic acid (22d, 63 mg, 0.34 mmol) in dry DMF (10 mL) was added HBTU (156 mg, 0.41 mmol) and triethylamine (0.14 mL, 1.03 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-20%), collected fractions and evaporated in vacuo to afford 1d as yellow solid 117 mg (75% yield); mp: 215-220° C. $^1$H NMR (300 MHz, DMSO-d$_6$+CDCl$_3$) δ (ppm): 10.95 (s, 0.7H), 8.30 (t, J=5.3 Hz, 1H), 8.14-8.05 (m, 1H), 7.99 (s, 1H), 7.96-7.75 (m, 3H), 7.65-7.43 (m, 3H), 7.28-7.15 (m, 2H), 7.06 (d, J=6.4 Hz, 2H), 6.84-6.75 (m, 2H), 4.87 (d, J=5.4 Hz, 2H), peak at 11.15 is due to the 30% minor rotamer; $^{13}$C NMR (75 MHz, DMSO-d$_6$+CDCl$_3$): 164.5, 163.8, 163.6, 160.4, 145.4, 141, 139.3, 137.8, 136.6, 131.8, 130.1, 129.4, 127.5, 123.7, 120.6, 120.3, 120, 118.8, 114.8, 114.5, 114.2, 111.5, 109.3, 103.8, 103.5, 103.1, 44.5; MS-ESI: m/z 458 [M+H]$^+$; HRMS (ESI): calcd for C$_{27}$H$_{19}$ON$_3$F$_3$ m/z 458.14559 [M+H]$^+$; found 458.14747.

Example 5

(E)-3-(2,5-dimethoxyphenyl)-N-((1-(3-fluorophenyl)-9H-pyrido[3,4-b]indol-3-yl)methyl)acrylamide (1e)

To a solution of (1-(3-fluorophenyl)-9H-pyrido[3,4-b]indol-3-yl)methanamine (21a, 100 mg, 0.34 mmol) and (E)-3-(2,5-dimethoxyphenyl)acrylic acid (22e, 71 mg, 0.34 mmol) in dry DMF (10 mL) was added HBTU (156 mg, 0.41 mmol) and triethylamine (0.14 mL, 1.03 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-22%), collected fractions and evaporated in vacuo to afford 1e as yellow solid 130 mg (79% yield); mp: 228-230° C. $^1$H NMR (300 MHz, DMSO-$d_6$+CDCl$_3$) δ (ppm): 10.87 (s, 0.8H), 8.10 (d, J=7.7 Hz, 1H), 800-7.78 (m, 5H), 7.65-7.42 (m, 3H), 7.28-7.15 (m, 2H), 7.07 (s, 1H), 6.86 (s, 2H), 6.75 (d, J=15.7 Hz, 1H), 4.88 (d, J=5.4 Hz, 2H), 3.83 (s, 3H), 3.78 (s, 3H), peaks at 11.08 and 8.06 are due to the 20% minor rotamer; $^{13}$C NMR (75 MHz, DMSO-$d_6$+CDCl$_3$) δ (ppm): 164.8, 163.0, 152, 150.9, 145.9, 145.5, 140.5, 138, 133.2, 131.2, 129.5, 129.0, 128.9, 126.8, 123.1, 121.3, 120.0, 119.7, 118.2, 114.3, 113.9, 113.6, 111.6, 111.1, 110.6, 54.7, 54.2, 43.9; MS-ESI: m/z 482 [M+H]$^+$; HRMS (ESI): calcd for C$_{29}$H$_{25}$O$_3$N$_3$F m/z 482.18536 [M+H]$^+$; found 482.18504.

Example 6

(E)-3-(4-chlorophenyl)-N-((1-(3-fluorophenyl)-9H-pyrido[3,4-b]indol-3-yl)methyl)acrylamide (1f)

To a solution of (1-(3-fluorophenyl)-9H-pyrido[3,4-b]indol-3-yl)methanamine (21a, 100 mg, 0.34 mmol) and (E)-3-(4-chlorophenyl)acrylic acid (22f, 62 mg, 0.34 mmol) in dry DMF (10 mL) was added HBTU (156 mg, 0.41 mmol) and triethylamine (0.14 mL, 1.03 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-20%), collected fractions and evaporated in vacuo to afford 1f as yellow solid 117 mg (75% yield); mp: 248-250° C.; $^1$H NMR (300 MHz, DMSO-$d_6$+CDCl$_3$) δ (ppm): 11.02 (s, 1H), 8.33-8.20 (m, 1H), 8.14-8.06 (m, 1H), 8.02-7.94 (m, 1H), 7.93-7.77 (m, 2H), 7.66-7.45 (m, 6H), 7.34 (d, J=8.3 Hz, 2H), 7.27-7.15 (m, 2H), 6.74 (d, J=15.6 Hz, 1H), 4.86 (d, J=5.2 Hz, 2H); $^{13}$C NMR (75 MHz, DMSO-$d_6$+CDCl$_3$) δ (ppm): 163.7, 159.4, 145.2, 140.2, 139.2, 136.2, 132.7, 132.2, 130.8, 129.1, 128.6, 127.4, 127.2, 126.5, 122.6, 121.2, 119.7, 119.3, 113.9, 113.4, 113.6, 112.2, 110.8, 110.2, 43.5; MS-ESI: m/z 456 [M+H]$^+$; HRMS (ESI): calcd for C$_{27}$H$_{20}$ON$_3$ClF m/z 456.12541 [M+H]$^+$; found 456.12734.

Example 7

(E)-N-((1-(3-fluorophenyl)-9H-pyrido[3,4-b]indol-3-yl)methyl)-3-(4-hydroxy-3-methoxyphenyl)acrylamide (1g)

To a solution of (1-(3-fluorophenyl)-9H-pyrido[3,4-b]indol-3-yl)methanamine (21a, 100 mg, 0.34 mmol) and (E)-3-(4-hydroxy-3-methoxyphenyl)acrylic acid (22g, 66 mg, 0.34 mmol) in dry DMF (10 mL) was added HBTU (156 mg, 0.41 mmol) and triethylamine (0.14 mL, 1.03 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-35%), collected fractions and evaporated in vacuo to afford 1g as yellow solid 109 mg (68% yield); mp: 205-210° C.; $^1$H NMR (300 MHz, DMSO-$d_6$+CDCl$_3$) δ (ppm): 10.80 (s, 1H), 8.19-8.04 (m, 1H), 8.03-7.93 (m, 1H), 7.92-7.73 (m, 3H), 7.65-7.48 (m, 5H), 7.31-7.14 (m, 2H), 7.08-6.98 (m, 1H), 6.91-6.83 (m, 1H), 6.52 (d, J=15.6 Hz, 1H), 4.86 (s, 2H), 4.70 (s, 1H), 3.90 (s, 3H); $^{13}$C NMR (75 MHz, DMSO-$d_6$+CDCl$_3$) δ (ppm): 165.3, 147.2, 146.7, 145.7, 140.7, 139, 131.5, 129.8, 129.6, 129.3, 129.2, 127.1, 125.7, 123.3, 123.1, 120.8, 120.2, 118.4, 117.6, 114.5, 114.2, 113.9, 111.5, 111.3, 110.8, 109.3, 54.7, 44.1; MS-ESI: m/z 468 [M+H]$^+$; HRMS (ESI): calcd for C$_{30}$H$_{27}$O$_4$N$_3$F m/z 468.16518 [M+H]$^+$; found 468.16801.

Example 8

(E)-N-((1-(3-fluorophenyl)-9H-pyrido[3,4-b]indol-3-yl)methyl)-3-(3-hydroxyphenyl)acrylamide (1h)

To a solution of (1-(3-fluorophenyl)-9H-pyrido[3,4-b]indol-3-yl)methanamine (21a, 100 mg, 0.34 mmol) and (E)-3-(3-hydroxyphenyl)acrylic acid (22h, 56 mg, 0.34 mmol) in dry DMF (10 mL) was added HBTU (156 mg, 0.41 mmol) and triethylamine (0.14 mL, 1.03 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-30%), collected fractions and evaporated in vacuo to afford 1h as yellow solid 97 mg (65% yield); mp: 142-148° C.; $^1$H NMR (300 MHz, DMSO-$d_6$+CDCl$_3$) δ (ppm): 11.01 (s, 1H), 8.29-8.19 (m, 1H), 8.16-8.05 (m, 1H), 8.01-7.94 (m, 1H), 7.92-7.77 (m, 2H), 7.66-7.48 (m, 3H), 7.29-7.13 (m, 4H), 7.07-6.96 (m, 2H), 6.89 (d, J=8.8 Hz, 1H), 6.69 (d, J=15.6 Hz, 1H), 4.86 (d, J=5.0 Hz, 2H), 4.69 (s, 1H); $^{13}$C NMR (75 MHz, DMSO-$d_6$+CDCl$_3$) δ (ppm): 165.2, 156.9, 145.7, 142.8, 140.9, 139.1, 135.4, 131.7, 130, 129.7, 128.7, 127.3, 123.5, 120.4, 119.9, 118.6, 118.1, 115.9, 114.7, 114.4, 114.1, 113.3, 112.7, 111.4, 111.1, 111.7, 44.3; MS-ESI: m/z 438 [M+H]$^+$; HRMS (ESI): calcd for C$_{27}$H$_{21}$N$_3$O$_2$F m/z 438.15969 [M+H]$^+$; found 438.16123.

Example 9

(E)-3-(3,4,5-trimethoxyphenyl)-N-((1-(3,4,5-trimethoxyphenyl)-9H-pyrido[3,4-b]indol-3-yl)methyl)acrylamide (2a)

To a solution of (1-(3,4,5-trimethoxyphenyl)-9H-pyrido[3,4-b]indol-3-yl)methanamine (21b, 100 mg, 0.27 mmol) and (E)-3-(3,4,5-trimethoxyphenyl)acrylic acid (22a, 65 mg, 0.27 mmol) in dry DMF (10 mL) was added HBTU (125 mg, 0.33 mmol) and triethylamine (0.11 mL, 0.82 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-30%), collected fractions and evaporated in vacuo to afford 2a as yellow solid 131 mg (82% yield); 165-170° C. $^1$H NMR (500 MHz, CDCl$_3$) δ (ppm): 8.54 (bs, 1H), 8.16 (d, J=7.7 Hz, 1H), 7.98 (s, 1H), 7.63-7.50 (m, 3H), 7.32 (t, J=7.1 Hz, 1H), 7.14 (s, 2H), 6.94 (s, 1H), 6.74 (s, 2H), 6.44 (d, J=15.5 Hz, 1H), 4.92 (d, J=5.1 Hz, 2H), 3.96 (s, 3H), 3.95 (s, 3H), 3.88 (s, 6H), 3.87 (s, 3H), peaks at 8.04, 7.48, 4.02 and 4.00 are due to 10% minor rotamer; $^{13}$C NMR (125 MHz, DMSO-d$_6$+ CDCl$_3$) δ (ppm): 164.9, 160.1, 152.1, 145.6, 140.8, 138.8, 131.6, 129.8, 129.3, 129.2, 127.3, 127.2, 123.4, 120.3, 120.2, 120.2, 118.5, 114.3, 114.0, 112.6, 111.4, 111.0, 103.9, 59.6, 55.0, 44.2; MS-ESI: m/z 584 [M+H]$^+$; HRMS (ESI): calcd for C$_{33}$H$_{34}$O$_7$N$_3$ m/z 584.23803 [M+H]$^+$; found 584.23913.

Example 10

(E)-3-(3,4-dichlorophenyl)-N-((1-(3,4,5-trimethoxyphenyl)-9H-pyrido[3,4-b]indol-3-yl)methyl)acrylamide (2b)

To a solution of (1-(3,4,5-trimethoxyphenyl)-9H-pyrido [3,4-b]indol-3-yl)methanamine (21b, 100 mg, 0.27 mmol) and (E)-3-(3,4-dichlorophenyl)acrylic acid (22b, 59 mg, 0.27 mmol) in dry DMF (10 mL) was added HBTU (125 mg, 0.33 mmol) and triethylamine (0.11 mL, 0.82 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-28%), collected fractions and evaporated in vacuo to afford 2b as yellow solid 130 mg (84% yield); 165-170° C. $^1$H NMR (300 MHz, DMSO-d$_6$+CDCl$_3$) δ (ppm): 11.0 (s, 1H), 8.17-8.0 (m, 2H), 7.96 (s, 1H), 7.65-7.57 (m, 3H), 7.55-7.44 (m, 4H), 7.41-7.36 (m, 1H), 7.27-7.19 (t, J=7.9 Hz, 1H), 6.76 (d, J=15.6 Hz, 1H), 4.89 (d, J=5.4 Hz, 2H), 4.01 (s, 6H), 3.92 (m, 3H); $^{13}$C NMR (75 MHz, DMSO-d$_6$+CDCl$_3$) δ (ppm): 164.1, 152.0, 145.1, 140.6, 136.9, 138.1, 136.0, 135.7, 134.4, 133.4, 132.9, 131.3, 129.5, 129.3, 127.9, 126.8, 125.8, 122.9, 120.1, 119.9, 118.2, 111.2, 110.0, 104.8, 59.4, 54.9, 44.0; MS-ESI: m/z 562 [M+H]$^+$; HRMS (ESI): calcd for C$_{30}$H$_{26}$O$_4$N$_3$Cl$_2$ m/z 562.12828 [M+H]$^+$; found 562.12949.

Example 11

(E)-3-(4-fluorophenyl)-N-((1-(3,4,5-trimethoxyphenyl)-9H-pyrido[3,4-b]indol-3-yl)methyl)acrylamide (2c)

To a solution of (1-(3,4,5-trimethoxyphenyl)-9H-pyrido [3,4-b]indol-3-yl)methanamine (21b, 100 mg, 0.27 mmol) and (E)-3-(4-fluorophenyl)acrylic acid (22c, 45 mg, 0.27 mmol) in dry DMF (10 mL) was added HBTU (125 mg, 0.33 mmol) and triethylamine (0.11 mL, 0.82 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-22%), collected fractions and evaporated in vacuo to afford 2c as yellow solid 123 mg (88% yield); mp: 214-218° C.; $^1$H NMR (300 MHz, DMSO-d$_6$+CDCl$_3$) δ (ppm): 10.99 (s, 1H), 8.11 (d, J=7.7 Hz, 1H), 8.01 (t, J=7.3 Hz, 1H), 7.97 (s, 1H), 7.67-7.45 (m, 6H), 7.28-7.20 (m, 2H), 7.07 (t, J=8.6 Hz, 2H), 6.65 (d, J=15.6 Hz, 1H), 4.89 (d, J=5.4 Hz, 2H), 4.00 (s, 6H), 3.92 (s, 3H); $^{13}$C NMR: 165.3, 164.1, 160.8, 152.7, 145.5, 141.3, 141.1, 138.7, 137.5, 133.4, 132.0, 130.7, 130.0, 128.7, 127.5, 120.7, 118.8, 114.9, 111.7, 110.8, 105.2, 120.5, 60.0, 55.5, 44.5; MS-ESI: m/z 512 [M+H]$^+$; HRMS (ESI): calcd for C$_{30}$H$_{27}$O$_4$N$_3$F m/z 512.19610 [M+H]$^+$; found 512.19801.

Example 12

(E)-3-(3,5-difluorophenyl)-N-((1-(3,4,5-trimethoxyphenyl)-9H-pyrido[3,4-b]indol-3-yl)methyl)acrylamide (2d)

To a solution of (1-(3,4,5-trimethoxyphenyl)-9H-pyrido [3,4-b]indol-3-yl)methanamine (21b, 100 mg, 0.27 mmol) and (E)-3-(3,5-difluorophenyl)acrylic acid (22d, 50 mg, 0.27 mmol) in dry DMF (10 mL) was added HBTU (125 mg, 0.33 mmol) and triethylamine (0.11 mL, 0.82 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-25%), collected fractions and evaporated in vacuo to afford 2d as yellow solid 113 mg (78% yield); mp: 228-230° C.; $^1$H NMR (300 MHz, DMSO-d$_6$+CDCl$_3$) δ (ppm): 10.68 (s, 1H), 8.12 (d, J=7.7 Hz, 1H), 7.96 (s, 1H), 7.80 (t, J=4.9 Hz, 1H), 7.64-7.48 (m, 3H), 7.40 (s, 2H), 7.25 (t, J=6.6 Hz, 1H), 7.04 (d, J=6.4 Hz, 2H), 6.84-6.75 (m, 1H), 6.68 (d, J=15.6 Hz, 1H), 4.91 (d, J=5.4 Hz, 2H), 4.00 (s, 6H), 3.94 (s, 3H); $^{13}$C NMR (125 MHz, DMSO-d$_6$+CDCl$_3$) δ (ppm): 165.3, 164.1, 162.0, 146.1, 141.8, 138.7, 138.2, 137.5, 134.2, 132.7, 130.6, 128.1, 124.6, 121.4, 121.2, 119.5, 112.4, 110.4, 110.2, 105.9, 104.3, 60.8, 56.2, 45.3, 40.2; MS-ESI: m/z 530 [M+H]$^+$; HRMS (ESI): calcd for C$_{30}$H$_{26}$O$_4$N$_3$F$_2$ m/z 530.18649 [M+H]$^+$; found 530.18859.

Example 13

(E)-3-(2,5-dimethoxyphenyl)-N-((1-(3,4,5-trimethoxyphenyl)-9H-pyrido[3,4-b]indol-3-yl)methyl)acrylamide (2e)

To a solution of (1-(3,4,5-trimethoxyphenyl)-9H-pyrido [3,4-b]indol-3-yl)methanamine (21b, 100 mg, 0.27 mmol) and (E)-3-(2,5-dimethoxyphenyl)acrylic acid (22e, 57 mg, 0.27 mmol) in dry DMF (10 mL) was added HBTU (125 mg, 0.33 mmol) and triethylamine (0.11 mL, 0.82 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-28%), collected fractions and evaporated in vacuo to afford 2e as yellow solid 123 mg (81% yield); mp: 148-150° C.; $^1$H NMR (300 MHz, DMSO-d$_6$+CDCl$_3$) δ (ppm): 10.66 (s, 1H), 8.13 (d, J=7.9 Hz, 1H), 7.98 (s, 1H), 7.90 (d, J=15.8 Hz, 1H), 7.63-7.42 (m, 3H), 7.29-7.22 (m, 3H), 7.05 (s, 1H), 6.86 (s, 2H), 6.69 (d, J=15.8 Hz, 1H), 4.90 (d, J=5.2 Hz, 2H), 4.00 (s, 6H), 3.93 (3H), 3.83 (s, 3H), 3.78 (s, 3H); $^{13}$C NMR (75 MHz, DMSO-d$_6$+CDCl$_3$) δ (ppm): 165.5, 158.5, 152.4, 151.4, 145.3, 141.0, 140.6, 137.2, 134.1, 133.0, 131.7, 129.8, 127.3, 123.6, 121.6, 120.5, 120.2, 118.6, 114.8, 114.4, 112.3, 111.5, 110.5, 105, 59.8, 55.2, 54.7, 44.1; MS-ESI: m/z 554 [M+H]$^+$; HRMS (ESI): calcd for C$_{32}$H$_{32}$O$_6$N$_3$ m/z 554.22685 [M+H]$^+$; found 554.22856.

Example 14

(E)-3-(4-chlorophenyl)-N-((1-(3,4,5-trimethoxyphenyl)-9H-pyrido[3,4-b]indol-3-yl)methyl)acrylamide (2f)

To a solution of (1-(3,4,5-trimethoxyphenyl)-9H-pyrido[3,4-b]indol-3-yl)methanamine (21b, 100 mg, 0.27 mmol) and (E)-3-(4-chlorophenyl)acrylic acid (22f, 50 mg, 0.27 mmol) in dry DMF (10 mL) was added HBTU (125 mg, 0.33 mmol) and triethylamine (0.11 mL, 0.82 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-22%), collected fractions and evaporated in vacuo to afford 2f as yellow solid 116 mg (80% yield); mp: 148-150° C.; $^1$H NMR (300 MHz, DMSO-d$_6$+CDCl$_3$) δ (ppm): 11.00 (s, 1H), 8.11 (d, J=7.7 Hz, 1H), 8.08-8.01 (m, 1H), 7.97 (s, 1H), 7.66-7.57 (m, 2H), 7.56-7.45 (m, 3H), 7.34 (d, J=8.5 Hz, 2H), 7.30-7.20 (m, 3H), 6.71 (d, J=15.8 Hz, 1H), 4.89 (d, J=5.2 Hz, 2H), 4.00 (s, 6H), 3.92 (s, 3H); $^{13}$C NMR (75 MHz, DMSO-d$_6$+CDCl$_3$) δ (ppm): 164.9, 152.4, 145.2, 141.0, 140.7, 137.5, 137.2, 137.0, 133.8, 133.0 132.8, 131.7, 129.7, 128.0, 127.3, 121.5, 120.5, 120.2, 118.6, 111.5, 110.5, 105.0, 59.7, 55.2, 44.2; MS-ESI: m/z 528 [M+H]$^+$; HRMS (ESI): calcd for C$_{30}$H$_{27}$O$_4$N$_3$Cl m/z 528.16718 [M+H]$^+$; found 528.16846.

Example 15

(E)-3-(4-hydroxy-3-methoxyphenyl)-N-((1-(3,4,5-trimethoxyphenyl)-9H-pyrido[3,4-b]indol-3-yl)methyl)acrylamide (2g)

To a solution of (1-(3,4,5-trimethoxyphenyl)-9H-pyrido[3,4-b]indol-3-yl)methanamine (21b, 100 mg, 0.27 mmol) and (E)-3-(4-hydroxy-3-methoxyphenyl)acrylic acid (22g, 53 mg, 0.27 mmol) in dry DMF (10 mL) was added HBTU (125 mg, 0.33 mmol) and triethylamine (0.11 mL, 0.82 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-26%), collected fractions and evaporated in vacuo to afford 2g as yellow solid 109 mg (74% yield); mp: 175-178° C.; $^1$H NMR (300 MHz, DMSO-d$_6$+CDCl$_3$) δ (ppm): 10.53 (s, 1H), 8.12 (d, J=7.7 Hz, 1H), 7.96 (s, 1H), 7.65-7.48 (m, 4H), 7.37 (s, 1H), 7.35 (m, 4H), 7.07-6.99 (m, 2H), 6.87 (d, J=8.6 Hz, 1H), 6.45 (d, J=15.4 Hz, 1H), 4.90 (s, 2H), 4.00 (s, 6H), 3.93 (s, 3H), 3.89 (s, 3H); $^{13}$C NMR (75 MHz, DMSO-d$_6$+CDCl$_3$) δ (ppm): 166.6, 153.5, 148.5, 146.3, 142.0, 140.3, 138.2, 133.8, 133.8, 132.6, 128.3, 126.8, 122.0, 121.5, 121.1, 119.6, 118.6, 115.7, 112.5, 111.5, 110.5, 106.1, 60.7, 56.2, 55.9; MS-ESI: m/z 540 [M+H]$^+$; HRMS (ESI): calcd for C$_{31}$H$_{29}$O$_6$N$_3$ m/z 540.20564 [M+H]$^+$; found 540.21173.

Example 16

(E)-3-(3-hydroxyphenyl)-N-((1-(3,4,5-trimethoxyphenyl)-9H-pyrido[3,4-b]indol-3-yl)methyl)acrylamide (2h)

To a solution of (1-(3,4,5-trimethoxyphenyl)-9H-pyrido[3,4-b]indol-3-yl)methanamine (21b, 100 mg, 0.27 mmol) and (E)-3-(3-hydroxyphenyl)acrylic acid (22h, 45 mg, 0.27 mmol) in dry DMF (10 mL) was added HBTU (125 mg, 0.33 mmol) and triethylamine (0.11 mL, 0.82 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-26%), collected fractions and evaporated in vacuo to afford 2h as yellow solid 98 mg (70% yield); mp: 175-178° C.; $^1$H NMR (300 MHz, DMSO-d$_6$+CDCl$_3$) δ (ppm): 10.79 (s, 1H), 8.12 (d, J=7.7 Hz, 1H), 7.96 (s, 1H), 7.71-7.58 (m, 3H), 7.57-7.40 (m, 4H), 7.30-7.14 (m, 4H), 7.11-6.96 (m, 2H), 6.84 (d, J=9.4 Hz, 1H), 6.61 (d, J=15.6 Hz, 1H), 4.90 (d, J=5.2 Hz, 2H), 4.71 (s, 1H), 4.00 (s, 6H), 3.92 (s, 3H); $^{13}$C NMR (75 MHz, DMSO-d$_6$+CDCl$_3$) δ (ppm): 165.0, 156.6, 152.2, 146, 145.4, 140.7, 138.9, 135.2, 133.1, 132.6, 131.5, 126.9, 129.4, 120.5, 120.3, 120.1, 118.3, 117.8, 115.7, 114.5, 113.1, 111.3, 110.1, 104.8, 59.5, 55.0, 44.1; MS-ESI: m/z 510 [M+H]$^+$; HRMS (ESI): calcd for C$_{30}$H$_{28}$O$_5$N$_3$ [M+H]$^+$ 510.20051; found 510.20235.

Example 17

(E)-N-((1-(4-methoxyphenyl)-9H-pyrido[3,4-b]indol-3-yl)methyl)-3-(3,4,5-trimethoxyphenyl)acrylamide (3a)

To a solution of (1-(4-methoxyphenyl)-9H-pyrido[3,4-b]indol-3-yl)methanamine (21c, 100 mg, 0.33 mmol) and (E)-3-(3-hydroxyphenyl)acrylic acid (22a, 78 mg, 0.33 mmol) in dry DMF (10 mL) was added HBTU (150 mg, 0.39 mmol) and triethylamine (0.13 mL, 0.99 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-20%), collected fractions and evaporated in vacuo to afford 3a as yellow solid 138 mg (80% yield); mp: 148-150° C.; $^1$H NMR (300 MHz, DMSO-d$_6$+CDCl$_3$) δ (ppm): 10.22 (s, 1H), 8.11 (d, J=7.7 Hz, 1H), 7.99 (d, J=8.7 Hz, 2H), 7.92 (s, 1H), 7.62-7.49 (m, 4H), 7.25 (t, J=7.7 Hz, 1H), 7.12 (d, J=8.7 Hz, 2H), 6.76 (s, 2H), 6.55 (d, J=15.4 Hz, 1H), 4.89 (d, J=5.1 Hz, 2H), 3.90 (s, 3H), 3.88 (s, 6H), 3.86 (s, 3H); $^{13}$C NMR (75 MHz, DMSO-d$_6$+CDCl$_3$) δ (ppm): 165.2, 159.2, 152.4, 145.2, 140.8, 140.0, 139.2, 138.3, 131.7, 130.0, 129.8, 129.2, 127.4, 124.9, 120.6, 120.4, 120.3, 118.7, 113.4, 111.6, 110.4, 104.1, 55.9, 55.2, 54.6, 44.4; MS-ESI: m/z 516 [M+H]$^+$; HRMS (ESI): calcd for C$_{31}$H$_{30}$O$_5$N$_3$ m/z 524.21800 [M+H]$^+$; found 524.21613.

Example 18

(E)-3-(3,4-dichlorophenyl)-N-((1-(4-methoxyphenyl)-9H-pyrido[3,4-b]indol-3-yl)methyl)acrylamide (3b)

To a solution of (1-(4-methoxyphenyl)-9H-pyrido[3,4-b]indol-3-yl)methanamine (21c, 100 mg, 0.33 mmol) and (E)-3-(3,4-dichlorophenyl)acrylic acid (22b, 71 mg, 0.33 mmol) in dry DMF (10 mL) was added HBTU (150 mg, 0.39 mmol) and triethylamine (0.13 mL, 0.99 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-21%), collected fractions and evaporated in vacuo to afford 3b as yellow solid 137 mg (83% yield); mp: 188-190° C.; $^1$H NMR (300 MHz, DMSO-d$_6$+CDCl$_3$) δ (ppm): 10.01 (s, 1H), 8.11 (d, J=7.7 Hz, 1H), 8.02-7.71 (m, 4H), 7.63-7.48 (m, 4H), 7.47-7.25 (m, 3H), 7.11 (d, J=8.4 Hz, 2H), 6.61 (d, J=15.6 Hz, 1H), 4.88 (d, J=4.9 Hz, 2H), 3.90 (s, 3H); $^{13}$C NMR (75 MHz, DMSO-d$_6$+CDCl$_3$) δ (ppm): 164.4, 159.1, 145.2, 141.3, 140.9, 136.4, 134.7, 133.3, 131.9, 131.8, 130.3, 129.9, 129.7, 128.3, 127.3, 126.2, 123.0, 120.6, 120.5, 118.7, 113.4, 111.5, 110.4, 110.1, 54.6, 44.6; MS-ESI: m/z 502 [M+H]$^+$; HRMS (ESI): calcd for C$_{28}$H$_{22}$O$_2$N$_3$Cl$_2$ m/z 502.10836 [M+H]$^+$; found 502.10691.

Example 19

(E)-3-(4-fluorophenyl)-N-((1-(4-methoxyphenyl)-9H-pyrido[3,4-b]indol-3-yl)methyl)acrylamide (3c)

To a solution of (1-(4-methoxyphenyl)-9H-pyrido[3,4-b]indol-3-yl)methanamine (21c, 100 mg, 0.33 mmol) and (E)-3-(4-fluorophenyl)acrylic acid (22c, 54 mg, 0.33 mmol) in dry DMF (10 mL) was added HBTU (150 mg, 0.39 mmol) and triethylamine (0.13 mL, 0.99 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-24%), collected fractions and evaporated in vacuo to afford 3c as yellow solid 126 mg (85% yield); mp: 145-148° C.; $^1$H NMR (300 MHz, DMSO-d$_6$+CDCl$_3$) δ (ppm): 10.84 (s, 1H), 8.19 (t, J=5.0 Hz, 1H), 8.11 (d, J=7.9 Hz, 1H), 8.02 (d, J=8.5 Hz, 2H), 7.94 (s, 1H), 7.64-7.60 (m 2H), 7.58-7.47 (m, 3H), 7.23 (t, J=7.5 Hz, 1H), 7.15-7.03 (m, 4H), 6.67 (d, J=15.6 Hz, 1H), 4.85 (d, J=5.4 Hz, 2H), 3.92 (s, 3H); $^{13}$C NMR (75 MHz, DMSO-d$_6$+CDCl$_3$) δ (ppm): 163.8, 159.5, 158.1, 144.9, 140.0, 139.7, 136.3, 130.5, 129.8, 129.3, 128.5, 128.2, 127.8, 126.2, 120.3, 119.6, 119.3, 117.6, 113.9, 112.3, 110.8, 109.1, 53.6, 43.5; MS-ESI: m/z 452 [M+H]$^+$; HRMS (ESI): calcd for C$_{28}$H$_{23}$F O$_2$N$_3$ m/z 451.16961 [M+H]$^+$; found 452.17471.

Example 20

(E)-3-(3,5-difluorophenyl)-N-((1-(4-methoxyphenyl)-9H-pyrido[3,4-b]indol-3-yl)methyl)acrylamide (3d)

To a solution of (1-(4-methoxyphenyl)-9H-pyrido[3,4-b]indol-3-yl)methanamine (21c, 100 mg, 0.33 mmol) and (E)-3-(3,5-difluorophenyl)acrylic acid (22d, 60 mg, 0.33 mmol) in dry DMF (10 mL) was added HBTU (150 mg, 0.39 mmol) and triethylamine (0.13 mL, 0.99 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-20%), collected fractions and evaporated in vacuo to afford 3d as yellow solid 136 mg (88% yield); mp: 230-232° C.; $^1$H NMR (300 MHz, DMSO-d$_6$+CDCl$_3$) δ (ppm): 10.92 (s, 1H), 8.43 (s, 1H), 8.11 (d, J=7.7 Hz, 1H), 8.02 (d, J=8.5 Hz, 2H), 7.93 (s, 1H), 7.62 (d, J=8.3 Hz, 1H), 7.50 (t, J=6.6 Hz, 2H), 7.23 (t, J=7.5 Hz, 1H), 7.15-7.06 (m, 4H), 6.81 (d, J=15.4 Hz, 2H), 4.84 (d, J=5.4 Hz, 2H), 3.91 (s, 3H); $^{13}$C NMR (75 MHz, DMSO-d$_6$+CDCl$_3$) δ (ppm): 164.8, 158.8, 145.1, 140.7, 136.2, 131.5, 130.1, 129.3, 128.9, 126.9, 123.7, 120.3, 120.2, 118.4, 113.1, 111.3, 110.0, 109.4, 109.2, 109.1, 103.2, 54.3, 44.3; MS-ESI: m/z 470 [M+H]$^+$; HRMS (ESI); calcd for C$_{28}$H$_{22}$O$_2$N$_3$F$_2$ m/z 470.16746 [M+H]$^+$; found 470.16570.

Example 21

(E)-3-(2,5-dimethoxyphenyl)-N-((1-(4-methoxyphenyl)-9H-pyrido[3,4-b]indol-3-yl)methyl)acrylamide (3e)

To a solution of (1-(4-methoxyphenyl)-9H-pyrido[3,4-b]indol-3-yl)methanamine (21c, 100 mg, 0.33 mmol) and (E)-3-(2,5-dimethoxyphenyl)acrylic acid (22e, 68 mg, 0.33 mmol) in dry DMF (10 mL) was added HBTU (150 mg, 0.39 mmol) and triethylamine (0.13 mL, 0.99 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-22%), collected fractions and evaporated in vacuo to afford 3e as yellow solid 146 mg (90% yield); mp: 130-135° C.; $^1$H NMR (300 MHz, DMSO-$d_6$+CDCl$_3$) δ (ppm): 10.58 (s, 1H), 8.12 (d, J=7.7 Hz, 1H), 7.99 (d, J=8.7 Hz, 2H), 7.96 (s, 1H), 7.90 (d, J=15.8 Hz, 1H), 7.76 (t, J=5.3, 1H), 7.61 (d, J=8.3 Hz, 1H), 7.53 (t. J=6.9 Hz, 1H), 7.26 (t, J=7.5 Hz, 1H), 7.13 (d, J=8.8 Hz, 2H), 7.07 (s, 1H), 6.86 (s, 2H), 6.71 (d, J=15.8 Hz, 1H), 4.87 (d, J=5.4 Hz, 2H), 3.91 (s, 3H), 3.83 (s, 3H), 3.78 (s, 3H); $^{13}$C NMR (75 MHz, DMSO-$d_6$+CDCl$_3$) δ (ppm): 166.1, 159.6, 152.8, 151.9, 144.9, 141.4, 140.8, 134.9, 131.9, 130.4, 129.5, 129.4, 127.9, 124.0, 121.6, 121.0, 120.6, 119.2, 115.3, 113.8, 112.9, 111.8, 111.9, 111.0, 55.5, 55.1, 54.8, 44.3; MS-ESI: m/z 494 [M+H]$^+$; HRMS (ESI): calcd for $C_{30}H_{28}O_4N_3$ m/z 494.20743 [M+H]$^+$; found 494.20549.

Example 22

(E)-3-(4-chlorophenyl)-N-((1-(4-methoxyphenyl)-9H-pyrido[3,4-b]indol-3-yl)methyl)acrylamide (3f)

To a solution of (1-(4-methoxyphenyl)-9H-pyrido[3,4-b]indol-3-yl)methanamine (21c, 100 mg, 0.33 mmol) and (E)-3-(4-chlorophenyl)acrylic acid (22f, 60 mg, 0.33 mmol) in dry DMF (10 mL) was added HBTU (150 mg, 0.39 mmol) and triethylamine (0.13 mL, 0.99 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-25%), collected fractions and evaporated in vacuo to afford 3f as yellow solid 127 mg (83% yield); mp: 140-145° C. $^1$H NMR (300 MHz, DMSO-$d_6$+CDCl$_3$) δ (ppm): 11.18 (s, 1H), 8.60 (t, J=5.4 Hz, 1H), 8.11 (d, J=7.9 Hz, 1H), 8.03 (d, J=8.7 Hz, 2H), 7.92 (d, J=3.2 Hz, 2H), 7.63 (d, J=8.3 Hz, 1H), 7.57 (m, 3H), 7.36 (d, J=8.5 Hz, 2H), 7.21 (t, J=7.4 Hz, 1H), 7.12 (d, J=8.8 Hz, 2H), 6.79 (d, J=15.8 Hz, 1H), 4.80 (d, J=5.6 Hz, 2H), 3.90 (s, 3H); $^{13}$C NMR (75 MHz, DMSO-$d_6$+CDCl$_3$) δ (ppm): 164.9, 159.4, 146.2, 141.3, 141.1, 137.5, 133.9, 133.5, 131.8, 130.6, 129.8, 129.5, 128.7, 128.5, 127.5, 122.6, 120.9, 120.7, 118.9, 113.6, 112.1, 110.4, 54.9, 4.8; MS-ESI: m/z 468 [M+H]$^+$; HRMS (ESI): calcd for $C_{28}H_{23}O_2N_3$ Cl m/z 468.14733 [M+H]$^+$; found 468.14598.

Example 23

(E)-3-(4-hydroxy-3-methoxyphenyl)-N-((1-(4-methoxyphenyl)-9H-pyrido[3,4-b]indol-3-yl)methyl)acrylamide (3g)

To a solution of (1-(4-methoxyphenyl)-9H-pyrido[3,4-b]indol-3-yl)methanamine (21c, 100 mg, 0.33 mmol) and (E)-3-(4-hydroxy-3-methoxyphenyl)acrylic acid (22g, 64 mg, 0.33 mmol) in dry DMF (10 mL) was added HBTU (150 mg, 0.39 mmol) and triethylamine (0.13 mL, 0.99 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-30%), collected fractions and evaporated in vacuo to afford 3g as yellow solid 121 mg (77% yield); mp: 215-220° C.; $^1$H NMR (300 MHz, DMSO-$d_6$+CDCl$_3$) δ (ppm): 10.53 (s, 1H), 8.09 (d, J=7.5 Hz, 1H), 8.00 (d, J=8.7 Hz, 2H), 7.94-7.87 (m, 2H), 7.74-7.45 (m, 4H), 7.28-7.17 (m, 1H), 7.21 (d, J=8.5 Hz, 2H), 7.06-6.98 (m, 1H), 6.86 (d, J=7.9 Hz, 1H), 6.50 (d, J=15.6 Hz, 1H), 4.86 (d, J=4.9 Hz, 2H), 4.65 (s, 1H), 3.90 (s, 3H), 3.89 (s, 3H); $^{13}$C NMR (75 MHz, DMSO-$d_6$+CDCl$_3$) δ (ppm): 165.7, 159.2, 147.5, 146.9, 145.5, 140.9, 139.6, 131.8, 130.4, 129.7, 129.2, 128.9, 127.3, 126.2, 121.3, 120.7, 120.6, 118.7, 117.8, 113.5, 111.6, 110.4, 109.6, 55.1, 54.6, 44.5; MS-ESI: m/z 480 [M+H]$^+$; HRMS (ESI): calcd for $C_{29}H_{26}O_4N_3$ m/z 480.19178 [M+H]$^+$; found 480.19010.

Example 24

(E)-3-(3-hydroxyphenyl)-N-((1-(4-methoxyphenyl)-9H-pyrido[3,4-b]indol-3-yl)methyl)acrylamide (3h)

To a solution of (1-(4-methoxyphenyl)-9H-pyrido[3,4-b]indol-3-yl)methanamine (21c, 100 mg, 0.33 mmol) and (E)-3-(3-hydroxyphenyl)acrylic acid (22h, 54 mg, 0.33 mmol) in dry DMF (10 mL) was added HBTU (150 mg, 0.39 mmol) and triethylamine (0.13 mL, 0.99 mmol) under nitrogen atmosphere and the reaction mixture was stirred at 35° C. for 12 h. After the complete consumption of starting materials (monitored by TLC), the contents of the reaction were cooled to 35° C. and poured into ice-cold water (25 mL), extracted by ethyl acetate (3×30 mL) and the combined organic phases were washed with brine (20 mL), dried over anhydrous sodium sulfate, filtered and concentrated in vacuo. The obtained residue was purified by column chromatography using ethyl acetate/n-hexane (0-30%), collected fractions and evaporated in vacuo to afford 3h as yellow solid 103 mg (70% yield); mp: 165-170° C.; $^1$H NMR (300 MHz, DMSO-$d_6$+CDCl$_3$) δ (ppm): 10.69 (s, 1H), 9.12 (bs, 1H), 8.10 (d, J=7.6 Hz, 1H), 8.04-7.92 (m, 4H), 7.64-7.48 (m, 5H), 7.28-7.07 (m, 3H), 7.02-6.97 (m, 2H), 6.83 (d, J=9.4 Hz, 1H), 6.64 (d, J=15.5 Hz, 1H), 4.86 (d, J=5.1 Hz, 2H), 3.90 (s, 3H); $^{13}$C NMR (75 MHz, DMSO-$d_6$+CDCl$_3$) δ (ppm): 165.2, 158.9, 156.7, 145.2, 140.9, 140.5, 139.1, 135.4, 131.5, 129.8, 129.6, 129.0, 128.7, 127.1, 120.5, 120.4, 120.2, 118.5, 118.0, 115.9, 113.3, 113.1, 111.4, 110.2, 54.4, 44.2; MS-ESI: m/z 450 [M+H]$^+$; HRMS (ESI); calcd for $C_{28}H_{23}O_3N_3$ m/z 450.18122 [M+H]$^+$; found 450.17918.

BIOLOGICAL ACTIVITY

Comparative Cytotoxicity Data of (1-phenyl-9H-pyrido[3,4-b]indol-3-yl)methanamines and phenylcinnamides.

TABLE 1

The $IC_{50}$ values[a] (in µM) for (1-phenyl-9H-pyrido[3,4-b]indol-3-yl)methanamines 21b, 21c and 21e on selected cancer cell lines (A. Kamal et al. reported in *Bioorg. Med. Chem.* 2015, 23, 5511-5526).

| Compound | A549[b] | MCF-7[c] | HeLa[d] |
|---|---|---|---|
| 21b | 15.13 | 18.62 | 21.66 |
| 21c | 17.84 | 18.91 | 18.59 |
| 21e | 15.84 | 12.02 | 15.76 |

[a]50% Inhibitory concentration after 48 h of drug treatment and the values are average of three individual experiments,
[b]lung cancer,
[c]breast cancer,
[d]cervical cancer.

Hergenrother and co-workers have synthesized phenylcinnamide derivatives and evaluated for their cytotoxic activity. Several new derivatives have shown cytotoxicity with $IC_{50}$ values ranging from 1 to 10 µM (*J. Med. Chem.* 2010, 53, 3964).

The cytotoxic activity studies for these N-((1-phenyl-9H-pyrido[3,4-b]indol-3-yl)methyl)cinnamamides (1a-h, 2a-h and 3a-h) were carried out in some representative human cancer cell lines. The cytotoxicity data revealed that these derivatives shows enhanced cytotoxicity (nM) than (1-phenyl-9H-pyrido[3,4-b]indol-3-yl)methanamines and phenylcinnamide (µM).

Anticancer Activity

The N-((1-phenyl-9H-pyrido[3,4-b]indol-3-yl)methyl)cinnamamides (1a-h, 2a-h and 3a-h) have been tested against five human cancer cell lines such as A549 (lung cancer), MCF-7 (breast cancer), B16 (melanoma), HeLa (cervical cancer) and NIH3T3 (mouse embryonic fibroblast cancer). All the cancer cell lines (HeLa, A549, MCF-7 and B16) were procured from National Centre for Cell Sciences (NCCS, Pune, India) and NIH 3T3 cell line was obtained from American Type Culture Collection (Rockville, Md., USA). Stock cells were cultured in DMEM supplemented with 10% Fetal Bovine Serum (FBS), in an humidified atmosphere of 5% $CO_2$ at 37° C. until they are 80% confluent. To study the cytotoxicity of the compounds, after 80% confluence, cells were trypsinized with 0.1% trypsin-EDTA and harvested by centrifugation at 500×g. Serial dilutions of cells were made from $1\times10^6$ to $1\times10^3$ cells per mL The cells were seeded in triplicate in a 96 well plate. The cells were seeded in triplicate in a 96 well plate. The suspended cells were treated with 1, 3, 5, 10, 25, 50, 100, 500, 1000, 2000, 5000 and 10,000 nM of each compound (1a-h, 2a-h and 3a-h) for 24 h duration. Since Doxorubicin was known as potential anticancer drug, the cells were treated with Doxorubicin, in the same concentration range was considered as control. The cell viability was determined by measuring the ability of cells to transform MTT to a purple coloured formazan dye. The absorbance of samples at 570 nm was measured using a UV-Visible spectrophotometer. Percentage of viable cells was calculated by using the formula given below.

$$\text{Percentage of cell viability} = \frac{OD_{570} \text{ Sample}}{OD_{570} \text{ Control}} \times 100$$

Where the $OD_{570}$ (sample) corresponds to absorbance obtained from the wells treated with compound and $OD_{570}$ (control) represents the absorbance from the wells in which no compound was added. For these compounds results are expressed as half maximal inhibitory concentration ($IC_{50}$) values and the anticancer activity data of 1a-h, 2a-h and 3a-h are shown in Table 2. All the synthesized derivatives are very active than the precursor amines 21b, 21c and 21e (A. Kamal et al. Reported the $IC_{50}$ values of 21b, 21c and 21e in *Bioorg. Med. Chem.* 2015, 23, 5511-5526, Table 1) and all the synthesized derivatives are significantly active against all the cell lines tested ($IC_{50}$=13-45 nM) and compared with doxorubicin as control. However all the derivatives are very active than doxorubicin (>500 nM) and all the derivatives are active against MCF-7 cells (13-20 nM) than other cell lines. Moreover, the derivatives 3a, 3f and 3h are most active among these derivatives against MCF-7 cells (13.43, 14.05 and 13.84 nM respectively).

TABLE 2

$IC_{50}$ values[a] (in nM) for 1a-h to 3a-h on selected cancer cell lines.

| Compound | A549[b] | MCF-7[c] | B16 | HeLa[e] | NIH3T3[f] |
|---|---|---|---|---|---|
| 1a | 17.92 ± 0.6 | 16.23 ± 1.5 | 19.76 ± 0.6 | 22.98 ± 0.7 | 35.98 ± 1.3 |
| 1b | 18.02 ± 0.8 | 17.02 ± 1.2 | 18.93 ± 0.4 | 24.87 ± 0.4 | 38.98 ± 1.1 |
| 1c | 16.33 ± 0.3 | 16.46 ± 1.8 | 16.84 ± 0.8 | 24.32 ± 0.6 | 30.77 ± 2.1 |
| 1d | 21.03 ± 1.2 | 16.54 ± 0.6 | 18.23 ± 0.3 | 23.56 ± 0.5 | 35.98 ± 2.3 |
| 1e | 22.23 ± 1.1 | 17.54 ± 0.3 | 19.85 ± 0.7 | 21.87 ± 0.2 | 39.65 ± 1.8 |
| 1f | 19.56 ± 1.6 | 18.34 ± 0.8 | 18.23 ± 1.3 | 19.23 ± 0.6 | 43.65 ± 1.1 |
| 1g | 22.42 ± 1.1 | 17.93 ± 0.7 | 19.45 ± 1.1 | 23.85 ± 0.4 | 36.86 ± 1.9 |
| 1h | 23.43 ± 0.8 | 19.23 ± 0.6 | 24.93 ± 0.5 | 26.98 ± 0.5 | 35.66 ± 2.2 |
| 2a | 21.34 ± 0.9 | 16.54 ± 1.1 | 17.23 ± 0.4 | 23.48 ± 0.3 | 38.87 ± 2.5 |
| 2b | 20.43 ± 0.7 | 17.52 ± 1.4 | 16.87 ± 0.7 | 25.87 ± 0.2 | 39.23 ± 1.9 |
| 2c | 18.74 ± 0.7 | 16.37 ± 0.8 | 17.25 ± 0.3 | 19.98 ± 0.5 | 42.98 ± 1.1 |
| 2d | 21.57 ± 1.2 | 19.65 ± 1.1 | 24.08 ± 0.7 | 23.82 ± 0.3 | 36.29 ± 1.7 |
| 2e | 18.77 ± 1.4 | 17.23 ± 0.6 | 19.23 ± 1.4 | 25.09 ± 0.2 | 38.97 ± 1.9 |
| 2f | 18.85 ± 1.7 | 17.53 ± 0.9 | 18.69 ± 1.1 | 26.83 ± 0.4 | 35.62 ± 2.1 |
| 2g | 18.26 ± 1.4 | 17.55 ± 0.7 | 19.04 ± 0.9 | 25.98 ± 0.3 | 43.08 ± 1.3 |
| 2h | 19.50 ± 1.5 | 16.83 ± 0.5 | 21.83 ± 0.8 | 23.65 ± 0.1 | 38.16 ± 1.5 |
| 3a | 19.69 ± 0.6 | 13.43 ± 0.4 | 17.35 ± 0.4 | 22.89 ± 0.2 | 39.26 ± 1.7 |
| 3b | 18.43 ± 0.7 | 16.43 ± 0.5 | 22.98 ± 0.5 | 21.65 ± 0.4 | 37.45 ± 1.4 |
| 3c | 20.17 ± 1.3 | 18.23 ± 0.7 | 21.87 ± 0.3 | 22.76 ± 0.6 | 36.87 ± 1.6 |
| 3d | 19.97 ± 1.1 | 17.23 ± 1.2 | 23.87 ± 0.2 | 24.65 ± 0.4 | 37.54 ± 1.3 |
| 3e | 18.94 ± 1.2 | 16.46 ± 0.7 | 22.14 ± 0.4 | 25.37 ± 0.3 | 34.44 ± 1.6 |

TABLE 2-continued

IC$_{50}$ values[a] (in nM) for 1a-h to 3a-h on selected cancer cell lines.

| Compound | A549[b] | MCF-7[c] | B16 | HeLa[e] | NIH3T3[f] |
|---|---|---|---|---|---|
| 3f | 18.89 ± 1.1 | 14.05 ± 0.9 | 16.64 ± 0.5 | 21.55 ± 0.6 | 38.31 ± 1.3 |
| 3g | 21.23 ± 1.5 | 17.23 ± 0.5 | 19.76 ± 0.5 | 24.87 ± 0.2 | 39.87 ± 1.6 |
| 3h | 18.86 ± 1.4 | 13.84 ± 0.4 | 16.31 ± 0.3 | 22.32 ± 0.3 | 37.16 ± 1.1 |
| Doxorubicin | 740 ± 0.4 | 580 ± 0.2 | 670 ± 0.7 | 780 ± 0.5 | 1720 ± 0.8 |

[a]50% Inhibitory concentration after 48 h of drug treatment and the values are average of three individual experiments,
[b]lung cancer,
[c]breast cancer,
[d]melanoma,
[e]cervical cancer,
[f]mouse embryonic fibroblast cell line.

ADVANTAGES OF THE PRESENT INVENTION

The present invention provides new N-((1-phenyl-9H-pyrido[3,4-b]indol-3-yl)methyl)cinnamamides are likely to be useful as anticancer agents and it also provides a process for the preparation of N-((1-phenyl-9H-pyrido[3,4-b]indol-3-yl)methyl)cinnamamides.

The N-((1-phenyl-9H-pyrido[3,4-b]indol-3-yl)methyl) cinnamamides that have been synthesized and exhibited potent cytotoxic activity against different human tumor cell lines.

We claim:

1. N-((1-phenyl-9H-pyrido[3,4-b]indol-3-yl)methyl) cinnamamides of formula A:

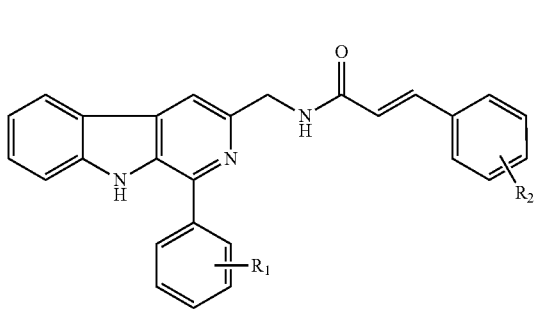

A wherein
R$_1$=3-F, 3,4,5-OMe, 4-OMe, H, 4-CF$_3$, 4-Cl, 4-OH-3-OMe, 3,4-CH$_2$—O—CH$_2$, 3,5-F, 4-OH, 1-napthyl, 9-phenanthryl, or 4-Me, and
R$_2$=3,4,5-OMe, 3,4-Cl, 4-F, 3,5-F, 2,5-OMe, 4-Cl, 4-OH-3-OMe, 3-OH, 3,4,5-OH, 4-CF$_3$, 4-OMe, or 4-NH$_2$.

2. The compound of formula A as claimed in claim 1, wherein the representative compounds of formula 1a-l to 13a-l comprises;

(E)-N-((1-(3-fluorophenyl)-9H-pyrido[3,4-b]indol-3-yl)methyl)-3-(3,4,5-trimethoxyphenyl) acrylamide (1a)
(E)-3-(3,4-dichlorophenyl)-N-((1-(3-fluorophenyl)-9H-pyrido[3,4-b]indol-3-yl)methyl)acrylamide (1b)
(E)-3-(4-fluorophenyl)-N-((1-(3-fluorophenyl)-9H-pyrido[3,4-b]indol-3-yl)methyl)acrylamide (1c)
(E)-3-(3,5-difluorophenyl)-N-((1-(3-fluorophenyl)-9H-pyrido[3,4-b]indol-3-yl)methyl)acrylamide (1d)
(E)-3-(2,5-dimethoxyphenyl)-N-((1-(3-fluorophenyl)-9H-pyrido[3,4-b]indol-3-yl)methyl)acrylamide (1e)
(E)-3-(4-chlorophenyl)-N-((1-(3-fluorophenyl)-9H-pyrido[3,4-b]indol-3-yl)methyl)acrylamide (1f)
(E)-N-((1-(3-fluorophenyl)-9H-pyrido[3,4-b]indol-3-yl)methyl)-3-(4-hydroxy-3-methoxyphenyl)acrylamide (1g)
(E)-N-((1-(3-fluorophenyl)-9H-pyrido[3,4-b]indol-3-yl)methyl)-3-(3-hydroxyphenyl)acrylamide (1h)
(E)-N-((1-(3-fluorophenyl)-9H-pyrido[3,4-b]indol-3-yl)methyl)-3-(3,4,5-trihydroxyphenyl)acrylamide (1i)
(E)-N-((1-(3-fluorophenyl)-9H-pyrido[3,4-b]indol-3-yl)methyl)-3-(4-(trifluoromethyl)phenyl)acrylamide (1j)
(E)-N-((1-(3-fluorophenyl)-9H-pyrido[3,4-b]indol-3-yl)methyl)-3-(4-methoxyphenyl)acrylamide (1k)
(E)-3-(4-aminophenyl)-N-((1-(3-fluorophenyl)-9H-pyrido[3,4-b]indol-3-yl)methyl)acrylamide (1l)
(E)-3-(3,4,5-trimethoxyphenyl)-N-((1-(3,4,5-trimethoxyphenyl)-9H-pyrido[3,4-b]indol-3-yl)methyl)acrylamide (2a)
(E)-3-(3,4-dichlorophenyl)-N-((1-(3,4,5-trimethoxyphenyl)-9H-pyrido[3,4-b]indol-3-yl)methyl)acrylamide (2b)
(E)-3-(4-fluorophenyl)-N-((1-(3,4,5-trimethoxyphenyl)-9H-pyrido[3,4-b]indol-3-yl)methyl)acrylamide (2c)
(E)-3-(3,5-difluorophenyl)-N-((1-(3,4,5-trimethoxyphenyl)-9H-pyrido[3,4-b]indol-3-yl)methyl)acrylamide (2d)
(E)-3-(2,5-dimethoxyphenyl)-N-((1-(3,4,5-trimethoxyphenyl)-9H-pyrido[3,4-b]indol-3-yl)methyl)acrylamide (2e)
(E)-3-(4-chlorophenyl)-N-((1-(3,4,5-trimethoxyphenyl)-9H-pyrido[3,4-b]indol-3-yl)methyl)acrylamide (2f)
(E)-3-(4-hydroxy-3-methoxyphenyl)-N-((1-(3,4,5-trimethoxyphenyl)-9H-pyrido[3,4-b]indol-3-yl)methyl)acrylamide (2g)
(E)-3-(3-hydroxyphenyl)-N-((1-(3,4,5-trimethoxyphenyl)-9H-pyrido[3,4-b]indol-3-yl)methyl)acrylamide (2h)
(E)-3-(3,4,5-trihydroxyphenyl)-N-((1-(3,4,5-trimethoxyphenyl)-9H-pyrido[3,4-b]indol-3-yl)methyl)acrylamide (2i)
(E)-3-(4-(trifluoromethyl)phenyl)-N-((1-(3,4,5-trimethoxyphenyl)-9H-pyrido[3,4-b]indol-3-yl)methyl)acrylamide (2j)
(E)-3-(4-methoxyphenyl)-N-((1-(3,4,5-trimethoxyphenyl)-9H-pyrido[3,4-b]indol-3-yl)methyl)acrylamide (2k)
(E)-3-(4-aminophenyl)-N-((1-(3,4,5-trimethoxyphenyl)-9H-pyrido[3,4-b]indol-3-yl)methyl)acrylamide (2l)
(E)-N-((1-(4-methoxyphenyl)-9H-pyrido[3,4-b]indol-3-yl)methyl)-3-(3,4,5-trimethoxyphenyl)acrylamide (3a)
(E)-3-(3,4-dichlorophenyl)-N-((1-(4-methoxyphenyl)-9H-pyrido[3,4-b]indol-3-yl)methyl)acrylamide (3b)

(E)-3-(4-fluorophenyl)-N-((1-(4-methoxyphenyl)-9H-pyrido[3,4-b]indol-3-yl)methyl)acrylamide (3c)
(E)-3-(3,5-difluorophenyl)-N-((1-(4-methoxyphenyl)-9H-pyrido[3,4-b]indol-3-yl)methyl)acrylamide (3d)
(E)-3-(2,5-dimethoxyphenyl)-N-((1-(4-methoxyphenyl)-9H-pyrido[3,4-b]indol-3-yl)methyl)acrylamide (3e)
(E)-3-(4-chlorophenyl)-N-((1-(4-methoxyphenyl)-9H-pyrido[3,4-b]indol-3-yl)methyl)acrylamide (3f)
(E)-3-(4-hydroxy-3-methoxyphenyl)-N-((1-(4-methoxyphenyl)-9H-pyrido[3,4-b]indol-3-yl)methyl)acrylamide (3g)
(E)-3-(3-hydroxyphenyl)-N-((1-(4-methoxyphenyl)-9H-pyrido[3,4-b]indol-3-yl)methyl)acrylamide (3h)
(E)-N-((1-(4-methoxyphenyl)-9H-pyrido[3,4-b]indol-3-yl)methyl)-3-(3,4,5-trihydroxyphenyl)acrylamide (3i)
(E)-N-((1-(4-methoxyphenyl)-9H-pyrido[3,4-b]indol-3-yl)methyl)-3-(4-(trifluoromethyl)phenyl)acrylamide (3j)
(E)-3-(4-methoxyphenyl)-N-((1-(4-methoxyphenyl)-9H-pyrido[3,4-b]indol-3-yl)methyl)acrylamide (3k)
(E)-3-(4-aminophenyl)-N-((1-(4-methoxyphenyl)-9H-pyrido[3,4-b]indol-3-yl)methyl)acrylamide (3l)
(E)-N-((1-phenyl-9H-pyrido[3,4-b]indol-3-yl)methyl)-3-(3,4,5-trimethoxyphenyl)acrylamide (4a)
(E)-3-(3,4-dichlorophenyl)-N-((1-phenyl-9H-pyrido[3,4-b]indol-3-yl)methyl)acrylamide (4b)
(E)-3-(4-fluorophenyl)-N-((1-phenyl-9H-pyrido[3,4-b]indol-3-yl)methyl)acrylamide (4c)
(E)-3-(3,5-difluorophenyl)-N-((1-phenyl-9H-pyrido[3,4-b]indol-3-yl)methyl)acrylamide (4d)
(E)-3-(2,5-dimethoxyphenyl)-N-((1-phenyl-9H-pyrido[3,4-b]indol-3-yl)methyl)acrylamide (4e)
(E)-3-(4-chlorophenyl)-N-((1-phenyl-9H-pyrido[3,4-b]indol-3-yl)methyl)acrylamide (4f)
(E)-3-(4-hydroxy-3-methoxyphenyl)-N-((1-phenyl-9H-pyrido[3,4-b]indol-3-yl)methyl)acrylamide (4g)
(E)-3-(3-hydroxyphenyl)-N-((1-phenyl-9H-pyrido[3,4-b]indol-3-yl)methyl)acrylamide (4h)
(E)-N-((1-phenyl-9H-pyrido[3,4-b]indol-3-yl)methyl)-3-(3,4,5-trihydroxyphenyl)acrylamide (4i);
(E)-N-((1-phenyl-9H-pyrido[3,4-b]indol-3-yl)methyl)-3-(4-(trifluoromethyl)phenyl)acrylamide (4j)
(E)-3-(4-methoxyphenyl)-N-((1-phenyl-9H-pyrido[3,4-b]indol-3-yl)methyl)acrylamide (4k)
(E)-3-(4-aminophenyl)-N-((1-phenyl-9H-pyrido[3,4-b]indol-3-yl)methyl)acrylamide (4l)
(E)-N-((1-(4-(trifluoromethyl)phenyl)-9H-pyrido[3,4-b]indol-3-yl)methyl)-3-(3,4,5-trimethoxyphenyl)acrylamide (5a)
(E)-3-(3,4-dichlorophenyl)-N-((1-(4-(trifluoromethyl)phenyl)-9H-pyrido[3,4-b]indol-3-yl)methyl)acrylamide (5b)
(E)-3-(4-fluorophenyl)-N-((1-(4-(trifluoromethyl)phenyl)-9H-pyrido[3,4-b]indol-3-yl)methyl)acrylamide (5c)
(E)-3-(3,5-difluorophenyl)-N-((1-(4-(trifluoromethyl)phenyl)-9H-pyrido[3,4-b]indol-3-yl)methyl)acrylamide (5d)
(E)-3-(2,5-dimethoxyphenyl)-N-((1-(4-(trifluoromethyl)phenyl)-9H-pyrido[3,4-b]indol-3-yl)methyl)acrylamide (5e)
(E)-3-(4-chlorophenyl)-N-((1-(4-(trifluoromethyl)phenyl)-9H-pyrido[3,4-b]indol-3-yl)methyl)acrylamide (5f)
(E)-3-(4-hydroxy-3-methoxyphenyl)-N-((1-(4-(trifluoromethyl)phenyl)-9H-pyrido[3,4-b]indol-3-yl)methyl)acrylamide (5g)
(E)-3-(3-hydroxyphenyl)-N-((1-(4-(trifluoromethyl)phenyl)-9H-pyrido[3,4-b]indol-3-yl)methyl)acrylamide (5h)
(E)-N-((1-(4-(trifluoromethyl)phenyl)-9H-pyrido[3,4-b]indol-3-yl)methyl)-3-(3,4,5-trihydroxyphenyl)acrylamide (5i)
(E)-3-(4-(trifluoromethyl)phenyl)-N-((1-(4-(trifluoromethyl)phenyl)-9H-pyrido[3,4-b]indol-3-yl)methyl)acrylamide (5j)
(E)-3-(4-methoxyphenyl)-N-((1-(4-(trifluoromethyl)phenyl)-9H-pyrido[3,4-b]indol-3-yl)methyl)acrylamide (5k)
(E)-3-(4-aminophenyl)-N-((1-(4-(trifluoromethyl)phenyl)-9H-pyrido[3,4-b]indol-3-yl)methyl)acrylamide (5l)
(E)-N-((1-(4-chlorophenyl)-9H-pyrido[3,4-b]indol-3-yl)methyl)-3-(3,4,5-trimethoxyphenyl)acrylamide (6a)
(E)-N-((1-(4-chlorophenyl)-9H-pyrido[3,4-b]indol-3-yl)methyl)-3-(3,4-dichlorophenyl)acrylamide (6b)
(E)-N-((1-(4-chlorophenyl)-9H-pyrido[3,4-b]indol-3-yl)methyl)-3-(4-fluorophenyl)acrylamide (6c)
(E)-N-((1-(4-chlorophenyl)-9H-pyrido[3,4-b]indol-3-yl)methyl)-3-(3,5-difluorophenyl)acrylamide (6d)
(E)-N-((1-(4-chlorophenyl)-9H-pyrido[3,4-b]indol-3-yl)methyl)-3-(2,5-dimethoxyphenyl)acrylamide (6e)
(E)-3-(4-chlorophenyl)-N-((1-(4-chlorophenyl)-9H-pyrido[3,4-b]indol-3-yl)methyl)acrylamide (6f)
(E)-N-((1-(4-chlorophenyl)-9H-pyrido[3,4-b]indol-3-yl)methyl)-3-(4-hydroxy-3-methoxyphenyl)acrylamide (6g)
(E)-N-((1-(4-chlorophenyl)-9H-pyrido[3,4-b]indol-3-yl)methyl)-3-(3-hydroxyphenyl)acrylamide (6h)
(E)-N-((1-(4-chlorophenyl)-9H-pyrido[3,4-b]indol-3-yl)methyl)-3-(3,4,5-trihydroxyphenyl)acrylamide (6i)
(E)-N-((1-(4-chlorophenyl)-9H-pyrido[3,4-b]indol-3-yl)methyl)-3-(4-(trifluoromethyl)phenyl)acrylamide (6j)
(E)-N-((1-(4-chlorophenyl)-9H-pyrido[3,4-b]indol-3-yl)methyl)-3-(4-methoxyphenyl)acrylamide (6k)
(E)-3-(4-aminophenyl)-N-((1-(4-chlorophenyl)-9H-pyrido[3,4-b]indol-3-yl)methyl)acrylamide (6l)
(E)-N-((1-(4-hydroxy-3-methoxyphenyl)-9H-pyrido[3,4-b]indol-3-yl)methyl)-3-(3,4,5-trimethoxyphenyl)acrylamide (7a)
(E)-3-(3,4-dichlorophenyl)-N-((1-(4-hydroxy-3-methoxyphenyl)-9H-pyrido[3,4-b]indol-3-yl)methyl)acrylamide (7b)
(E)-3-(4-fluorophenyl)-N-((1-(4-hydroxy-3-methoxyphenyl)-9H-pyrido[3,4-b]indol-3-yl)methyl)acrylamide (7c)
(E)-3-(3,5-difluorophenyl)-N-((1-(4-hydroxy-3-methoxyphenyl)-9H-pyrido[3,4-b]indol-3-yl)methyl)acrylamide (7d)
(E)-3-(2,5-dimethoxyphenyl)-N-((1-(4-hydroxy-3-methoxyphenyl)-9H-pyrido[3,4-b]indol-3-yl)methyl)acrylamide (7e)
(E)-3-(4-chlorophenyl)-N-((1-(4-hydroxy-3-methoxyphenyl)-9H-pyrido[3,4-b]indol-3-yl)methyl)acrylamide (7f)
(E)-3-(4-hydroxy-3-methoxyphenyl)-N-((1-(4-hydroxy-3-methoxyphenyl)-9H-pyrido[3,4-b]indol-3-yl)methyl)acrylamide (7g)
(E)-N-((1-(4-hydroxy-3-methoxyphenyl)-9H-pyrido[3,4-b]indol-3-yl)methyl)-3-(3-hydroxyphenyl)acrylamide (7h)
(E)-N-((1-(4-hydroxy-3-methoxyphenyl)-9H-pyrido[3,4-b]indol-3-yl)methyl)-3-(3,4,5-trihydroxyphenyl)acrylamide (7i)

(E)-N-((1-(4-hydroxy-3-methoxyphenyl)-9H-pyrido[3,4-b]indol-3-yl)methyl)-3-(4-(trifluoromethyl)phenyl)acrylamide (7j)

(E)-N-((1-(4-hydroxy-3-methoxyphenyl)-9H-pyrido[3,4-b]indol-3-yl)methyl)-3-(4-methoxyphenyl)acrylamide (7k)

(E)-3-(4-aminophenyl)-N-((1-(4-hydroxy-3-methoxyphenyl)-9H-pyrido[3,4-b]indol-3-yl)methyl)acrylamide (7l)

(E)-N-((1-(benzo[d][1,3]dioxol-5-yl)-9H-pyrido[3,4-b]indol-3-yl)methyl)-3-(3,4,5-trimethoxyphenyl)acrylamide (8a)

(E)-N-((1-(benzo[d][1,3]dioxol-5-yl)-9H-pyrido[3,4-b]indol-3-yl)methyl)-3-(3,4-dichlorophenyl)acrylamide (8b)

(E)-N-((1-(benzo[d][1,3]dioxol-5-yl)-9H-pyrido[3,4-b]indol-3-yl)methyl)-3-(4-fluorophenyl)acrylamide (8c)

(E)-N-((1-(benzo[d][1,3]dioxol-5-yl)-9H-pyrido[3,4-b]indol-3-yl)methyl)-3-(3,5-difluorophenyl)acrylamide (8d)

(E)-N-((1-(benzo[d][1,3]dioxol-5-yl)-9H-pyrido[3,4-b]indol-3-yl)methyl)-3-(2,5-dimethoxyphenyl)acrylamide (8e)

(E)-N-((1-(benzo[d][1,3]dioxol-5-yl)-9H-pyrido[3,4-b]indol-3-yl)methyl)-3-(4-chlorophenyl)acrylamide (8f)

(E)-N-((1-(benzo[d][1,3]dioxol-5-yl)-9H-pyrido[3,4-b]indol-3-yl)methyl)-3-(4-hydroxy-3-methoxyphenyl)acrylamide (8g)

(E)-N-((1-(benzo[d][1,3]dioxol-5-yl)-9H-pyrido[3,4-b]indol-3-yl)methyl)-3-(3-hydroxyphenyl)acrylamide (8h)

(E)-N-((1-(benzo[d][1,3]dioxol-5-yl)-9H-pyrido[3,4-b]indol-3-yl)methyl)-3-(3,4,5-trihydroxyphenyl)acrylamide (8i)

(E)-N-((1-(benzo[d][1,3]dioxol-5-yl)-9H-pyrido[3,4-b]indol-3-yl)methyl)-3-(4-(trifluoromethyl)phenyl)acrylamide (8j)

(E)-N-((1-(benzo[d][1,3]dioxol-5-yl)-9H-pyrido[3,4-b]indol-3-yl)methyl)-3-(4-methoxyphenyl)acrylamide (8k)

(E)-3-(4-aminophenyl)-N-((1-(benzo[d][1,3]dioxol-5-yl)-9H-pyrido[3,4-b]indol-3-yl)methyl)acrylamide (8l)

(E)-N-((1-(3,5-difluorophenyl)-9H-pyrido[3,4-b]indol-3-yl)methyl)-3-(3,4,5-trimethoxyphenyl)acrylamide (9a)

(E)-3-(3,4-dichlorophenyl)-N-((1-(3,5-difluorophenyl)-9H-pyrido[3,4-b]indol-3-yl)methyl)acrylamide (9b)

(E)-N-((1-(3,5-difluorophenyl)-9H-pyrido[3,4-b]indol-3-yl)methyl)-3-(4-fluorophenyl)acrylamide (9c)

(E)-3-(3,5-difluorophenyl)-N-((1-(3,5-difluorophenyl)-9H-pyrido[3,4-b]indol-3-yl)methyl)acrylamide (9d)

(E)-N-((1-(3,5-difluorophenyl)-9H-pyrido[3,4-b]indol-3-yl)methyl)-3-(2,5-dimethoxyphenyl)acrylamide (9e)

(E)-3-(4-chlorophenyl)-N-((1-(3,5-difluorophenyl)-9H-pyrido[3,4-b]indol-3-yl)methyl)acrylamide (9f)

(E)-N-((1-(3,5-difluorophenyl)-9H-pyrido[3,4-b]indol-3-yl)methyl)-3-(4-hydroxy-3-methoxyphenyl)acrylamide (9g)

(E)-N-((1-(3,5-difluorophenyl)-9H-pyrido[3,4-b]indol-3-yl)methyl)-3-(3-hydroxyphenyl)acrylamide (9h)

(E)-N-((1-(3,5-difluorophenyl)-9H-pyrido[3,4-b]indol-3-yl)methyl)-3-(3,4,5-trihydroxyphenyl)acrylamide (9i)

(E)-N-((1-(3,5-difluorophenyl)-9H-pyrido[3,4-b]indol-3-yl)methyl)-3-(4-(trifluoromethyl)phenyl)acrylamide (9j)

(E)-N-((1-(3,5-difluorophenyl)-9H-pyrido[3,4-b]indol-3-yl)methyl)-3-(4-methoxyphenyl)acrylamide (9k)

(E)-3-(4-aminophenyl)-N-((1-(3,5-difluorophenyl)-9H-pyrido[3,4-b]indol-3-yl)methyl)acrylamide (9l)

(E)-N-((1-(4-hydroxyphenyl)-9H-pyrido[3,4-b]indol-3-yl)methyl)-3-(3,4,5-trimethoxyphenyl)acrylamide (10a)

(E)-3-(3,4-dichlorophenyl)-N-((1-(4-hydroxyphenyl)-9H-pyrido[3,4-b]indol-3-yl)methyl)acrylamide (10b)

(E)-3-(4-fluorophenyl)-N-((1-(4-hydroxyphenyl)-9H-pyrido[3,4-b]indol-3-yl)methyl)acrylamide (10c)

(E)-3-(3,5-difluorophenyl)-N-((1-(4-hydroxyphenyl)-9H-pyrido[3,4-b]indol-3-yl)methyl)acrylamide (10d)

(E)-3-(2,5-dimethoxyphenyl)-N-((1-(4-hydroxyphenyl)-9H-pyrido[3,4-b]indol-3-yl)methyl)acrylamide (10e)

(E)-3-(4-chlorophenyl)-N-((1-(4-hydroxyphenyl)-9H-pyrido[3,4-b]indol-3-yl)methyl)acrylamide (10f)

(E)-3-(4-hydroxy-3-methoxyphenyl)-N-((1-(4-hydroxyphenyl)-9H-pyrido[3,4-b]indol-3-yl)methyl)acrylamide (10g)

(E)-3-(3-hydroxyphenyl)-N-((1-(4-hydroxyphenyl)-9H-pyrido[3,4-b]indol-3-yl)methyl)acrylamide (10h)

(E)-N-((1-(4-hydroxyphenyl)-9H-pyrido[3,4-b]indol-3-yl)methyl)-3-(3,4,5-trihydroxyphenyl)acrylamide (10i)

(E)-N-((1-(4-hydroxyphenyl)-9H-pyrido[3,4-b]indol-3-yl)methyl)-3-(4-(trifluoromethyl)phenyl)acrylamide (10j)

(E)-N-((1-(4-hydroxyphenyl)-9H-pyrido[3,4-b]indol-3-yl)methyl)-3-(4-methoxyphenyl)acrylamide (10k)

(E)-3-(4-aminophenyl)-N-((1-(4-hydroxyphenyl)-9H-pyrido[3,4-b]indol-3-yl)methyl)acrylamide (10l)

(E)-N-((1-(naphthalen-1-yl)-9H-pyrido[3,4-b]indol-3-yl)methyl)-3-(3,4,5-trimethoxyphenyl)acrylamide (11a)

(E)-3-(3,4-dichlorophenyl)-N-((1-(naphthalen-1-yl)-9H-pyrido[3,4-b]indol-3-yl)methyl)acrylamide (11b)

(E)-3-(4-fluorophenyl)-N-((1-(naphthalen-1-yl)-9H-pyrido[3,4-b]indol-3-yl)methyl)acrylamide (11c)

(E)-3-(3,5-difluorophenyl)-N-((1-(naphthalen-1-yl)-9H-pyrido[3,4-b]indol-3-yl)methyl)acrylamide (11d)

(E)-3-(2,5-dimethoxyphenyl)-N-((1-(naphthalen-1-yl)-9H-pyrido[3,4-b]indol-3-yl)methyl)acrylamide (11e)

(E)-3-(4-chlorophenyl)-N-((1-(naphthalen-1-yl)-9H-pyrido[3,4-b]indol-3-yl)methyl)acrylamide (11f)

(E)-3-(4-hydroxy-3-methoxyphenyl)-N-((1-(naphthalen-1-yl)-9H-pyrido[3,4-b]indol-3-yl)methyl)acrylamide (11g)

(E)-3-(3-hydroxyphenyl)-N-((1-(naphthalen-1-yl)-9H-pyrido[3,4-b]indol-3-yl)methyl)acrylamide (11h)

(E)-N-((1-(naphthalen-1-yl)-9H-pyrido[3,4-b]indol-3-yl)methyl)-3-(3,4,5-trihydroxyphenyl)acrylamide (11i)

(E)-N-((1-(naphthalen-1-yl)-9H-pyrido[3,4-b]indol-3-yl)methyl)-3-(4-(trifluoromethyl)phenyl)acrylamide (11j)

(E)-3-(4-methoxyphenyl)-N-((1-(naphthalen-1-yl)-9H-pyrido[3,4-b]indol-3-yl)methyl)acrylamide (11k)

(E)-3-(4-aminophenyl)-N-((1-(naphthalen-1-yl)-9H-pyrido[3,4-b]indol-3-yl)methyl)acrylamide (11l)

(E)-N-((1-(phenanthren-9-yl)-9H-pyrido[3,4-b]indol-3-yl)methyl)-3-(3,4,5-trimethoxyphenyl)acrylamide (12a)

(E)-3-(3,4-dichlorophenyl)-N-((1-(phenanthren-9-yl)-9H-pyrido[3,4-b]indol-3-yl)methyl)acrylamide (12b)

(E)-3-(4-fluorophenyl)-N-((1-(phenanthren-9-yl)-9H-pyrido[3,4-b]indol-3-yl)methyl)acrylamide (12c)

(E)-3-(3,5-difluorophenyl)-N-((1-(phenanthren-9-yl)-9H-pyrido[3,4-b]indol-3-yl)methyl)acrylamide (12d)

(E)-3-(2,5-dimethoxyphenyl)-N-((1-(phenanthren-9-yl)-9H-pyrido[3,4-b]indol-3-yl)methyl)acrylamide (12e)

(E)-3-(4-chlorophenyl)-N-((1-(phenanthren-9-yl)-9H-pyrido[3,4-b]indol-3-yl)methyl)acrylamide (12f)

(E)-3-(4-hydroxy-3-methoxyphenyl)-N-((1-(phenanthren-9-yl)-9H-pyrido[3,4-b]indol-3-yl)methyl)acrylamide (12g)

(E)-3-(3-hydroxyphenyl)-N-((1-(phenanthren-9-yl)-9H-pyrido[3,4-b]indol-3-yl)methyl)acrylamide (12h)

(E)-N-((1-(phenanthren-9-yl)-9H-pyrido[3,4-b]indol-3-yl)methyl)-3-(3,4,5-trihydroxyphenyl)acrylamide (12i)

(E)-N-((1-(phenanthren-9-yl)-9H-pyrido[3,4-b]indol-3-yl)methyl)-3-(4-(trifluoromethyl)phenyl)acrylamide (12j)

(E)-3-(4-methoxyphenyl)-N-((1-(phenanthren-9-yl)-9H-pyrido[3,4-b]indol-3-yl)methyl)acrylamide (12k)

(E)-3-(4-aminophenyl)-N-((1-(phenanthren-9-yl)-9H-pyrido[3,4-b]indol-3-yl)methyl)acrylamide (12l)

(E)-N-((1-(p-tolyl)-9H-pyrido[3,4-b]indol-3-yl)methyl)-3-(3,4,5-trimethoxyphenyl)acrylamide (13a)

(E)-3-(3,4-dichlorophenyl)-N-((1-(p-tolyl)-9H-pyrido[3,4-b]indol-3-yl)methyl)acrylamide (13b)

(E)-3-(4-fluorophenyl)-N-((1-(p-tolyl)-9H-pyrido[3,4-b]indol-3-yl)methyl)acrylamide (13c)

(E)-3-(3,5-difluorophenyl)-N-((1-(p-tolyl)-9H-pyrido[3,4-b]indol-3-yl)methyl)acrylamide (13d)

(E)-3-(2,5-dimethoxyphenyl)-N-((1-(p-tolyl)-9H-pyrido[3,4-b]indol-3-yl)methyl)acrylamide (13e)

(E)-3-(4-chlorophenyl)-N-((1-(p-tolyl)-9H-pyrido[3,4-b]indol-3-yl)methyl)acrylamide (13f)

(E)-3-(4-hydroxy-3-methoxyphenyl)-N-((1-(p-tolyl)-9H-pyrido[3,4-b]indol-3-yl)methyl)acrylamide (13g)

(E)-3-(3-hydroxyphenyl)-N-((1-(p-tolyl)-9H-pyrido[3,4-b]indol-3-yl)methyl)acrylamide (13h)

(E)-N-((1-(p-tolyl)-9H-pyrido[3,4-b]indol-3-yl)methyl)-3-(3,4,5-trihydroxyphenyl)acrylamide (13i)

(E)-N-((1-(p-tolyl)-9H-pyrido[3,4-b]indol-3-yl)methyl)-3-(4-(trifluoromethyl)phenyl)acrylamide (13j)

(E)-3-(4-methoxyphenyl)-N-((1-(p-tolyl)-9H-pyrido[3,4-b]indol-3-yl)methyl)acrylamide (13k)

(E)-3-(4-aminophenyl)-N-((1-(p-tolyl)-9H-pyrido[3,4-b]indol-3-yl)methyl)acrylamide (13l).

3. A compound of formula A as claimed in claim 1 which exhibits cytotoxic activity against at least one cancer cell line selected from lung cancer, breast cancer, melanoma, cervical cancer and embryonic fibroblast cancer.

4. A process for the preparation of compounds of formula A as claimed in claim 1, wherein the said process comprises the step:
  i. reacting an amino compound of formula 21a-m with an acid of formula 22a-l

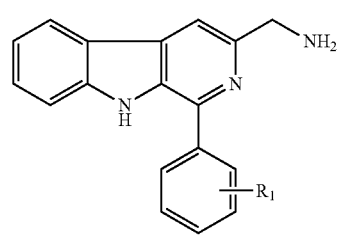

21a-m wherein $R_1$=3-F, 3,4,5-OMe, 4-OMe, H, 4-CF$_3$, 4-Cl, 4-OH-3-OMe, 3,4-CH$_2$—O—CH$_2$, 3,5-F, 4-OH, 1-napthyl, 9-phenanthryl, 4-Me,

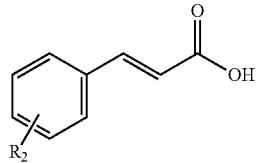

22a-l wherein $R_2$=3,4,5-OMe, 3,4-Cl, 4-F, 3,5-F, 2,5-OMe, 4-Cl, 4-OH-3-OMe, 3-OH, 3,4,5-OH, 4-CF$_3$, 4-OMe, 4-NH$_2$, in a solvent with coupling agent and a base (Triethylamine or N,N-Diisopropylethylamine) under inert atmosphere at a temperature in the range of 35 to 37° C. for a period of in the range of 12 to 18 h to get 1a-l to 13a-l.

5. The process as claimed in claim 4, wherein the compound of formula 21 a-m is selected from the group consisting of

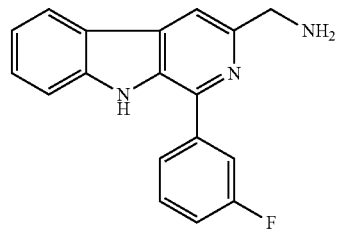

21a

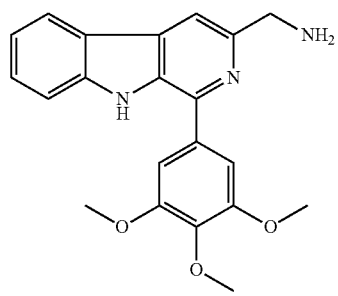

21b

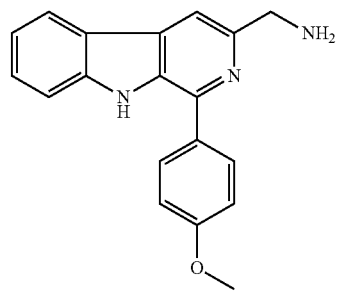

21c

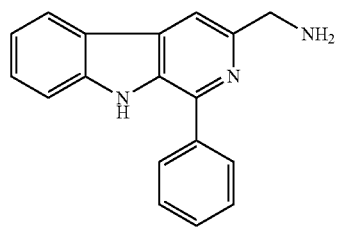

21d

21e 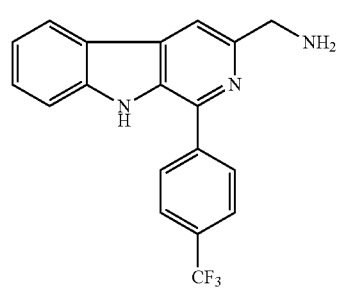
21f 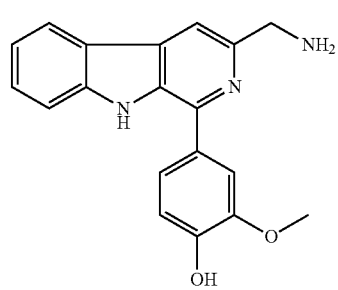
21g 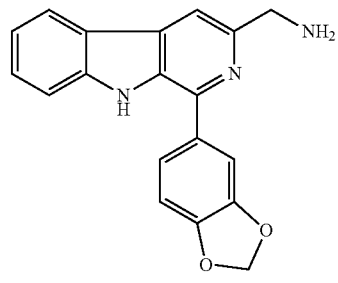
21h 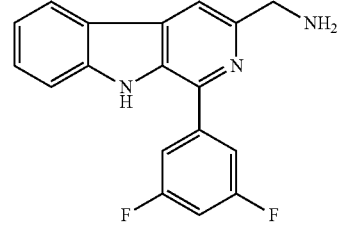
21i 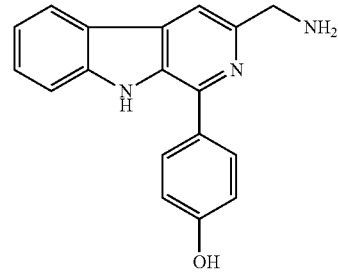
21j
21k 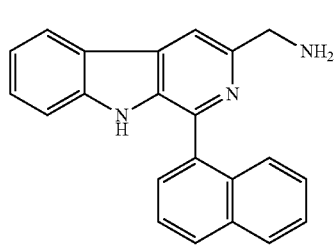
21l 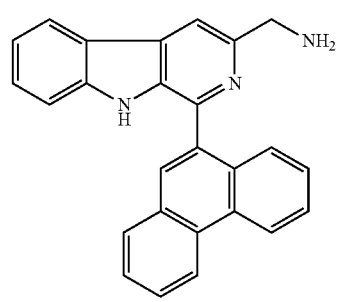
21m 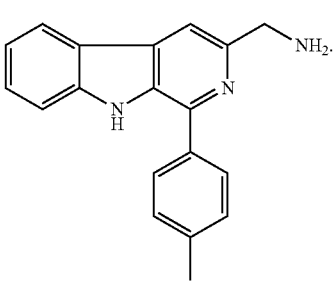
6. The process as claimed in claim 4, wherein the compound of formula 22 a-l is selected from the group consisting of
22a 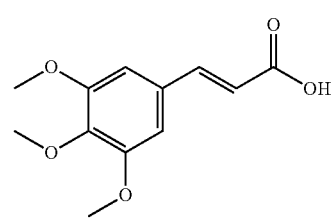
22b 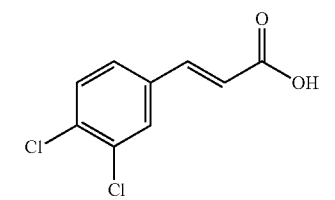
22c 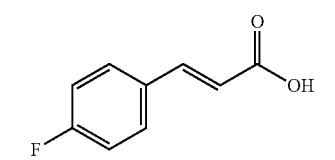

-continued

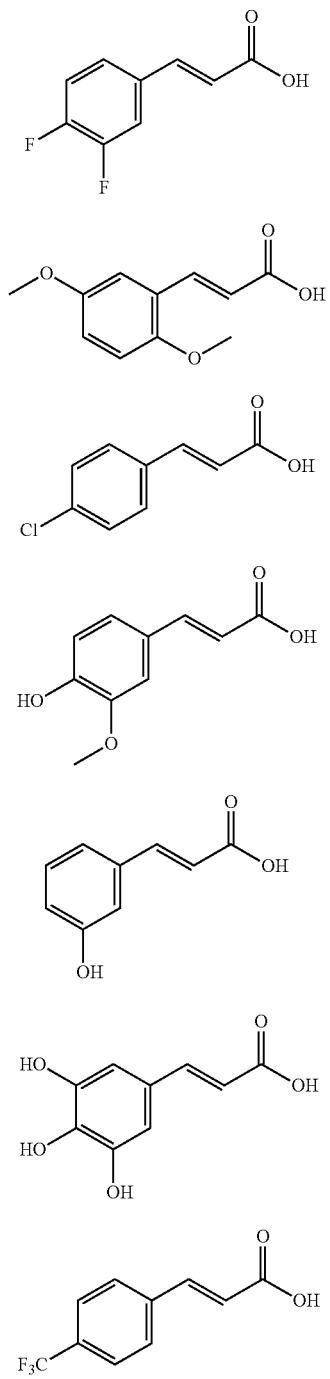

22d
22e
22f
22g
22h
22i
22j

-continued

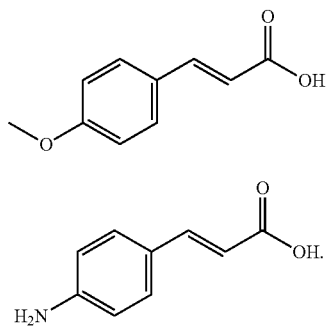

22k
22l

7. The process as claimed in claim 4, wherein the solvent is selected from dimethylformamide or dichloromethane.

8. The process as claimed in claim 4, wherein the coupling agent is selected from ((2-(1H-benzotriazol-1-yl)-1,1,3,3-tetramethyluronium hexafluorophosphate), (1-[bis(dimethylamino)methylene]-1H-1,2,3-triazolo[4,5-b]pyridinium 3-oxid hexafluorophosphate), 1-(3-dimethylaminopropyl)-3 ethylcarbodiimide hydrochloride and hydroxybenzotriazole).

9. The compound of formula A as claimed in claim 1, wherein the $IC_{50}$ value of in vitro anti-cancer activity is in the range of 13 to 45 nM for breast cancer cell lines MCF-7.

10. A method for the cytotoxic treatment of cancer cells selected from lung cancer, breast cancer, melanoma, cervical cancer and embryonic fibroblast cancer comprising application to said cells of a compound of N-((1-phenyl-9H-pyrido[3,4-b]indol-3-yl)methyl) cinnamamides of formula A:

A

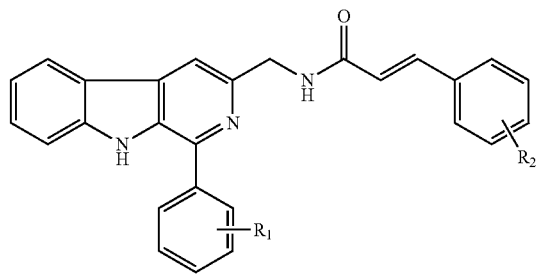

wherein
$R_1$=3-F, 3,4,5-OMe, 4-OMe, H, 4-$CF_3$, 4-Cl, 4-OH-3-OMe, 3,4-$CH_2$—O—$CH_2$, 3,5-F, 4-OH, 1-napthyl, 9-phenanthryl, or 4-Me, and
$R_2$=3,4,5-OMe, 3,4-Cl, 4-F, 3,5-F, 2,5-OMe, 4-Cl, 4-OH-3-OMe, 3-OH, 3,4,5-OH, 4-$CF_3$, 4-OMe, or 4-$NH_2$.

* * * * *